US006235789B1

(12) United States Patent
Ohkawa et al.

(10) Patent No.: US 6,235,789 B1

(45) **Date of Patent: *May 22, 2001**

(54) BENZOCYCLOALKENE COMPOUNDS, THEIR PRODUCTION AND USE

(75) Inventors: Shigenori Ohkawa, Osaka; Osamu Uchikawa; Masaomi Miyamoto, both of Hyogo, all of (JP)

(73) Assignee: Takeda Chemical Industries, Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 25 days.

(21) Appl. No.: 08/530,148

(22) PCT Filed: Sep. 11, 1995

(86) PCT No.: PCT/JP95/01796

§ 371 Date: May 28, 1997

§ 102(e) Date: May 28, 1997

(87) PCT Pub. No.: WO96/08466

PCT Pub. Date: Mar. 21, 1996

(30) Foreign Application Priority Data

Sep. 12, 1994 (JP) ........................................ 6-217188

(51) Int. Cl.[7] .......................... A61K 31/16; C07C 233/04

(52) U.S. Cl. .......................... 514/630; 514/595; 514/617; 514/624; 514/628; 514/629; 560/24; 560/37; 564/56; 564/183; 564/189; 564/204; 564/219; 564/138

(58) Field of Search .................................... 514/617, 628, 514/630, 595, 624, 506, 629; 564/183, 219, 189, 204, 138, 56; 560/24, 37

(56) References Cited

U.S. PATENT DOCUMENTS

| | | | | |
|---|---|---|---|---|
| 5,225,442 | * | 7/1993 | Andrieux et al. | 564/219 |
| 5,464,872 | * | 11/1995 | Langlois et al. | 564/219 |
| 5,591,775 | * | 1/1997 | Depreux et al. | 514/617 |
| 5,661,186 | | 8/1997 | Takaki et al. | 514/630 |
| 5,668,180 | * | 9/1997 | Lesieur et al. | 564/219 |

FOREIGN PATENT DOCUMENTS

| | | |
|---|---|---|
| 1221639 | 5/1987 | (CA) . |
| 0384917 | 9/1990 | (EP) . |
| 0420064 | 4/1991 | (EP) . |
| 0447285 | 9/1991 | (EP) . |
| 0530087 | 3/1993 | (EP) . |
| 0562956 | 9/1993 | (EP) . |
| 0728738 | 8/1996 | (EP) . |
| 2093837 | 9/1982 | (GB) . |

OTHER PUBLICATIONS

Chemical Abstracts, vol. 95, No. 7 (1981) 061825.
J. Med. Chem., vol. 26, No. 6 (1983) 813–16.
J. Med. Chem. vol. 35, No. 8 (1992) 1484–85.
Pol. J. Pharmacol. Pharma., vol. 32 (1980) 577–585.

* cited by examiner

*Primary Examiner*—Porfirio Nazario-Gonzalez
(74) *Attorney, Agent, or Firm*—Wenderoth, Lind & Ponack, L.L.P.

(57) ABSTRACT

A compound of the formula

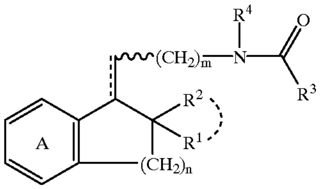

wherein $R^1$ and $R^2$ are H, a hydrocarbon group or a heterocyclic group, or $R^1$ and $R^2$ are combinedly a spiro ring; $R^3$ is a hydrocarbon group, a substituted amino group, a substituted hydroxyl group or a heterocyclic group; $R^4$ is H or alkyl; ring A is a substituted benzene ring; m and n denote 1 to 4; ......... means a single or double bond or a salt, a process of producing thereof and a composition having a binding affinity for melatonin receptor.

50 Claims, No Drawings

BENZOCYCLOALKENE COMPOUNDS, THEIR PRODUCTION AND USE

This application is a 371 of PCT/JP95/07196, filed Sep. 9, 1995.

TECHNICAL FIELD

This invention relates to a novel benzocycloalkene derivative having an excellent binding affinity for melatonin receptor, a process for producing it and use.

BACKGROUND ART

Melatonin (N-acetyl-5-methoxytryptamine), which is a hormone synthesized and secreted principally in the pineal gland, increases in dark circumstances and decreases in light circumstances. Further, melatonin exerts suppressively on pigment cells or female gonad and acts as a synchronous factor of biological clock while taking part in transmittance of photoperiodic code. Therefore, melatonin is considered to be possibly used for the therapy of diseases related with melatonin activity, such as reproduction and endocrinic disorders, sleep-awake rythm disorders, jet lag syndrome and various disorders related to ageing. Recently it was reported in Ann. N.Y. Acad. Sci., Vol. 719, PP.456–460 (1994) that the production of melatonin decline steadily into old age and the supplementing melatonin could reset the body's aging clock; However, in "Bioorganic & Medicinal Chemistry Letters, Vol.4, p.1485 (1994)", there is described that, when the action on central nervous system is expected, melatonin is shown to be inactive by a peripheral administration.

As a compound having a melatonin receptor affinity, 1) a compound having acylamino group at the 2-position of tetrahydronaphthalene and of the formula

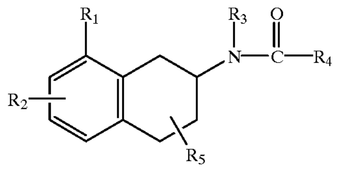

wherein $R_1$ and $R_2$ are independently, H, alkoxy etc., $R_3$ and $R_5$ are H etc., $R_4$ is aryl, $C_{1-4}$ alkyl etc., is described in EP-A-420064, 2) a compound having acylaminoethyl group at the 1-position of naphthalene and of the formula

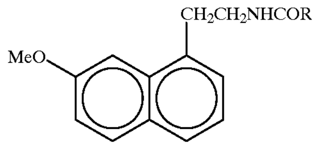

wherein R is propyl, butyl, cyclopropyl etc., is described in "Journal of Medicinal Chemistry, No.35, pp.1484–1486, (1992)" and 3) (naphthylethyl)ureas are described in EP-A-530087.

And, as compounds having a benzocycloalkene structure 1) a compound of the formula

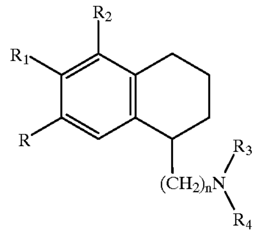

wherein R, $R_1$ and $R_2$ are independently H, lower alkoxy etc., $R_3$ and $R_4$ are independently H, lower acyl (—CO—$R^5$) etc., $R^5$ is lower alkyl, n is 1 to 4, and having adrenaline activity and being useful as therapeutic agents in the treatment of hypertension is described in GB 2093837, 2) a compound of the formula

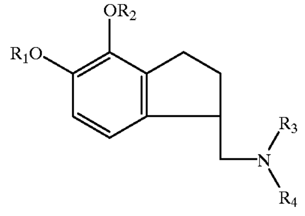

wherein $R_1$, $R_2$ $R_3$ and $R_4$ are independently H, lower alkyl, and having $\alpha_2$-adrenergic receptor agonist activity and being useful for hypertension is described in CA 1221639, 3) a compound of the formula

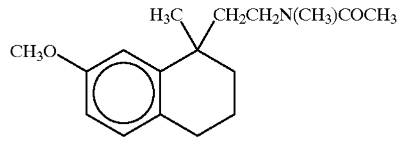

which is used as an intermediate of eptazocin hydrobromide being useful as a narcotic-antagonizing analgesic for relieving post-operative pains is described in EP-A-384917, 4) a compound of the formula

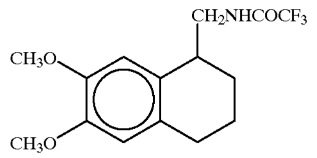

which is used as a starting material of tetralin having dopamine activity is described in "Journal of Medicinal chemistry, No. 26, p. 813, (1983)".

None of them refers to the melatonin receptors affinities.

A melatonin agonist, which is different from melatonin in the structure, has stronger activities than those of melatonin, is metabolicaly stable and is excellent in the transferability into brain, can be expected to show superior therapeutic effects to those of melatonin. And, when the antagonistic activities of melatonin are desired, creation of a new melatonin antagonist is necessary.

At the present circumstances, no compounds which are fully satisfactory in the activities of melatonin receptors, in metabolical stability and in transferability into brain have been found. So, development of compounds, which are different from the above-mentioned known compounds in chemical structure, have excellent melatonin receptor affinities and are fully satisfactory as medicines, is ardently desired.

DISCLOSURE OF INVENTION

The present inventors diligently conducted extensive study and succeeded in creation of the novel compound which is characterized in having a $R^3$CO-amino-$C_{2-5}$ alkyl group or a $R^3$CO-amino-$C_{2-5}$ alkylidene group ($R^3$ is of the same meanings as defined hereinafter) at the 1-position of benzocycloalkenes of the formula:

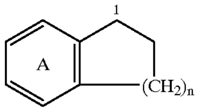

wherein all symbols are of the same meaning as defined hereinafter and represented by the formula:

(I)

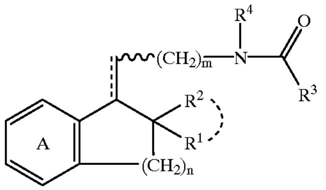

wherein $R^1$ and $R^2$ independently represent a hydrogen atom, an optionally substituted hydrocarbon group or an optionally substituted heterocyclic group, or $R^1$ and $R^2$, taken together with the adjacent carbon atom, may form an optionally substituted spiro ring;

$R^3$ represents an optionally substituted hydrocarbon group, an optionally substituted amino group, a substituted hydroxyl group or an optionally substituted heterocyclic group;

$R^4$ represents a hydrogen atom or an optionally substituted lower alkyl group; ring A represents a substituted benzene ring; m and n independently represent an integer of 1 to 4; and ......... represents a single bond or a double bond, or a salt thereof, and found that the compound (I) or a salt thereof and compound (Ia) containing the compound (I) and represented by the formula:

(Ia)

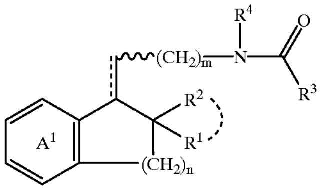

wherein ring $A^1$ represents an optionally substituted benzene ring and other symbols are of the same meaning as defined above, or salt thereof are excellent in affinity for melatonin receptors as melatonin agonists or antagonists and are satisfactory as medicines. Based on these findings, the present inventors have completed the invention.

More specifically, this invention relates to (1) the compound (I) or salts thereof, (2) the compound described in the above (1), in which $R^1$ and $R^2$ are independently a hydrogen atom or an optionally substituted hydrocarbon group, or $R^1$ and $R^2$, taken together with the adjacent carbon atom, may form a spiro ring, $R^3$ represents an optionally substituted hydrocarbon group, an optionally substituted amino group or a substituted hydroxyl group, (3) the compound described in the above (1), in which the hydrocarbon group is a $C_{1-6}$ aliphatic hydrocarbon group, a $C_{3-6}$ monocyclic saturated hydrocarbon group or a $C_{6-10}$ aromatic hydrocarbon group, (4) the compound described in the above (1), in which the heterocyclic group is a 5- to 7-membered heterocyclic group having 1 to 3 hetero-atoms selected from nitrogen, oxygen and sulfur, (5) the compound described in the above (1), in which the spiro ring is a 3 to 8-membered ring, (6) the compound described in the above (1), in which the substituent of the amino group is an optionally substituted lower alkyl group or an optionally substituted aryl group, (7) the compound described in the above (1), in which the substituted hydroxyl group is an optionally substituted lower alkoxy group, (8) the compound described in the above (1), in which $R^1$ and $R^2$ are independently a hydrogen atom, a lower alkyl group or an aryl group, (9) the compound described in the above (1), in which $R^1$ and $R^2$ are independently a hydrogen atom or a lower alkyl group,

(10) the compound described in the above (1), in which $R^3$ is (i) an optionally substituted lower alkyl group, (ii) an optionally substituted lower cycloalkyl group, (iii) an optionally substituted lower alkenyl group, (iv) an optionally substituted aryl group, (v) an optionally substituted lower alkylamino group, (vi) an optionally substituted arylamino group, (vii) an optionally substituted 5- or 6-membered nitrogen-containing heterocyclic group or (viii) an optionally substituted lower alkoxy group,

(11) the compound described in the above (1), in which $R^3$ is an optionally halogenated $C_{1-3}$ alkyl group,

(12) the compound described in the above (1), in which $R^4$ is a hydrogen atom,

(13) the compound described in the above (1), in which ......... is a single bond,

(14) the compound described in the above (1), in which n is an integer of 1 to 3,

(15) the compound described in the above (1), in which n is 1,

(16) the compound described in the above (1), in which m is 1 or 2,

(17) the compound described in the above (1), in which the ring A is a benzene ring having 1 to 3 substituents selected from the group consisting of (i) a halogen atom, (ii) a lower alkyl group, (iii) a lower alkoxy group optionally substituted with an aryl group, (iv) hydroxyl group and (v) a mono-lower alkylamino group,

(18) the compound described in the above (1), in which the ring A is represented by the formula

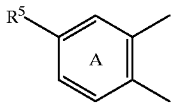

wherein $R^5$ is an optionally substituted lower alkoxy group,

(19) the compound described in the above (1), in which m is 1, n is 2 and ......... is a single bond,

(20) the compound described in the above (1), in which m is 1, n is 2 and ......... is a double bond,

(21) the compound described in the above (1), in which m is 1 or 2, n is 1 and ......... is a single bond,

(22) the compound described in the above (1), in which m is 1, n is 3 and ......... is a double bond,

(23) the compound described in the above (1), in which $R^1$, $R^2$ and $R^4$ all are a hydrogen atoms,

(24) the compound described in the above (23), in which $R^3$ is an optionally halogenated lower alkyl group,

(25) the compound described in the above (23), in which $R^3$ is a lower cycloalkyl group,

(26) the compound described in the above (18), in which $R^1$, $R^2$ and $R^4$ all are a hydrogen atoms, $R^3$ is an optionally halogenated lower alkyl group and both of m and n are 1,

(27) the compound described in the above (1), which is the compound represented by the formula:

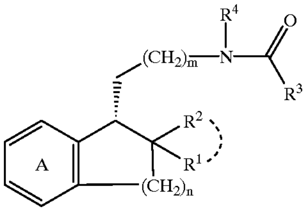

wherein symbols are of the same meaning as defined above,

(28) the compound described in the above (1), which is (S)-1-[2-(acetylamino)ethyl]-6-methoxyindan, (S)-6-methoxy-1-[2-(trifluoroacetylamino)ethyl]indan, (S)-1-[2-(cyclopropylcarbonylamino)ethyl]-6-methoxyindan, (S)-1-[2-(propionylamino)ethyl]-6-methoxyindan, (S)-1-[2-(isobutyrylamino)ethyl]-6-methoxyindan, (S)-1-[2-(acetylamino)ethyl]-7-methoxy-1,2,3,4-tetrahydronaphthalene, (S)-7-methoxy-1-[2-(trifluoroacetylamino)ethyl]-1,2,3,4-tetrahydronaphthalene or (S)-1-[2-(cyclopropylcarbonylamino)ethyl]-7-methoxy-1,2,3,4-tetrahydronaphthalene,

(29) the compound described in the above (1), which is (S)-1-[2-(trifluoroacetylamino)ethyl]-6-methoxyindan,

(30) the compound described in the above (1), which is (S)-1-[2-(propionylamino)ethyl]-6-methoxyindan,

(31) (S)-1-(2-aminoethyl)-6-methoxyindan or a salt thereof,

(32) a process for producing a compound described in the above (1), which comprises reacting a compound represented by the formula:

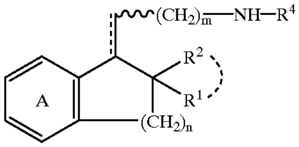

wherein all symbols are of the same meaning as defined above, or a salt thereof, with a carboxylic acid of the formula: $R^3$ COOH ($R^3$ is as defined above), a salt or reactive derivative thereof, or an isocyanate derivative of the formula: $R^{3'}N{=}C{=}O$ ($R^{3'}$ has the same meaning as $R^3$ defined above except —NH),

(33) a pharmaceutical composition which comprises a compound described in the above (1), if necessary together with a pharmaceutically acceptable carrier,

(34) the composition described in the above (33), which has a binding affinity for melatonin receptor,

(35) the composition described in the above (34), which is a regulating agent of circadian rhythm,

(36) the composition described in the above (35), which is a regulating agent of sleep-awake rhythm,

(37) the composition described in the above (36), which is a regulating agent of time zone change syndrome,

(38) the composition described in the above (35), which is a therapeutic agent of sleep disorders,

(39) a composition having a binding affinity for melatonin receptor which comprises a compound (Ia) or a salt and a pharmaceutically acceptable carrier, and

(40) the composition described in the above (39), which is a melatonin receptor agonistic composition.

"Hydrocarbon group" of the term "optionally substituted hydrocarbon group" used in this specification include, among others, aliphatic hydrocarbon groups, monocyclic saturated hydrocarbon groups and aromatic hydrocarbon groups. The carbon number of the hydrocarbon group is preferable 1 to 16. An alkyl group, an alkenyl group, an alkynyl group, a cycloalkyl group and an aryl group are exemplified.

"Alkyl group" is preferably a lower alkyl group, for example, $C_{1-6}$ alkyl groups such as methyl, ethyl, propyl, isopropyl, butyl, isobutyl, sec-butyl, tert-butyl, pentyl and hexyl are used.

"Alkenyl group" is preferably a lower alkenyl group, for example, $C_{2-6}$ alkenyl groups such as vinyl, 1-propenyl, allyl, isopropenyl, butenyl and isobutenyl are used.

"Alkynyl group" is preferably a lower alkynyl group, for example, $C_{2-6}$ alkynyl groups such as ethynyl and 1-propynyl are used.

"Cycloalkyl group" is preferably a lower cycloalkyl group, for example, $C_{3-6}$ cycloalkyl groups such as cyclopropyl, cyclobutyl, cyclopentyl and cyclohexyl are used.

"Aryl group" is preferably $C_{6-14}$ aryl groups such as phenyl, xylyl, 1-naphthyl, 2-naphthyl, biphenylyl, 2-indenyl and 2-anthlyl. Among others, a phenyl group, for example, is used.

Examples of the substituents, which "hydrocarbon group" of "optionally substituted hydrocarbon group" may optionally have, include halogen atoms (e.g. fluorine, chlorine, bromine and iodine), nitro group, cyano group, hydroxyl group, optionally halogenated $C_{1-6}$ alkyl groups (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl, a lower alkoxy group (e.g. $C_{1-6}$ alkoxy groups such as methoxy, ethoxy, propoxy, isopropoxy, butoxy, isobutoxy, pentyloxy and hexyloxy), amino group, mono-lower alkyl amino group (e.g. mono-$C_{1-6}$ alkylamino group such as methylamino and ethylamino), di-lower alkylamino group (e.g. di-$C_{1-6}$ alkylamino group such as dimethyamino and diethylamino), carboxyl group, lower alkylcarbonyl group ($C_{1-6}$ alkyl-carbonyl group such as acetyl and propionyl), lower alkoxycarbonyl group (e.g. $C_{1-6}$ alkoxy-carbonyl group such as methoxycarbonyl, ethoxycarbonyl, propoxycarbonyl and butoxycarbonyl), carbamoyl group, mono-lower alkylcarbamoyl group (e.g. mono-$C_{1-6}$ alkylcarbamoyl group such as methylcarbamoyl and ethylcarbamoyl), di-lower alkylcarbamoyl group (e.g. di-$C_{1-6}$ alkylcarbamoyl group such as dimethylcarbamoyl and diethylcarbamoyl), arylcarbamoyl group (e.g. $C_{6-10}$ arylcarbamoyl group such as phenylcarbamoyl and naphthylcarbamoyl), aryl group (e.g. $C_{6-10}$aryl group such as phenyl and naphthyl) and aryloxy group (e.g. $C_{6-10}$ aryloxy group such as phenyloxy and naphthyloxy), optionally halogenated lower alkylcarbonylamino group (e.g. optionally halogenated $C_{1-6}$ alkyl-carbonylamino group such as acetylamino, trifluoroacetylamino). “Hydrocarbon group” of “optionally substituted hydrocarbon group” may optionally have 1 to 5, preferably 1 to 3, of these substituents. When the number of the substituents is two or more, they may be the same one or different from one another.

“Heterocyclic group” of the term “optionally substituted heterocyclic group” used in this specification includes, for example, 5- to 14-membered (preferably 5- to 10-membered) (mono-, di- or tricyclic, preferably monocyclic or dicyclic) heterocyclic group containing, besides carbon atom, 1 to 4 hetero atoms, preferably 1 to 3, selected from nitrogen atom, oxygen atom and sulfur atom. As the “heterocyclic group”, use is made of 5-membered cyclic group containing, besides carbon atom, 1 to 4 hetero atoms selected from oxygen atom, sulfur atom and nitrogen atom, as exemplified by 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isooxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl, and 1H- or 2H-tetrazolyl; 6-membered cyclic group containing, besides carbon atom, 1 to 4 hetero atoms selected from oxygen atom, sulfur atom and nitrogen atom, as exemplified by 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, pyranyl, thiopyranyl, 1,4-oxazinyl, 1,4-thiazinyl, 1,3-thiazinyl, piperazinyl, triazinyl, 3- or 4-pyridazinyl, pyrazinyl and N-oxido-3- or 4-pyridazinyl; dicyclic or tricyclic condensed cyclic group (preferably a group formed by condensation of the above-mentioned 5- to 6-membered cyclic group with one or two of the 5- to 6-membered cyclic groups optionally containing, besides carbon atom, 1 to 4 hetero atoms selected from oxygen atom, sulfur atom and nitrogen atom), as exemplified by indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl and phenoxazinyl. Among others, a 5- to 7-membered heterocyclic group having 1 to 3 hetero-atoms selected from nitrogen atom, oxgen atom and sulfur atom is preferable.

Examples of the substituent, which the “heterocyclic group” of this “optionally substituted heterocyclic group” may optionally have, include halogen atoms (e.g. fluorine, chlorine, bromine and iodine), lower alkyl groups (e.g. $C_{1-6}$ alkyl groups such as methyl, ethyl, propyl, isopropyl, butyl, isobutyl, sec-butyl, tert-butyl, pentyl and hexyl), cycloalkyl groups (e.g. $C_{3-6}$ cycloalkyl groups such as cyclopropyl, cyclobutyl, cyclopentyl and cyclohexyl), lower alkynyl groups (e.g. $C_{2-6}$ alkynyl groups such as ethynyl, 1-propynyl and propargyl), lower alkenyl groups (e.g. $C_{2-6}$ alkenyl groups such as vinyl, allyl, isopropenyl, butenyl and isobutenyl), aralkyl groups (e.g. $C_{7-11}$ aralkyl groups such as benzyl, α-methylbenzyl and phenethyl), aryl groups (e.g. $C_{6-10}$ aryl groups such as phenyl and naphthyl, preferably phenyl group), lower alkoxy groups (e.g. $C_{1-6}$ alkoxy groups such as methoxy, ethoxy, propoxy, isopropoxy, butoxy, isobutoxy, sec-butoxy and tert-butoxy), aryloxy groups (e.g. $C_{6-10}$ aryloxy groups such as phenoxy), lower alkanoyl groups (e.g. $C_{1-6}$ alkanoyl groups such as formyl, acetyl, propionyl, butyryl and isobutyryl), benzoyl group, naphthoyl group, lower alkanoyloxy groups (e.g. $C_{1-6}$ alkanoyloxy groups such as formyloxy, acetyloxy, propionyloxy, butyryloxy and isobutyryloxy), arylcarbonyloxy groups (e.g. $C_{6-10}$ aryl-carbonyloxy groups such as benzoyloxy and naphthoyloxy), carboxyl group, lower alkoxycarbonyl groups (e.g. $C_{1-6}$ alkoxycarbonyl groups such as methoxycarbonyl, ethoxycarbonyl, propoxycarbonyl, isopropoxycarbonyl, butoxycarbonyl, isobutoxycarbonyl and tertbutoxycarbonyl), aralkyloxycarbonyl groups (e.g. $C_{7-11}$, aralkyloxycarbonyl groups such as benzyloxycarbonyl), carbamoyl group, mono-, di- or tri-halogeno-lower alkyl groups (e.g. mono-, di- or tri-halogeno-$C_{1-4}$ alkyl groups such as chloromethyl, dichloromethyl, trifluoromethyl and 2,2,2-trifluoroethyl), oxo group, amidino group, imino group, amino group, mono-lower alkylamino groups (e.g. mono-$C_{1-4}$ alkylamino groups such as methylamino, ethylamino, propylamino, isopropylamino and butylamino), di-lower alkylamino groups (e.g. di-$C_{1-4}$ alkylamino groups such as dimethylamino, diethylamino, dipropylamino, diisopropylamino and dibutylamino), 3- to 6-membered cyclic amino groups optionally containing, besides carbon atom and one nitrogen atom, one to three hetero atoms selected from oxygen atom, sulfur atom and nitrogen atom (e.g. 3- to 6-membered cyclic amino groups such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl and N-ethylpiperazinyl), alkylenedioxy group (e.g. $C_{1-3}$ alkylenedioxy groups such as methylenedioxy and ethylenedioxy), hydroxyl group, nitro group, cyano group, mercapto group, sulfo group, sulfino group, phosphono group, sulfamoyl group, monoalkylsulfamoyl group (e.g. $C_{1-6}$ monoalkylsulfamoyl groups such as N-methylsulfamoyl, N-ethylsulfamoyl, N-propylsulfamoyl, N-isopropylsulfamoyl and N-butylsulfamoyl), dialkylsulfamoyl group (e.g. di-$C_{1-6}$ alkylsulfamoyl groups such as N,N-dimethylsulfamoyl, N,N-diethylsulfamoyl, N,N-dipropylsulfamoyl and N,N-dibutylsulfamoyl), alkylthio group (e.g. $C_{1-6}$ alkylthio groups such as methylthio, ethylthio, propylthio, isopropylthio, butylthio, sec-butylthio and tert-butylthio), arylthio group (e.g. $C_{6-10}$ arylthio groups such as phenylthio, naphthylthio), lower alkylsulfinyl groups (e.g. $C_{1-6}$ alkylsulfinyl groups such as methylsulfinyl, ethylsulfinyl, propylsulfinyl and butylsulfinyl), arylsulfinyl group (e.g. $C_{6-10}$ arylsulfinyl groups such as phenylsulfinyl and naphthylsulfinyl), lower alkylsulfonyl groups (e.g. $C_{1-6}$ alkylsulfonyl groups such as methylsulfonyl, ethylsulfonyl, propylsulfonyl and butylsulfonyl) and arylsulfonyl group (e.g. $C_{6-10}$ arysulfonyl groups such as phenylsulfonyl and naphthylsulfonyl).

The "heterocyclic group" of the "optionally substituted heterocyclic group" may have 1 to 5, preferably 1 to 3, of the above-described substituents at any possible position. When the number of the substituents is two or more, they may be the same one or different from one another.

The term "optionally substituted amino group" used in this specification means amino group which may optionally have, as the substituents, one or two of the above-mentioned "optionally substituted hydrocarbon group" for example. Preferable examples of the substituents, which this "amino group" may optionally have, include an optionally substituted $C_{1-6}$ alkyl group and an optionally substituted $C_{6-10}$ aryl group. The substituents of the alkyl or aryl group are, for example, the same substituents which above-mentioned "hydrocarbon group" may optionally have.

The term "substituted hydroxyl group" used in this specification means the hydroxyl group which have, in place of the hydrogen atom of the hydroxyl group, one "optionally substituted hydrocarbon group" mentioned above. Preferable examples of "substituted hydroxyl group" include hydroxyl group substituted with one lower alkyl group. Examples of the "lower alkyl group" includes $C_{1-6}$ alkyl groups such as methyl, ethyl, propyl, isopropyl, butyl, isobutyl, sec-butyl and tertbutyl. The substituents which "lower alkyl group" may optionally have is, for example, the same ones as the above-mentioned "hydrocarbon group" may optionally have.

"Lower alkyl group" of the term "optionally substituted lower alkyl group" used in this specification includes, for example, $C_{1-6}$ alkyl groups such as methyl, ethyl, propyl, isopropyl, butyl, isobutyl, sec-butyl and tert-butyl, which may optionally have 1 to 3 substituents which, for example, the above-mentioned "hydrocarbon group" may optionally have.

"Spiro ring" of the term "optionally substituted spiro ring" used in this specification includes, for example, 3- to 8-membered ring formed by $R^1$ and $R^2$ combinedly taking the adjacent carbon atom as the spiro atom, as exemplified by a lower cycloalkane (e.g. $C_{3-8}$ cycloalkane such as cyclopropane, cyclobutane, cyclopentane and cyclohexane) and a lower cycloalkene (e.g. $C_{3-8}$ cycloalkene such as cyclopropene, cyclobutene, cyclohexene). $C_{3-8}$ cycloalkane is preferable.

The substituents and its number which "spiro ring" may optionally have are, for example, the same ones as the above-mentioned "heterocyclic group" may optionally have. The "spiro ring" may condense with aromatic rings, for example, 6-membered aromatic rings such as benzene and pyridine.

The term "substituted benzene ring" used in this specification means benzene rings which have, at any possible position, one to three substituents selected from halogen atoms (e.g. fluorine, chlorine, bromine and iodine), optionally substituted hydrocarbon groups, substituted hydroxyl groups (preferably, optionally substituted lower ($C_{1-6}$) alkoxy groups such as methoxy, ethoxy, propoxy and isopropoxy), hydroxyl group, optionally substituted amino group, amido groups (e.g. $C_{1-6}$acylamino groups such as acetamido), and lower alkylenedioxy groups (e.g. $C_{1-6}$ alkylenedioxy groups such as methylenedioxy, ethylenedioxy). As these "optionally substituted hydrocarbon group", "substituted hydroxyl group" and "optionally substituted amino group", the same ones as the above-mentioned are used. When the number of the substituents is two or more, they may be the same one or different from one another. Preferable examples of the above-mentioned "substituted benzene ring" include benzene rings having 1 to 3 substituents selected from halogen atoms (e.g. fluorine and chlorine), $C_{1-6}$ alkyl groups (e.g. methyl and ethyl), $C_{1-6}$ alkoxy groups (e.g. methoxy and ethoxy) which may have $C_{6-10}$ aryl group, hydroxyl group and mono-$C_{1-6}$ alkylamino group, especially preferable one being, for example, benzene ring substituted with one, for example, $C_{1-6}$ alkoxy group (e.g. methoxy).

The term "optionally substituted benzene ring" used in this specification includes, for example, the benzene ring which may optionally have 1 to 3 substituents which the above-mentioned "substituted benzene ring" has.

In the above formulae, $R^1$ and $R^2$ are respectively a hydrogen atom, an optionally substituted hydrocarbon group or an optionally substituted heterocyclic group. $R^1$ and $R^2$ may form an optionally substituted spiro ring together with the adjacent carbon atom. Each of $R^1$ and $R^2$ is preferably a hydrogen atom, a lower alkyl group (e.g. a $C_{1-6}$ alkyl group such as methyl, ethyl, propyl and isopropyl) or an aryl group (e.g. a $C_{6-10}$ aryl group such as phenyl, 1-naphthyl and 2-naphthyl), especially a hydrogen atom and a lower alkyl group. And, the case where $R^1$ and $R^2$ combinedly form, taken together with the adjacent carbon atom, a group which may be condensed with an aromatic ring, for example, 6-membered aromatic ring such as benzene, of, for example, the following is preferable.

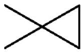 , 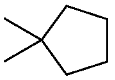 , 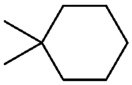

Among others, $R^1$ and $R^2$ are preferably a hydrogen atom, respectively.

In the above formulae, $R^3$ is an optionally substituted hydrocarbon group, an optionally substituted amino group, a substituted hydroxyl group or an optionally substituted heterocyclic group.

Preferable examples of "hydrocarbon group" of "an optionally substituted hydrocarbon group" shown by $R^3$ include alkyl groups (e.g. $C_{1-6}$ alkyl groups such as methyl, ethyl, propyl and isopropyl), alkenyl groups (e.g. $C_{2-6}$ alkenyl groups such as vinyl), alkynyl groups (e.g. $C_{2-6}$ alkynyl groups such as ethynyl), cycloalkyl groups (e.g. $C_{3-6}$ cycloalkyl groups such as cyclopropyl, cyclobutyl, cyclopentyl and cyclohexyl) and aryl groups (e.g. $C_{6-14}$ aryl groups such as phenyl). Among others, alkyl groups (e.g. $C_{1-6}$ alkyl groups such as methyl) and cycloalkyl groups (e.g. $C_{3-6}$ cycloalkyl groups such as cyclopropyl) are preferably used. The "alkyl group", "alkenyl group", "alkynyl group", "cycloalkyl group" and "aryl group" may optionally have, for example, 1 to 5, preferably 1 to 3 substituents, which the above-mentioned "hydrocarbon group" may optionally have, (preferably halogen atoms such as fluorine).

Preferable examples of the substituents of "optionally substituted amino group" shown by $R^3$ include one or two of optionally substituted lower alkyl groups and optionally substituted aryl groups. Especially, one lower alkyl group which may optionally have substituent is used. Examples of the "lower alkyl group" include $C_{1-6}$ alkyl groups such as methyl, ethyl, propyl, isopropyl, butyl, isobutyl, sec-butyl and tert-butyl. The "lower alkyl group" may optionally have, for example, 1 to 3 substituents which the above-mentioned "hydrocarbon group" may optionally have. Examples of the "aryl group" include $C_{6-10}$ aryl groups such as phenyl group. The "aryl group" may have, for example, 1 to 5, preferably 1 to 3 substituents, which the above-mentioned "hydrocarbon group" may optionally have, (preferably halogen atoms such as fluorine and chlorine, and $C_{1-6}$ alkoxy groups such as methoxy and ethoxy). Examples of the "optionally substituted amino group" include phenylamino groups substituted with 1 to 3 lower alkoxy groups (e.g. methoxy) and amino groups mono-substituted with a lower alkyl group (e.g. methyl, ethyl, propyl, isopropyl, butyl, isobutyl, sec-butyl and tert-butyl). Among others, a mono-$C_{1-6}$ alkyl amino group is preferable.

Examples of the substituents which the "substituted hydroxyl group" shown by $R^3$ may have include an optionally substituted lower alkyl group. Examples of the "lower alkyl group" include $C_{1-6}$ alkyl groups such as methyl, ethyl, propyl, isopropyl, butyl, isobutyl, sec-butyl and tert-butyl. The "lower alkyl group" may optionally have, for example, 1 to 3 substituents which the above-mentioned "hydrocarbon group" may optionally have. Preferable examples of "substituted hydroxyl group" include optionally substituted lower alkoxy groups (e.g. $C_{1-6}$ alkoxy groups such as methoxy, ethoxy, propoxy, isopropoxy and butoxy). Examples of the substituents of the "lower alkoxy groups" include the substituents which the above-mentioned "hydrocarbon group" may optionally have.

Preferable examples of "heterocyclic group" of "optionally substituted heterocyclic group" shown by $R^3$ include 5- or 6-membered heterocyclic group containing, besides carbon atom, 1 to 3 hetero atoms selected from nitrogen atom, oxygen atom and sulfur atom, as exemplified by 1-, 2- or 3-pyrrolidinyl, 2- or 4-imidazolinyl, 2-, 3- or 4-pyrazolidinyl, piperidinyl, 2-, 3- or 4-piperidyl, 1- or 2-piperazinyl, morpholino, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl or 3-isooxazolyl. Especially, 6-membered nitrogen-containing heterocyclic groups such as pyridyl are preferably used.

Preferable examples of substituents of "optionally substituted heterocyclic group" shown by $R^3$ include, for example, halogen atoms, $C_{1-6}$ alkyl groups, $C_{1-6}$ alkoxy groups and aralkyloxycarbonyl groups.

Preferable examples of $R^3$ include (i) optionally substituted lower alkyl groups, (ii) optionally substituted lower cycloalkyl groups, (iii) optionally substituted lower alkenyl groups, (iv) optionally substituted aryl groups (v) optionally substituted lower alkylamino groups, (vi) optionally substituted arylamino groups, (vii) optionally substituted 5- or 6-membered nitrogen-containing heterocyclic groups, or (viii) optionally substituted lower alkoxy groups. Preferable examples of the "lower alkyl group" include $C_{1-6}$ alkyl groups such as methyl, ethyl, propyl, isopropyl, butyl, pentyl and hexyl. Preferable examples of the "lower cycloalkyl group" include $C_{3-6}$ cycloalkyl groups such as cyclopropyl, cyclobutyl, cyclopentyl and cyclohexyl. Preferable examples of the "lower alkenyl group" include $C_{2-6}$ alkenyl groups such as vinyl, 1-propenyl and butenyl. Preferable examples of the "aryl group" include $C_{6-10}$ aryl groups such as phenyl, 1-naphthyl and 2-naphthyl. Preferable examples of the "lower alkylamino group" include mono- or di-$C_{1-6}$ alkylamino groups such as methylamino, ethylamino, propylamino, butylamino, tert-butylamino, dimethylamino, diethylamino and methylethylamino. Preferable examples of the "arylamino group" include $C_{6-10}$ arylamino groups such as phenylamino. Preferable examples of the "5- or 6-membered nitrogen-containing heterocyclic group" include 5- or 6-membered nitrogen-containing heterocyclic groups such as 2-, 3- or 4-pyridyl. Preferable examples of the "lower alkoxy group" include $C_{1-6}$ alkoxy groups such as methoxy, ethoxy, propoxy and isopropoxy. The substituents which these groups may optionally have is, for example, 1–5 of those which the above-mentioned "hydrocarbon group" may optionally have. Among others, i) $C_{1-6}$ alkyl groups optionally substituted by halogen atoms or $C_{1-6}$ alkoxy groups, ii) $C_{3-6}$ cycloalkyl groups, iii) $C_{2-6}$ alkenyl groups, iv) $C_{6-10}$ aryl groups optionally substituted by a) $C_{1-6}$ alkoxy, b) nitro, c) halogeno-$C_{1-6}$ alkyl-carbonylamino or d) halogen atoms, v) mono- or di-$C_{1-6}$ alkylamino groups, vi) $C_{6-10}$ arylamino groups optionally substituted by 1 to 3 $C_{1-6}$ alkoxy, vii) 6-membered nitrogen-containing heterocyclic groups optionally substituted by $C_{7-11}$ aralkyloxycarbonyl and viii) $C_{1-6}$ alkoxy groups are preferably used. Especially, for example, optionally halogenated $C_{1-6}$ alkyl groups (e.g. methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl), $C_{3-6}$ cycloalkyl groups (e.g. cyclopropyl, cyclobutyl, cyclopentyl and cyclohexyl) and mono- $C_{1-6}$ alkylamino groups (e.g. methylamino, ethylamino, propylamino, isopropylamino, butylamino and tert-butylamino) are used. Typically, optionally halogenated $C_{1-6}$ alkyl groups and mono- $C_{1-6}$ alkylamino groups, especially, halogenated $C_{1-3}$ alkyl groups are preferred.

In the above formulae, $R^4$ is a hydrogen atom or an optionally substituted lower alkyl group. $R^4$ is preferably a hydrogen atom or a $C_{1-4}$ alkyl group (e.g. methyl), especially a hydrogen atom.

In the above-mentioned formulae, ring A is a substituted benzene ring, and ring $A^1$ is an optionally substituted benzene ring. Preferable examples of ring A and ring $A^1$ include

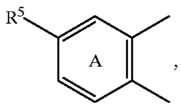
,
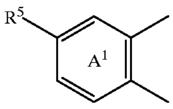

wherein $R^5$ is an optionally substituted lower alkoxy group (e.g. $C_{1-6}$ alkoxy group such as methoxy and ethoxy). Preferable examples of $R_5$ include $C_{1-6}$ alkoxy groups optionally substituted by $C_{6-10}$ aryl groups.

Especially, $C_{1-6}$ alkoxy groups (e.g. methoxy) are preferable.

Preferable examples of

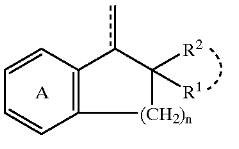

include

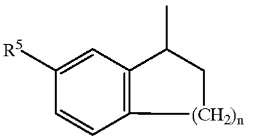

wherein symbols are of the same meaning as defined above.

m and n independently denote an integer of 1 to 4, preferably 1 to 3. Preferably, m is 1 or 2, especially 1. Preferably, n is 1 or 2, especially 1.

In the above formulae, ......... means a single bond or double bond, preferably, single bond, and ∿∿∿ means, when ......... is double bond, E-isomer, Z-isomer or a mixture of them.

Examples of the compound (I) of the present invention n include those having the following structural formulae.

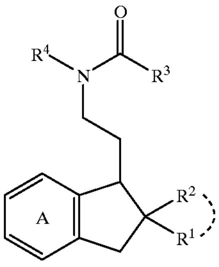
,
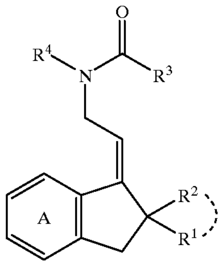
,
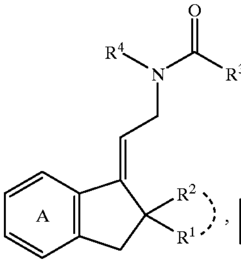
,
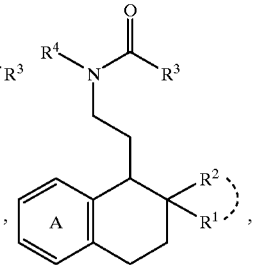
,
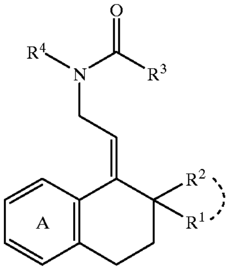
,
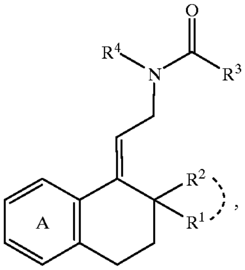
,
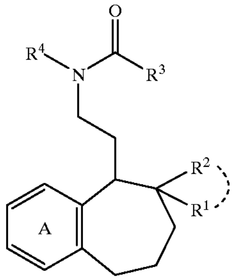
,
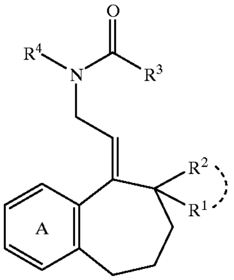
,
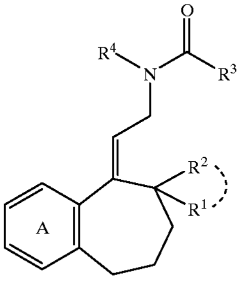

wherein symbols are of the same meaning as defined in the foregoing.

Preferable example of the compound (I) include the compound of the formula:

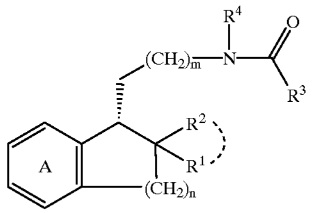

wherein all symbols are of the same meaning as defined above. $R^1$ and $R^2$ are preferably hydrogen.

More preferably, in the above formulae, (i) the compound in which m is 1, n is 2 and ......... is a single bond, (ii) the compound in which m is 1, n is 2 and ......... is a double bond, (iii) the compound in which m is 1 or 2, n is 1 and ......... is a single bond, and (iv) the compound in which m is 1, n is 3 and ......... is a double bond.

In the compound (I) and (Ia), preferable is the compound wherein $R^1$ and $R^2$ are respectively a hydrogen atom, a lower alkyl group or $C_{6-10}$ aryl group or $R^1$ and $R^2$ may combinedly form, taken together with the adjacent carbon atom, a $C_{3-8}$ spiro ring which may be condensed with a 6-membered aromatic ring; $R^3$ is (i) optionally substituted lower alkyl groups, (ii) optionally substituted lower cycloalkyl groups, (iii) optionally substituted lower alkenyl groups, (iv) optionally substituted aryl groups (v) optionally substituted lower alkylamino groups, (vi) optionally substituted arylamino groups, (vii) optionally substituted 5- or 6-membered nitrogen-containing heterocyclic groups, or (viii) optionally substituted lower alkoxy groups, the substituents which these groups may optionally have is 1 to 5 of those which the above-mentioned "hydrocarbon group" may optionally have;

$R^4$is a hydrogen atom or a lower alkyl; ring A or ring $A^1$ is a substituted benzene ring;

m is 1 or 2; and n is integer of 1 to 3.

More preferable is the compound wherein $R^1$ and $R^2$ are respectively a hydrogen atom, a $C_{1-3}$ alkyl group or $C_{6-10}$ aryl group;

$R^3$ is i) $C_{1-6}$ alkyl groups optionally substituted by halogen atoms or $C_{1-6}$ alkoxy, (ii) $C_{3-6}$ cycloalkyl groups, (iii) $C_{2-6}$ alkenyl groups, iv) $C_{6-10}$ aryl groups optionally substituted by a) $C_{1-6}$ alkoxy, b) nitro, c) halogeno-$C_{1-6}$ alkylcarbonylamino or d) halogen, v) mono- or di-$C_{1-6}$ alkylamino groups, vi) $C_{6-10}$ arylamino groups optionally substituted by 1 to 3 $C_{1-6}$ alkoxy, vii) 6-membered nitrogen-containing heterocyclic groups optionally substituted by $C_{7-11}$ aralkyloxy-carbonyl or viii) $C_{1-6}$ alkoxy groups;

$R^4$ is a hydrogen atom or a $C_{14}$ alkyl group; ring A or ring $A^1$ is a benzene ring substituted by a lower alkoxy group which may have a $C_{6-10}$ aryl group; and m and n are respectively 1.

Especially, the compound wherein $R^1$, $R^2$ and $R^4$ are respectively a hydrogen atom; $R^3$ is a $C_{1-6}$ alkyl group optionally substituted by halogen atoms or mono-$C_{1-6}$ alkylamino group; ring A or ring $A^1$ is a benzene ring substituted by a $C_{1-3}$ alkoxy group; and m and n are respectively 1, is preferable.

Preferable examples of the object compound (I) of the present invention and compound (Ia) include (E)-1-[2-(acetylamino)ethylidene]-7-methoxy-1,2,3,4tetrahydronaphthalene, (E)-7-methoxy-1-[2-(trifluoroacetylamino)ethylidene]-1,2,3,4-tetrahydronaphthalene, (E)-3-1-[2-

(cyclopropylcarbonylamino)ethylidene]-7-methoxy 1,2,3,4-tetrahydronaphthalene, 1-[2-(acetylamino)ethyl]-6-methoxyindan, 1-[2-(trifluoroacetylamino)ethyl]-6-methoxyindan, 1-[2-(cyclopropylcarbonylamino)ethyl]-6-methoxyindan, 1-[2-(propionylamino)ethyl]-6-methoxyindan, 1-[2-(isobutylylamino)ethyl]-6-methoxyindan, (E)-1-[2-(acetylamino)ethylidene]-6-methoxyindan, (E)-1-[2-(trifluoroacetylamino)ethylidene]-6-methoxyindan, (E)-1-[2-(cyclopropylcarbonylamino) ethylidene]-6-methoxyindan, 1-[2-(acetylamino)ethyl]-7-methoxy-1,2,3,4-tetrahydronaphthalene, 7-methoxy-1-[2-(trifluoroacetylamino)ethyl]-1,2,3,4 -tetrahydronaphthalene and 1-[2-(cyclopropylcarbonylamino)ethyl]-7-methoxy-1,2,3,4-tetrahydronaphthalene.

More preferable is (S)-1-[2-(acetylamino)ethyl]-6-methoxyindan, (S)-1-[2-(trifluoroacetylamino)ethyl]-6-methoxyindan, (S)-1-[2-(cyclopropylcarbonylamino)ethyl]-6-methoxyindan, (S)-1-[2-(propionylamino)ethyl]-6-methoxyindan, (S)-1-[2-(isobutyrylamino)ethyl]-6-methoxyindan, (S)-1-[2-(acetylamino)ethyl]-7-methoxy-1,2,3,4-tetrahydronaphthalene, (S)-7-methoxy-1-[2-(trifluoroacetylamino)ethyl]-1,2,3,4-tetrahydronaphthalene and (S)-1-[2-(cyclopropylcarbonylamino)ethyl]-7-methoxy-1,2,3,4-tetrahydronaphthalene.

Examples of the salts of the compound (I) and (Ia) include pharmaceutically acceptable salts, which are exemplified by salts with inorganic bases, salts with organic bases, salts with inorganic acids, salts with organic acids and salts with basic or acidic amino acids. Preferable salts with inorganic bases include alkali metal salts such as sodium salt and potassium salt, alkaline earth metal salts such as calcium salt and magnesium salt as well as aluminum salt and ammonium salt. Preferable salts with organic bases include salts with, for example, trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Preferable salts with inorganic acids include salts with, for example, hydrochloric acid, hydrobromic acid, nitric acid, sulfuric acid and phosphoric acid. Preferable salts with organic acids include salts with, for example, formic acid, acetic acid, trifluoroacetic acid, phthalic acid fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with, for example, arginine, lysine and ornithine. Preferable salts with acidic amino acids include salts with, for example, aspartic acid and glutamic acid.

Among them, pharmaceutically acceptable salts are preferable, which are exemplified by, when the compound (I) or (Ia) has a basic functional group, salts with inorganic acids such as hydrochloric acid, hydrobromic acid, nitric acid, sulfuric acid or phosphoric acid, and, salts with organic acids such as acetic acid, phthalic acid, fumaric acid, tartaric acid, maleic acid, citric acid, succinic acid, methanesulfonic acid and p-toluenesulfonic acid, and, when the compound (I) or (Ia) has an acidic functional group, alkali metal salts such as sodium salt and potassium salt, alkaline earth metal salts such as calcium salt and magnesium salt, and ammonium salt.

On the production of the compound (I) or salts thereof of this invention (hereinafter simply referred to as compound (I)) and the compound (Ia) or salts thereof (hereinafter simply referred to as compound (Ia)), the following description is given.

The compound (I) and compound (Ia) can be produced in accordance with, for example, the reaction scheme-1 or 2. These reaction schema are shown below.

All symbols of the compounds in the reaction schema are of the same meaning as defined above.

Reaction scheme - 1

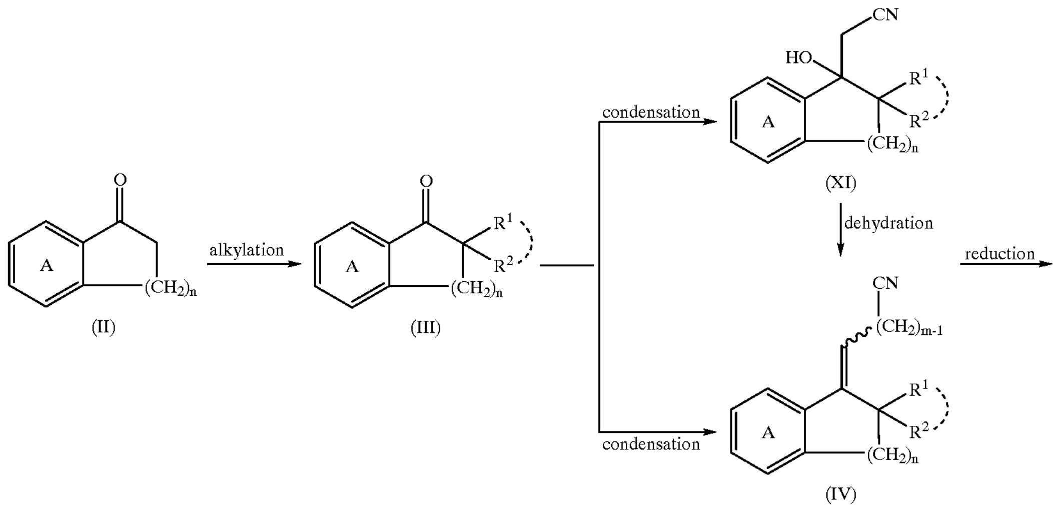

(II) (III) (XI) (IV)

-continued
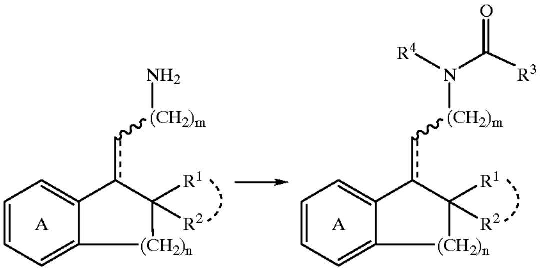
(V) (I)
Reaction scheme-2
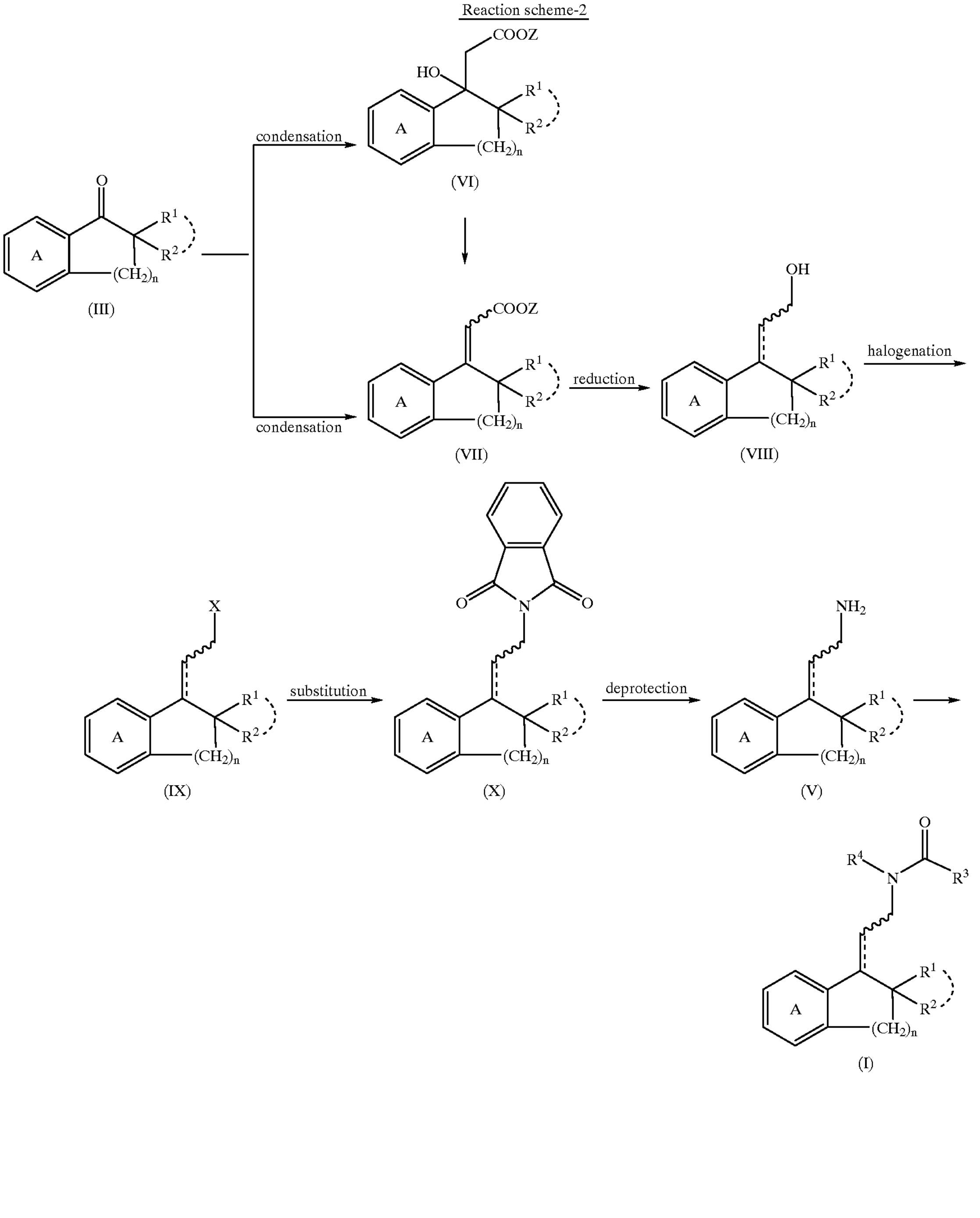
(III) (VI) (VII) (VIII) (IX) (X) (V) (I)

In the present invention, the compound (II) can be produced by a per e known method or a method analogous thereto, for example, by the method described in Journal of the Chemical Society, (C), P.990 (1966).

The compound (III) can be produced by a per se known method of a method analogous thereto, for example, by methods described in Journal of Organic Chemistry, 26, P.27 (1961) and 55, P.1874 (1990), Journal of the American Chemical Society, 105, 3992 (1983), Journal of the Chemical Society Perkin Trans. I, 3399 (1988), Journal of the Chemical Society (c), P.217 (1969) and Liebigs Annalen Chemie, P.263 (1987), or methods analogous thereto.

The compound (V) can be produced by a per se known method of an analogous method thereto, for example, the method described in Canadian Journal of Chemistry 53, P.3681 (1975).

The compound (IV) can be produced by allowing phosphonate carboanion, produced by processing alkylphosphonic acid diester with a base, to react with the compound (III) as a configuration isomer singly or a mixture of E- and Z-isomers. Relative to 1 mol. of the compound (III), about 1 to 3 mol., preferably about 1 to 1.5 mol., of alkyl phosphonic acid diester is used. As the base, is used sodium hydride, sodium amide or metal alcoholate, for example, in an amount of about 1 to 3 mol., preferably about 1 to 1.5 mol. relative to 1 mol. of alkylphosphonic acid diester. This reaction is conducted advantageously in the presence of an inert solvent. As the solvent, any one can be used unless it hampers the proceeding of the reaction. Preferable examples of the solvent include alcohols such as methanol, ethanol and propanol, aromatic hydrocarbons such as benzene, toluene and xylene, ethers such as tetrahydrofuran, dioxane, 1,2-dimethoxyethane, diethyl ether and diisopropyl ether, and amides such as N, N-dimethylformamide, N, N-dimethylacetamide and hexamethylphosphoramide, and sulfoxides such as dimethyl sulfoxide. The reaction time ranges usually from 1 to 24 hours, preferably 1 to 6 hours. The reaction temperatures ranges usually from 0 to 150° C., preferably from 0 to 100° C. And, the compound (IV) can also be produced by allowing carbanion, produced by processing acetonitrile with a base, to react with the compound (III) and by subjecting the reaction mixture to dehydration. Acetonitrile is used in an amount of about 1 to 1.5 mol., preferably equimol. relative to 1 mol. of the compound (III). As the base, lithium amide (e.g. lithium diisopropylamide and lithium 1,1,1,3,3,3-hexamethyldisilazide) is used in an amount of about 1 to 1.5 mol., preferably about 1 to 1.1 mol. relative to 1 mol. of the compound (III). This reaction is advantageously conducted in the presence of an inert solvent. As the solvent, any one can be used if only the reaction proceeds, and ethers such as tetrahydrofuran, dioxane, 1,2-dimethoxyethane, diethyl ether and diisopropyl ether for example, are preferable. The reaction time ranges usually from 30 minutes to 2 hours. The reaction temperature ranges usually from −78 to 50° C., preferably from −78 to 0° C. As the catalyst for dehydration, for example, an acid (e.g. hydrochloric acid, sulfuric acid, phosphoric acid, potassium hydrogen sulfate, oxalic acid, p-toluenesulfonic acid, boron trifluoride ether complex), and a base (e.g. sodium hydroxide and potassium hydroxide) are used. The dehydration also proceeds by using, for example, a dehydrating agent such as N,N-dicyclohexylcarbodiimide, or, alumina, sodium dioxide, phosphorus oxychloride, thionyl chloride, iodine, anhydrous copper sulfate and methanesulfonyl chloride. It is advantageous that this reaction is conducted in the absence of solvent or in the presence of a solvent inert to the reaction. As the solvent, any one can be used so long as the reaction proceeds. Preferable examples of the solvent include alcohols such as methanol, ethanol and propanol, ethers such as tetrahydrofuran, dioxane, 1,2-dimethoxyethane, diethyl ether and diisopropyl ether, and aromatic amines such as pyridine. The reaction time ranges usually from 30 minutes to 6 hours, preferably from 30 minutes to 2 hours. The reaction temperature ranges usually from 0 to 300° C., preferably from 10 to 100° C. The mixture of isomers of the compound (IV) can be isolated and purified by conventional separating methods such as recrystallization, distillation and chromatography to give a mixture of E- and Z-isomers or a simple substance of E-isomer or Z-isomer, respectively.

The compound (V) can be produced by subjecting the compound (IV) or a salt thereof to reduction. This reduction is conducted by hydrogenation using a metal hydride (e.g. aluminum hydride or diisobutylaluminum hydride), a metal hydride complex (e.g. lithium aluminum hydride or sodium borohydride) or a Raney nickel catalyst or a Raney cobalt catalyst. A metal hydride is used in an amount of about 0.5 to 10 mol., preferably about 1.0 to 3.0 mol., relative to 1 mol. of the compound (IV). A metal hydride complex is used in an amount of about 0.5 to 10 mol., preferably 1.0 to 3.0 mol., relative to 1 mol of compound (IV). Raney catalyst is used in an amound of 10 to 1000 w/w %, preferably 50 to 300 w/w % of the compound (IV). It is advantageous that this reaction is conducted by using an inert solvent. As the solvent, any one can be employed so long as it does not hamper the proceeding of reaction. Preferable examples of the solvent include alcohols such as methanol, ethanol and propanol, aliphatic hydrocarbons such as cyclohexane and hexane, carboxylic acids such as formic acid and acetic acid, ethers such as tetrahydrofuran, dioxane, 1,2-dimethoxyethane, diethyl ether and diisopropyl ether, and amides such as N,N-dimethylformamide, N,N-dimethylacetamide and hexamethylphosphoramide. When a Raney nickel catalyst or a Raney cobalt catalyst is used, it is preferable, in some instances, to supplement, for example, ammonia or hydrazine to suppress undesirable side reactions. The reaction time ranges usually from 1 to 24 hours, preferably from 1 to 6 hours, while varying with the activity and amount of the reducing agent then employed. The reaction temperature ranges usually from 0 to 100° C., preferably from 20 to 50° C. The pressure ranges usually from 1 to 100 kgf/$cm^2$. The compound (V) can be isolated and refined by conventional separating methods, for example, distillation and chromatography to give a mixture of E- and Z-isomers or a simple substance of E-isomer or Z-isomer, respectively. And, by employing adequate conditions, the double bond can be reduced to single bond simultaneously with the reduction of nitrile. Further, it is possible that merely the nitrile of either one of E-isomer or Z-isomer in their mixture is reduced selectively to give the amine compound of either one of E-isomer or Z-isomer selectively.

The compound (I) is produced by allowing the compound (V) to react with carboxylic acid represented by $R^3COOH$ ($R^3$ is of the same meaning as defined above) or salt or a reactive derivative thereof. Examples of the salts include alkali metal salts such as sodium salt and potassium salt, alkaline earth metal salts such as calcium salt and magnesium salt, ammonium salt and organic bases such as trimethylamine, triethylamine, pyridine and picoline. Examples of the reactive derivatives of carboxylic acid include acid halogenides (e.g. acid chlorides and acid bromides), acid amides (e.g. imidazolides), acid anhydrides, acid azides, active esters (e.g. N-phthalimidoester and N-succinimidoester. And, instead of using the reactive derivative, the carboxylic acid may be allowed to react directly with the compound (V). In this case, it is preferable to allow the reaction to proceed in the presence of a coupling reagent such as N,N'-dicyclohexylcarbodiimide or 1-ethyl-3-(3-dimethylaminopropyl)carbodiimide hydrochloride (WSC). The carboxylic acid or a reactive derivative thereof is used in an amount ranging usually from about 1 to 3 mol., preferably from about 1 to 1.2 mol. relative to 1 mol. of the compound (V). It is advantageous that this reaction is conducted in the presence of an inert solvent. As the solvent, any one can be used so long as it does not hamper the proceeding of the reaction. Preferable examples of the solvent include ethers such as tetrahydrofuran, dioxane, 1,2-dimethoxyethane, diethyl ether and diisopropyl ether, amides such as N,N-dimethylformamide, N,N-dimethylacetamide and hexamethylphosphoramide, and halogenohydrocarbons such as dichloromethane, chloroform, tetrachloromethane and 1,2-dichloroethane. When an acid halogenide is used as the reactive derivative of carboxylic acid, it is preferable that an amine, for example, triethylamine, pyridine or 4-dimethylaminopyridine is previously added to the reaction system. While the reaction time varies with the reagent or solvent then employed, it ranges usually from 30 minute to 24 hours, preferably from 30 minutes to 4 hours. The reaction temperature ranges usually from 0 to 100° C., preferably from 0 to 70° C. When the compound (I) is a urea compound, it is also produced by subjecting the compound (V) to condensation with an isocyanate compound represented by $R^{3'}N{=}C{=}O$ ($R^{3'}$has the same meaning as $R^3$ defined above except —NH.). Usually, 1 to 1.5 mol., preferably equimol. of an isocyanate compound is used relative to 1 mol. of the compound (V). As the solvent, any one can be used so long as it does not hamper the proceeding of reaction. Preferable examples of the solvent include aromatic hydrocarbons such as benzene, toluene and xylene, ethers such as tetrahydrofuran, dioxane, 1,2-dimethoxyethane, diethyl ether and diisopropyl ether, amides such as N,N-dimethylformamide, N,N-dimethylacetamide and hexamethylphosphoramide, halogenohydrocarbons such as dichloromethane, chloroform, carbon tetrachloride and 1,2-dichloroethane, and ketones such as acetone and methyl ethyl ketone. While the reaction time varies with the reagent and solvent then employed, it ranges usually from 30 minutes to 24 hours, preferably from 30 minutes to 4 hours. The reaction temperature ranges usually from 0 to 100° C., preferably from 0 to 70° C. A mixture of isomers of the compound (I) can be isolated and refined by conventional methods, for example, recrystallization, distillation or chromatography to give a mixture of E- and Z-isomers or a simple substance of E-isomer or Z-isomer, respectively.

The compound (VI) shown in the reaction scheme-2 can be produced by allowing carbanion, which is produced by subjecting a compound represented by $CH_3COOZ$ (Z represents an optionally substituted hydrocarbon group) to processing with a base, to react with the compound (III). The "optionally substituted hydrocarbon group" by shown Z includes, for example, the above-mentioned "optionally substituted hydrocarbon group". Relative to 1 mol. of the compound (III), the compound of $CH_3COOZ$ is used in an amount of about 1 to 1.5 mol., preferably equimol. As the base, lithium amide (e.g. lithium diisopropylamide and lithium 1,1,1,3,3,3-hexamethyldisilazide) is used in an amount of about 1 to 1.5 mol., preferably about 1 to 1.1 mol. relative to 1 mol. of the compound (III). This reaction is advantageously conducted using a solvent inert to the reaction. As the solvent, while any one can be used, so long as it does not hamper the proceeding of reaction, ethers such as tetrahydrofuran, dioxan, diethyl ether and diisopropylether, for example, are preferably used. The reaction time ranges usually from 30 minutes to 6 hours, preferably from 30 minutes to 2 hours. The reaction temperature ranges usually from −78 to 50° C., preferably from −78 to 0° C.

The compound (VII) can be produced by processing the compound (VI) to cause dehydration to proceed. As the catalyst for dehydration, for example an acid (e.g. hydrochloric acid sulfuric acid, phosphoric acid, potassium hydrogen sulfate, oxalic acid, p-toluenesulfonic acid, 10-camphorsulfonic acid and boron trifluoride ether complex) and a base (e.g. sodium R hydroxide and potassium hydroxide) are used. And, depending on cases, dehydration also proceeds by the use of a dehydrating agent such as N,N-dicyclohexylcarbodiimide, or by the use of alumina, sodium dioxide, phosphorus oxychloride, thionyl chloride, iodine, anhydrous copper sulfate and methanesulfonyl chloride. It is advantageous that this reaction is conducted in the absence of solvent or using a solvent inert to the reaction. As the solvent, while any one can be employed, so long as it does not hamper the proceeding of reaction. Preferable examples of the solvent include alcohols such as methanol, ethanol and propanol, ethers such as tetrahydrofuran, dioxane, 1,2-dimethoxyethane, diethyl ether and diisopropyl ether, and aromatic amines such as pyridine. The reaction time ranges usually from 30 minutes to 6 hours, preferably from 30 minutes to 2 hours. The reaction temperature ranges usually from room temperature (10–35° C.) to 300° C., preferably from room temperature to 100° C.

And, the compound (VII) can be produced by allowing phosphonate carbanion, produced by processing alkylphosphonic diester with a base, to react with the compound (III), as the respective isomers singly or a mixture of E- and Z-isomers. Relative to 1 mol. of the compound (III), alkylphosphonic diester is used in an amount of about 1 to 3 mol., preferably about 1 to 1.5 mol. As the base, for example, sodium hydride, sodium amide and metal alcoholate is used in an amount of about 1 to 3 mol., preferably about 1 to 1.5 mol. relative to 1 mol. of alkylphosphonic diester. This reaction is advantageously conducted by the use of an inert solvent. As the solvent, any one can be used, so long as it does not hamper the proceeding of reaction. Preferable examples of the solvent include alcohols such as methanol, ethanol and propanol, aromatic hydrocarbons such as benzene, toluene and xylene, ethers such as tetrahydrofuran, dioxane, 1,2-dimethoxyethane, diethyl ether and diisopropyl ether, and sulfoxides such as dimethylsulfoxide. The reaction time ranges usually from 1 to 24 hours, preferably from 1 to 6 hours. The reaction temperature ranges usually from 0 to 150° C., preferably from 0 to 100° C. A mixture of isomers of the compound (VII) can be isolated and purified by conventional separating methods such as recrystallization, distillation and chromatography to give a mixture of E- and Z-isomers or a simple substance of E-isomer or Z-isomer, respectively.

The compound (VIII) is produced by subjecting the compound (VII) to reduction.

The compound (VIII), in which the ester group is reduced, can be produced by processing the compound (VII) with a metal hydride (e.g. aluminum hydride and diisobutylaluminum hydride) or a metal hydride complex compound (e.g. lithium aluminum hydride and sodium borohydride) in an amount of about 1 to 3 mol., preferably about 1 to 1.2 mol. relative to 1 mol. of the compound (VII). This reaction is advantageously conducted by the use of an inert solvent. As the solvent, any one can be used, so long as it does not hamper the proceeding of reaction. Preferable examples of the solvent include alcohols such as methanol, ethanol and propanol, aromatic hydrocarbons such as benzene, toluene and xylene, aliphatic hydrocarbons such as cyclohexane and hexane, ethers such as tetrahydrofuran, dioxane, 1,2-dimethoxyethane, diethyl ether and diisopropyl ether, and halogenohydrocarbons such as dichloromethane, chloroform, carbon tetrachloride and 1,2-dichloroethane. The reaction time ranges usually from 30 minutes to 12 hours, preferably from 30 minutes to 4 hours. The reaction temperature ranges usually from −20 to 150° C., preferably from −20 to 80° C. A mixture of isomers of the compound (VIII) can be isolated and purified by a conventional separating methods such as recrystallization, distillation and chromatography to give a mixture of E- and Z-isomers or a simple substance of E-isomer or Z-isomer, respectively. The compound (IX) can be produced by allowing a halogenide to react with the compound (VIII). Preferable examples of the halogenide include hydrogen halogenide (e.g. hydrogen bromide and hydrochloric acid), phosphorus halogenide (e.g. phosphorus pentachloride, phosphorus trichloride and phosphorus tribromide), thionyl halogenide (e.g. thionyl chloride and thionyl bromide) and halogenide with phosphine (e.g. carbon tetrabromide or carbon tetrachloride with triphenylphosphine). The halogenide is used in an amount of 0.2 to 5.0 mol., preferably 0.5 to 2.0 mol. relative to 1 mol. of the compound (VIII). Preferable examples of the solvent include aromatic hydrocarbons such as benzene, toluene and xylene, ethers such as tetrahydrofuran, dioxane, 1,2-dimethoxyethane, diethyl ether and diisopropyl ether and halogenohydrocarbons such as dichloromethane, chloroform, carbontetrachloride and 1,2-dichloroethane. The reaction time ranges usually from 30 minutes to 12 hours, preferably from 30 minutes to 3 hours. The reaction temperature ranges usually from room temperature to 150° C., preferably from room temperature to 100° C. A mixture of isomers of the compound (IX) can be isolated and purified by conventional separating methods such as recrystallization, distillation and chromatography to give a mixture of E- and Z-isomers or a simple substance of E-isomer or Z-isomer, respectively.

The compound (X) can be produced by subjecting 1 mol of the compound (IX) to condensation with about 1 to 5 mol., preferably about 1 to 1.2 mol., of potassium phthalimide. The condensation is advantageously conducted, when desired, in the presence of a base, in the absence of a solvent or using an inert solvent. Preferable examples of the base include triethylamine, sodium amide, sodium hydride, sodium alkoxide and lithium diisopropylamide. As the solvent, any one can be used, so long as it does not hamper the proceeding of reaction. Preferable examples of the solvent include alcohols such as methanol, ethanol and propanol, aromatic hydrocarbons such as benzene, toluene and xylene, ethers such as tetrahydrofuran, dioxane, 1,2-dimethoxyethane, diethyl ether and diisopropyl ether, and halogenohydrocarbons such as dichloromethane, chloroform, carbon tetrachloride and 1,2-dichloroethane. The reaction time ranges usually from 30 minutes to 12 hours, preferably from 30 minutes to 4 hours. The reaction temperature ranges usually from −5 to 150° C., preferably from 5 to 80° C. A mixture of isomers of the compound (IX) can be isolated and purified by conventional separating methods such as recrystallization, distillation and chromatography to give a mixture of E- and Z-isomers or a simple substance of E-isomer or Z-isomer, respectively.

The compound (V) can be produced by using, relative to 1 mol. of the compound (X), amines (e.g. methylamine and ethylamine), hydrazines (e.g. hydrazine, phenylhydrazine), alkali sultides (e.g. sodium and potassium), and a mineral acids (e.g. hydrochloric acid and sulfuric acid) in an amount of usually from about 1 to 20 mol., preferably from about 1 to 5 mol. It is advantageous that this reaction is conducted using a solvent inert to the reaction. As the solvent, any one can be used, so long as it does not hamper the proceeding of reaction. Preferable examples of the solvent include alcohols such as methanol, ethanol and propanol, and ethers such as tetrahydrofuran, dioxane, 1,2-dimethoxyethane, diethyl ether and diisopropyl ether. The reaction time ranges usually from 30 minutes to 12 hours, preferably from 30 minutes to 4 hours. The reaction temperature ranges usually from room temperature to 150° C., preferably from room temperature to 100° C. A mixture of isomers of the compound (V) can be isolated and purified by conventional methods such as distillation and chromatography to give a mixture of E- and Z-isomers or a simple substance of E-isomer or Z-isomer, respectively.

The compound (V) can be led to the compound (I) by substantially the same procedure as described in the above-mentioned reaction scheme-1.

And, in each of the reactions described above, when the starting compound has amino group, carboxyl group or hydroxyl group as a substituent, these groups may be protected with a protective group generally used in the field of peptide chemistry. After completion of the reaction, these protective groups may be removed depending on necessity to give the object compound.

Examples of amino-protective groups include formyl group or an optionally substituted $C_{1-6}$ alkyl carbonyl (e.g. acetyl and propionyl), phenylcarbonyl, $C_{1-6}$ alkyl-oxycarbonyl (e.g. methoxycarbonyl and ethoxycarbonyl), phenyloxycarbonyl, $C_{7-10}$ aralkyl-oxycarbonyl (e.g. benzylcarbonyl), trityl and phthaloyl groups. Examples of these substituents include halogen atoms (e.g. fluorine, chlorine, bromine and iodine), $C_{1-6}$ alkyl-carbonyl (e.g. acetyl, propionyl and valeryl) and nitro, and the number of these substituents ranges from about 1 to 3.

Examples of carboxyl-protective groups include optionally substituted $C_{1-6}$ alkyl (e.g. methyl, ethyl, propyl, isopropyl, butyl and tert-butyl), phenyl, trityl and silyl groups. As these substituents, for example, halogen atoms (e.g. fluorine, chlorine, bromine and iodine), formyl, $C_{1-6}$ alkyl-carbonyl (e.g. acetyl, propionyl and butyl carbonyl), $C_{1-6}$ alkyl (e.g. methyl, ethyl and tert-butyl), $C_{6-10}$ aryl (e.g. phenyl and naphthyl) and nitro group, and the number of these substituents ranges from about 1 to 3.

Examples of hydroxyl-protective groups include optionally substituted $C_{1-6}$ alkyl (e.g. methyl, ethyl, propyl, isopropyl, butyl and tert-butyl), phenyl, $C_{7-10}$ aralkyl (e.g. benzyl), formyl, $C_{1-6}$ alkyl-carbonyl (e.g. acetyl and propionyl), phenyloxycarbonyl, $C_{7-11}$ aralkyl-oxycarbonyl (e.g. benzyloxycarbonyl), tetrahydropyranyl, tetrahydrofuranyl and silyl groups.

As these substituents, for example, halogen atoms (e.g. fluorine, chlorine, bromine and iodine), $C_{1-6}$ alkyl, (e.g. methyl, ethyl and tert-butyl) $C_{7-11}$ aralkyl (e.g. benzyl) $C_{6-10}$ aryl (e.g. phenyl and naphthyl) and nitro group are used, and the number of these substituents ranges from about 1 to 4.

For removing these protective groups, a per se known method or analogous methods thereto are employed. For example, methods using acid, base, ultra-violet ray, hydrazine, phenylhydrazine, sodium N-methyl dithiocarbamate, tetrabutylammonium fluoride and palladium acetate or reduction.

Starting compounds of the above-mentioned compound (I) of the present invention may be in the form of a salt.

While there is no specific restriction on kinds of the salt, so long as the reaction proceeds, are used, for example, substantially the same salts as those which the above-mentioned compound (I) may form.

Referring to the configurational isomers (E- and Z-isomers) of the compounds (I), (IV), (V), (VII), (VIII), (IX) and (X), when such isomerization takes place, the isomers can be isolated and purified by a conventional separating methods such as extraction, recrystallization, distillation and chromatography to give pure compounds. And, in accordance with the methods described in "Shin Jikken Kagaku Koza" 14 (compiled by The Chemical Society of Japan), pp.251–253, "Fourth Edition Jikken Kagaku Koza" 19 (compiled by The Chemical Society of Japan), pp.273–274 and analogous methods thereto, isomerization of the double bond is allowed to proceed by heating, using an acid catalyst, a metal catalyst, a radical catalyst, light irradiation or using a strongly basic catalyst to give the corresponding pure isomer.

Incidentally stating, the compound (I) gives rise to stereoisomers depending of the kinds of substituents, and these isomers, singly or as a mixture of them, are included in the present invention.

In any of such cases, when further desired, the compound (I) can be synthesized by deprotection, acylation, alkylation, hydrogenation, oxidation, reduction, carbon chain elongation, substituent-exchange reaction singly or by combination of two or more of them.

In the case where the object compound is obtained in the free form by the above reaction, it may optionally be converted into a corresponding salt by conventional methods, and, in the case where the object compound is obtained as a salt, it can be converted into the free form or any other salt. The obtained compound (I) can be isolated from the reaction mixture and purified by conventional methods such as phasic transfer, concentration, solvent-extraction, fractional distillation, crystallization, recrystallization and chromatography.

Additionally stating, in the case where the compound (I) is present as, for example, configurational isomer, diastereomer or conformer, they can be isolated, when desired, respectively by the above-mentioned isolation and purification means. And, when the compound (I) is a racemic compound, it can be resolved into d-isomer and l-isomer by a conventional means for optical resolution.

Effects

The compound (I) and (Ia) shows a high affinity for the melatonin receptor, and is less in toxicity and undesirable side effects, which is thus useful as a medicine.

The compound (I) and (Ia) acts, as a melatonin agonist or antagonist, in mammals (e.g. mouse, rat, hamster, rabbit, cat, dog, cow, sheep, monkey and man), and, therefore, it can be used as a pharmaceutical composition having a binding affinity to the melation receptor, especially, melatoninagonist or antagonist, for the therapy of diseases possibly affected by melatonin, for example, sleep-awake rhythm disorders, jet lag, abnormal physical conditions caused by a three-shift labor system, seasonal melancholia, disorders in reproduction and neurosecretion, senile dementia including Alzheimer's disease, various disorders accompanied with aging, cerebral circulation disorders, stress, epilepsy, convulsion, anxiety, parkinsonism, hypertension, glaucoma, cancer and insomnia, or it can be used as an agent of controlling ovulation. Especially the compound (I) and (Ia) can be used as a therapeutic agent for insomnia and circadian rhyzm disturbance including sleep-awake rhyzm disturbance (e.g. jet lag and insomnia of shift workers).

The compound (I) and (Ia) can be safely administered orally or non-orally as it is or as medicinal preparations mixed with a pharmaceutically acceptable carriers in accordance with a per se known method, for example, tablets (including sugar-coated tablets and film-coated tablets), powdery preparations, granular preparations, capsules (containing soft-capsules), liquid preparations, injectable preparations, suppository preparations, sustained release preparations, plasters and chewing gum.

The amount of the compound (I) or (Ia) in the composition of the present invention is about 0.01 to 100 w/w %. The daily dose varies with, for example, subjects to be administered, administration routes and diseases to be treated, and, it is preferable, when administered to, for example, an adult patient suffering from sleep disorders, to administer once daily or severally divided dosages in an amount ranging from about 0.1 mg/kg to 20 mg/kg body weight, preferably from 0.2 mg/kg to 10 mg/kg body weight, more preferably from 0.5 mg/kg to 10 mg/kg body weight, in terms of the effective component (the compound (I) or (Ia)).

The compound (I) or (Ia) may be used with another active component, for example, benzodiazepine such as triazolam, regulating agents of sleep rhythm such as butoctamide and salts thereof, sleep inducing substances such as cis-9,10-octadecenamide. The compound (I) or (Ia) can be used as a pharmaceutical composition, for example, tablet, powdery preparation, granular preparation, capsule (containing soft capsule).

As pharmaceutically acceptable carriers, various organic or inorganic carriers, which are conventionally employed in the field of formulation of pharmaceutical preparations, can be used, and they are incorporated as excipients, lubricants, binders and disintegrants in solid compositions; and as solvents, solubilizers, suspending agents, isotonizing agent, buffering agent and pain-easing agents in liquid compositions. And, depending on necessity, further additives such as preservatives, anti-oxidants, coloring agent and sweeteners can also be supplemented. Preferable examples of excipients include lactose, sugar, D-mannitol, starch, crystalline cellulose and more volatile silicon dioxide. Preferable examples of lubricants include magnesium stearate, talc and colloid silica. Preferable examples of binders include crystalline cellulose, sugar, D-mannitol, dextrin, hydroxypropyl cellulose, hydroxypropylmethyl cellulose and polyvinyl pyrrolidone. Preferable examples of disintegrants include starch, carboxymethyl cellulose, carboxymethyl cellulose calcium, cross carmelose sodium and carboxymethyl starch sodium. Preferable examples of solvents include water for injection, alcohol, propylene glycol, macrogol, sesame oil and corn oil. Preferable examples of solubilizers include polyethylene glycol, propylene glycol, D-mannitol, benzyl benzoate, ethanol, tris-aminomethane, cholesterol, triethanolamine, sodium carbonate and sodium citrate. Preferable examples of suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hdyroxymethyl cellulose, hydroxyethyl cellulose and hydroxypropyl cellulose. Preferable examples of isotonizing agents include sodium chloride, glycerin and D-mannitol. Preferable examples of buffering agents include buffering solutions such as phosphate, acetate, carbonate and citrate. Preferable examples of pain-easing agents include benzyl alcohol. Preferable examples of preservatives include para-hydroxybenzoic acid esters, chlorobutanol, benzyl alcohol, phenethyl alcohol, dehydroacetic acid and sorbic acid. Preferable examples of anti-oxidants include sulfite, ascorbic acid and α-tocopherol.

BEST MODE FOR CARRYING OUT THE INVENTION

Examples

The present invention will be described in further detail by the following Reference Examples, Working Examples and Experimental Examples, but they are mere examples and are not intended by way of limitation upon the scope of this invention, and they may be modified within the range which does not deviate the scope of this invention.

In the following Working Examples, Reference Examples and Experimental Examples, "room temperatures" means 0 to 30° C., and other definitions have the following meanings.

s: singlet
d: doublet
t: triplet
q: quartet
m: multiplet
br: broad
J: coupling constant
Hz: Hertz
$CDCl_3$: deuterochloroform
$D_2O$: deuterium oxide
THF: tetrahydrofuran
DMF: N,N-dimethylformamide
$d_6$-DMSO: (dimethylsulfoxide)-$d_6$
NMR: proton-nuclear magnetic resonance

Reference Example 1

(1,2,3,4-tetrahydro-7-methoxy-1-naphthylidene) acetonitrile

To a solution of 60% sodium hydride (6.24 g, 156 mmol) in tetrahydrofuran (100 ml) was gradually added dropwise, under ice-cooling, diethyl cyanomethyl phosphonate (30.4 g, 172 mmol). The mixture was stirred for 15 minutes. To the reaction mixture was then added dropwise a solution of 7-methoxy-1-tetralone (25.2 g, 143 mmol) in THF (50 ml). The reaction mixture was heated for 3 hours under reflux. The reaction mixture was poured into water, and the organic layer was subjected to extraction with chloroform. The extract solution was washed with brine and water, which was dried over anhydrous magnesium sulfate, followed by distilling off the solvent under reduced pressure. The residue was purified by means of a silica gel column chromatography (hexane:ethyl acetate=9:1) to give the above-titled compound (a mixture of isomers) (28 g, yield 98%, oil). The above-titled compound (a mixture of isomers) was further purified by a silica gel column chromatography (hexane:ethyl acetate=98:2) to fractionally refine the respective isomers.

E-isomer m.p. 59–61° C.

NMR($CDCl_3$) δ: 1.85–2.00(2H,m), 2.76–2.91(4H,m), 3.81(3H,s), 5.70(1H,s), 6.91(1H,dd,J=2.6 Hz,8.4 Hz), 7.03 (1H,d,J=2.6 Hz), 7.10(1H,d,J=8.4 Hz).

Z-isomer oil

NMR($CDCl_3$) δ: 1.87–2.02(2H,m), 2.54–2.64(2H,m), 2.83(2H,t,J=6.2 Hz), 3.85(3H,s), 5.28(1H,s), 6.93(1H,dd,J=2.6 Hz,8.4 Hz), 7.09(1H,d,J=2.6 Hz), 7.86(1H,d,J=8.4 Hz).

Reference Example 2

(Z)-(1,2,3,4-Tetrahydro-7-methoxy-1-naphthylidene) acetonitrile

To a solution of (1,2,3,4-tetrahydro-7-methoxy-1-naphthylidene)acetonitrile (4.0 g, 20 mmol) in ethanol (10 ml) were added a saturated ammonia/ethanol solution (5 ml) and Raney cobalt (ODHT-60, 1 g). The reaction mixture was stirred for 3.5 hours at room temperature under hydrogen atmosphere (about 4 kgf/$cm^2$). The Raney cobalt was filtered off, then the solvent was distilled off under reduced pressure. To the residue was added dilute hydrochloric acid, then the organic layer was subjected to extraction with ethyl acetate. The extract solution was washed with a saturated aqueous solution of sodium hydrogencarbonate and water, which was dried over anhydrous magnesium sulfate, followed by distilling off the solvent under reduced pressure. The residue was purified by means of a silica gel column chromatography to give the above-titled compound (yield 2.14 g, oil).

NMR($CDCl_3$) δ: 1.87–2.02(2H,m), 2.54–2.64(2H,m), 2.83(2H,t,J=6.2 Hz), 3.85(3H,s), 5.28(1H,s), 6.93(1H,dd,J=2.6 Hz,8.4 Hz), 7.09(1H,d,J=2.6 Hz), 7.86(1H,d,J=8.4 Hz).

Reference Example 3-A 1-(2-Aminoethylidene)-7-methoxy-1,2,3,4-tetrahydronaphthalene To a solution of (1,2,3,4-tetrahydro-7-methoxy-1-naphthylidene)acetonitrile (15.0 g, 25 mmol) in ethanol (100 ml) were added a saturated ammonia/ethanol solution (30 ml) and Raney nickel (W-2, 3 g). The reaction mixture was stirred for 8 hours at 50° C. under hydrogen atmosphere (3–4 kgf /$cm^2$). The Raney nickel was filtered off, then the solvent was distilled off under reduced pressure to give the above-titled compound (a mixture of isomers (20.4 g, yield 80%, oil). This compound was used in the subsequent reaction without further purification.

Reference Example 3-B 1-(2-Aminoethylidene)-7-methoxy-1,2,3,4-tetrahydronaphthalene To a solution of (Z)-(1,2,3,4-tetrahydro-7-methoxy-1-naphthylidene)acetonitrile produced in Reference Example 2 (1.84 g, 9.23 mmol) in ethanol (10 ml) were added a saturated ammonia/ethanol solution (5 ml) and Raney cobalt (ODHT-60, 1.8 g). The mixture was stirred for 3 hours at room temperature under hydrogen atmosphere (about 4 kgf/$cm^2$). The Raney cobalt was filtered off, then the solvent was distilled off to give the above-titled compound (a mixture of isomers) (yield 1.46 g, 78%, oil). This compound was used in the subsequent reaction without further purification.

Reference Example 4

(6-Methoxyindan-1-ylidene)acetonitrile

To a solution of 60% sodium hydride (2.71 g, 67.9 mmol) in THF (150 ml) was added dropwise, under ice-cooling, diethyl cyanomethylphosphonate (11.5 g, 64.8 mmol). The mixture was stirred for 15 hours, to which was then added dropwise a solution of 6-methoxy-1-indanone (10.0 g, 61.7 mmol) in THF (30 ml). The reaction mixture was stirred for 30 minutes at room temperature. The reaction mixture was poured into water, and the organic layer was subjected to extraction with ethyl acetate. The extract solution was washed with brine and water, followed by drying over anhydrous magnesium sulfate. The solvent was then distilled off under reduced pressure. The residue was purified by means of a silica gel column chromatography (hexane:ethyl acetate=8:2). Recrystallization of the product-from ethyl acetate/hexane afforded the above-titled compound (6.00 g, yield 53%).

m.p.95–96° C. (recrystallized from ethyl acetate/hexane)

NMR($CDCl_3$) δ: 3.01–3.18(4H,m), 3.83(3H,s), 5.61(1H, t,J=2.4 Hz), 6.96–7.03(2H,m), 7.27(1H,d,J=8.8 Hz).

Reference Example 5

1-(2-Aminoethyl)-6-methoxyindan

To a solution of (6-methoxyindan-1-ylidene), acetonitrile (4.00 g, 21.6 mmol) in ethanol (80 ml) were added a saturated ammonia/ethanol solution (40 ml) and Raney nickel (W-2, 4 g). The reaction mixture was stirred, under hydrogen atmosphere (3 kg f/cm$^2$), for 5 hours at room temperature, then for 2 hours at 50° C. The Raney nickel was filtered off, then the solvent was distilled off under reduced pressure. The residue was purified by means of a silica-gel column chromatography (chloroform:methanol=97.3 to chloroform:methanol:triethylamine=90:7:3) to give the above-titled compound (3.30 g, yield 80%, oil).

NMR($CDCl_3$) δ: 1.50–1.76(2H,m), 1.90–2.08(1H,m), 1.22–1.34(1H,m), 2.65–3.20(5H,m), 3.79(3H,s), 6.71(1H, dd,J=2.6 Hz,8.2 Hz), 6.76(1H,br s), 7.12(1H,d,J=8.2 Hz).

Reference Example 6

1-Cyanomethyl-1-hydroxy-7-methoxy-2,2-dimethyl-1,2,3,4-tetrahydronaphthalene

To a solution of 1,1,1,3,3,3-hexamethyldisilazane (4.74 g, 29.4 mmol) in THF (30 ml) was gradually added dropwise, at −78° C., a butyllithium hexane solution (1.56 M hexane solution, 18.8 ml, 29.4 mmol). The mixture was stirred for 10 minutes, to which was then added acetonitrile (1.41 ml, 26.9 mmol). The reaction mixture was stirred for further 20 minutes, to which was then added dropwise a solution of 7-methoxy-2,2-dimethyl-1-tetralone (5.0 g, 24.5 mmol) in THF (10 ml), followed by stirring for 2 hours. The reaction mixture was poured into water, and the organic layer was subjected to extraction with chloroform. The extract solution was washed with brine and water, which was dried over anhydrous magnesium sulfate, followed by distilling off the solvent under reduced pressure. The residue was purified by means of a silica gel column chromatography (ethyl acetate:hexane=2:8) to give the above-titled compound (5.3 g, yield 88%).

m.p.107–108° C.

NMR($CDCl_3$) δ: 0.97(3H,s), 1.15(3H,s), 1.60–1.95(2H, m), 1.97(1H,s), 2.69–2.98(4H,m), 3.83(3H,s), 6.81(1H,dd, J=2.7 Hz,8.4 Hz), 7.00(1H,d,J=8.4 Hz), 7.34(1H,d,J=2.7 Hz).

Elemental Analysis for $C_{15}H_{19}NO_2$: Calcd.: C, 73.44; H, 7.81; N, 5.71. Found: C, 73.64; H, 7.74; N, 5.83.

Reference Example 7

(1,2,3,4-Tetrahydro-7-methoxy-2,2-dimethyl-1-naphthylidene)acetonitrile

To a solution of 1-cyanomethyl-1-hydroxy-7-methoxy-2, 2-dimethyl-1,2,3,4-tetrahydronaphthalene (5.27 g, 21.5-mmol) in toluene (50 ml) was added camphor sulfonic acid (0.5 g, 2.15 mmol). The mixture was heated for one hour under reflux. The reaction mixture was poured into a saturated aqueous solution of sodium hydrogencarbonate, and the organic layer was subjected to extraction with chloroform. The extract solution was washed with brine and water, which was dried over magnesium sulfate, followed by distilling off the solvent under reduced pressure. The residue was purified by means of a silica gel column chromatography (ethyl acetate:hexane=2:8) to give the above-titled compound (a mixture of isomers) (4.88 g, quantitative).

NMR($CDCl_3$) δ: 1.16(4H,s,Z-isomer), 1.52(2H,s,E-isomer), 1.66(0.67H,t,J=6.6 Hz,E-isomer), 1.75(1.33H,t,J=6.6 Hz,Z-isomer), 2.70(0.67H,t,J=6.6 Hz,E-isomer), 2.83 (1.33H,t,J=6.6 Hz,Z-isomer), 3.81(1H,s,E-isomer), 3.86 (2H,s,Z-isomer), 5.37(0.67H,s,Z-isomer), 5.70(0.33H,s,E-isomer), 6.87–7.12(2.33H,m,E-isomer+Z-isomer), 7.64 (0.67H,d,J=2.6 Hz,Z-isomer).

Reference Example 8

1-(2-Aminoethylidene)-7-methoxy-2,2-dimethyl-1,2,3,4-tetrahydronaphthalene

By substantially the same manner as in Reference Example 3-B, a mixture of isomers of the above-titled compound was produced from (1,2,3,4-tetrahydro-7-methoxy-2,2-dimethyl-1-naphthylidene)acetonitrile (yield 99%).

NMR($CDCl_3$) δ: 1.11(4H,s,Z-isomer), 1.30(2H,s,E-isomer), 1.56(0.67H,t,J=6.9 Hz,E-isomer), 1.66(1.33H,t,J=6.9 Hz,Z-isomer), 2.61(0.67H,t,J=6.9 Hz,E-isomer), 2.75 (1.33H,t,J=6.9 Hz,Z-isomer), 3.63(2H,d,J=6.8 Hz,Z-isomer), 3.70(1H,d,J=6.8 Hz,E-isomer), 3.80 and 3.81(3H, sX2,E-isomer+Z-isomer), 5.54(0.67H,t,J=6.4 Hz,Z-isomer), 5.89(0.33H,d,J=7.1 Hz,E-isomer), 6.68–7.10(3H,m,E-isomer+Z-isomer).

Reference Example 9

(2-Methoxy-6,7,8,9-tetrahydro-5H-benzocyclohepten9-ylidene)acetonitrile

By substantially the same manner as in Reference Example 1, the above-titled compound was produced from 2-methoxy-6,7,8,9-tetrahydro-5H-benzocyclohepten-9-one. This compound was used in the subsequent reaction without purification.

Reference Example 10

(E)-9-(2-Aminoethylidene)-2-methoxy-6,7,8,9-tetrahydro-5H-benzocycloheptene

To a solution of (2-methoxy-6,7,8,9-tetrahydro-5H-benzocyclohepten-9-ylidene)acetonitrile (2.00 g, 9.38 mmol) in ethanol (10 ml) were added a saturated solution of ammonia/ethanol (5 ml) and Raney nickel (W-2, 2 g). The mixture was stirred for 4 hours at 50° C. under hydrogen atmosphere (4 kgf/cm$^2$). The Raney nickel was filtered off, then the solvent was distilled off under reduced pressure. The residue was purified by means of a silica gel column chromatography (chloroform:methanol=9:1 to chloroform:methanol:triethylamine=90:8:2) to give the above-titled compound (1.50 g, yield 74%, oil).

NMR($CDCl_3$) δ: 1.60–1.75(4H,m), 2.33–2.41(2H,m), 2.61–2.72(2H,m), 3.47(2H,d,J=7.0 Hz), 3.79(3H,s), 5.53 (1H,t,J=6.6 Hz), 6.66–6.75(1H,m), 6.96–7.02(1H,m), 7.14–7.17(1H,m).

Reference Example 11

(E)-1-(2-Aminoethylidene)-6-methoxyindan

To a solution of (6-methoxyindan-1-ylidene) acetonitrile (1.60 g, 8.64 mmol) in ethanol (80 ml) were added a 2M ammonia/ethanol solution (40 ml) and Raney cobalt (1.6 g). The mixture was stirred, under hydrogen atmosphere (4 kgf/$cm^2$), for 32 hours at 40° C., and for further 8 hours at 70° C. The Raney cobalt was filtered off, then the solvent was distilled off under reduced pressure. The residue was purified by means of a silica gel column chromatography (chloroform:methanol=9:1 to chloroform:methanol:triethylamine=90:8:2) to give the above-titled compound (yield 1.40 g, 86%, oily).

NMR($CDCl_3$)S: 2.70–2.80(2H,m), 2.89–2.97(2H,m), 3.48(2H,d,J=6.6 Hz), 3.81(3H,s), 5.91–6.01(1H,m), 6.77 (1H,dd,J=2.4 Hz,8.2 Hz), 6.96(1H,d,J=2.4 Hz), 7.13(1H,d, J=8.2 Hz).

Reference Example 12

(5,6-Dimethoxyindan-1-ylidene)acetonitrile

In substantially the same manner as in Reference Example 1, the above-titled compound was produced from 5,6-dimethoxy-indanone. The product was used in the subsequent reaction without purification.

Reference Example 13

1-(2-Aminoethyl)-5,6-dimethoxyindan hydrochloride

To a solution of (5,6-dimethoxyindan-1-ylidene) acetonitrile (1.70 g, 7.90 mmol) and Raney nickel (1.7 g) in ethanol (80 ml) was added 2M ammonia/ethanol solution (40 ml). The mixture was stirred for 12 hours at 50° C. under hydrogen atmosphere (3.2 kgf/$cm^2$). The Raney cobalt was filtered off, and then the solvent was distilled off. The residue was dissolved in ethanol(25 mL), to which was added 5% palladium-carbon (1 g, content 50%). The mixture was stirred for 1.5 hours at room temperature under hydrogen atmosphere. The palladium-carbon was filtered off. To the filtrate was added 10% HCl/ethanol, and the mixture was concentrated. The concentrate was recrystallized from ethyl acetate-isopropyl ether to give the above-titled compound (0.90 g, yield 44%).

m.p.175–179° C. (decomp.)

NMR($CDCl_3$) δ: 1.59–1.97(2H,m), 2.18–2.40(2H,m), 2.77–2.86(2H,m), 3.05(2H,t,J=8.0 Hz), 3.18(1H,br s), 3.84 (3H,s), 3.85(3H,s), 6.73(1H,s), 6.75(1H,s).

Reference Example 14

1-(2-Aminoethyl)-7-methoxy-2,2-dimethyl-1,2,3,4-tetrahydronaphthalene hydrochloride To a solution of 1-(2-aminoethylidene)-7-methoxy-2,2-dimethyl-1,2,3,4-tetrahydronaphthalene (10.2 g, 44.1 mmol) in ethanol (50 ml) was added 5% Pd-C (50% hydrous, 1 g). The mixture was subjected to catalytic reduction at room temperature under hydrogen atmosphere (latm). After completion of hydrogenation in a theoretical volume, the Pd-C catalyst was filtered off. From the filtrate, the solvent was distilled off. The residue was neutralized with hydrogen chloride to give the above-titled compound (yield 10.7 g, 90%), m.p.141–143° C. (recrystallized from ethanol).

NMR($d_6$-DMSO,$D_2O$) δ: 0.83(3H,s), 1.01(3H,s), 1.30–1.80(5H,m), 1.90–2.10(1H,m), 2.25–2.40(1H,m), 2.60–2.96(4H,m), 3.72(3H,s), 6.63(1H,d,J=2.2 Hz), 6.73 (1H,dd,J=2.2 Hz, 8.4 Hz), 7.03(1H,d,J=8.4 Hz).

Elemental Analysis for $C_{15}H_{23}NO.HCl$: Calcd.: C, 66.77; H, 8.97; N, 5.19; Cl, 13.14 Found: C, 66.61; H, 9.02; N, 5.20; Cl, 13.19

Reference Example 15

(1,2,3,4-Tetrahydro-5,7-dimethyl-1-naphthylidene) acetonitrile

By substantially the same procedure as in Reference Example 1, a mixture of isomers of the above-titled compound was produced from 5,7-dimethyl-1-tetralone and diethyl cyanomethylphosphonate (yield 93%), m.p.71–73° C. (recrystallized from ethyl acetate/hexane).

NMR($CDCl_3$) δ: 1.96(2H,m), 2.23(3H,s), 2.30(3H,s), 2.72(2H,t,J=6.2 Hz), 2.79–2.88(2H,m), 5.69(1H,s), 7.06 (1H,s), 7.22(1H,s).

Elemental Analysis Calcd for $C_{14}H_{15}N$: Calcd.: C, 85.24; H, 7.66; N, 7.10. Found: C, 85.19; H, 7.59; N, 7.13.

Reference Example 16

1-(2-Aminoethylidene)-5,7-dimethyl-1,2,3,4-tetrahydronaphthalene

By substantially the same procedure as in Reference Example 3-B, a mixture of isomers of the above-titled compound was produced from (1,2,3,4-tetrahydro-5,7-dimethyl-1-naphthylidene)acetonitrile (yield 88%, oil).

NMR($CDCl_3$) δ: 1.75–1.93(2H,m), 2.15–2.30(6H,m), 2.40–2.90(4H,m), 3.44–3.65(2H,m), 5.85–6.08(1H,m), 6.85–7.30(2H,m).

Reference Example 17

(1,2,3,4-tetrahydro-6,7-dimethoxy-1-naphthylidene) acetonitrile

By substantially the same procedure as in Reference Example 1, the above-titled compound was produced from 6,7-dimethoxy-1-tetralone and diethyl cyanomethylphosphonate (yield 95%, oil).

NMR($CDCl_3$) δ: 1.85–2.00(2H,m), 2.80–3.00(4H,m), 3.89(3H,s), 3.90(3H,s), 5.57(1H,s), 6.63(1H,s), 6.99(1H,s).

Reference Example 18

1-(2-Aminoethylidene)-6,7-dimethoxy-1,2,3,4-tetrahydronaphthalene

By substantially the same procedure as in Reference Example 3-B, a mixture of isomers of the above-titled compound was produced from (1,2,3,4-tetrahydro-6,7-dimethoxy-1-naphthylidene)acetonitrile (yield 65%, oil).

NMR($CDCl_3$) δ: 1.75–1.95(2H,m), 2.20–2.90(4H,m), 3.44–3.60 (2H,m), 3.80–4.00(6H,m), 5.77–6.00(1H,m), 6.55–7.20(2H,m).

Reference Example 19

2-Isopropoxy-6,7,8,9-Tetrahydro-5H-benzocyclohepten-9-one

To a suspension of 2-hydroxy-6,7,8,9-Tetrahydro-5H-benzocyclohepten-9-one (9.69 g, 56.3 mmol) and potassium carbonate (23.3 g, 0.17 mol) in DMF (60 ml) was added dropwise, under ice-cooling, isopropyl bromide (34.6 g, 0.28 mol). The reaction mixture was stirred for one hour at 100° C., which was poured into water, followed by extraction of the organic substance with ethyl acetate. The extract solution was washed with brine and water, which was dried over anhydrous magnesium sulfate, followed by distilling off the solvent. The residue was purified by means of a silica gel column chromatography (hexane:ethyl acetate=9:1) to give the above-titled compound (11.4 g, yield 93%, oil).

NMR($CDCl_3$) δ: 1.33(6H,d,J=5.7 Hz), 1.70–1.92(4H,m), 2.72(2H,t,J=5.9 Hz), 2.87(2H,d,J=5.9 Hz), 4.58(1H,m), 6.95 (1H,dd,J=2.7 Hz,8.2 Hz), 7.10(1H,d,J=8.2 Hz), 7.26(1H,d, J=2.7 Hz).

Reference Example 20

(2-Isopropoxy-6,7,8,9-tetrahydro-5H-benzocyclohepten-9-ylidene)acetonitrile

By substantially the same procedure as in Reference Example 1, a mixture of isomers of the above titled compound was produced from 2-isopropoxy-6,7,8,9-tetrahydro-5H-benzocyclohepten-5-one and diethyl cyanomethylphosphonate (yield 94%, oil).

NMR($CDCl_3$) δ: 1.20–1.43(6H,m), 1.60–2.20(4H,m), 2.40–2.80(4H,m), 4.40–4.60(1H,m), 5.30–5.43(1H,m), 6.60–7.20(3H,m).

Reference Example 21

9-(2-Aminoethylidene)-2-isopropoxy-6,7,8,9-tetrahydro-5H-benzocycloheptene

By substantially the same procedure as in Reference Example 3-B, a mixture of isomers of the above-titled compound was produced from (2-isopropoxy 6,7,8,9-tetrahydro-5H-benzocyclohepten-9-ylidene)acetonitrile (yield 91%, oil). 3.18–3.50(2H,m), 4.40–4.60(1H,m), 5.47–5.65(1H,m), 6.55–7.10(3H,m).

Reference Example 22

6-Methoxy-2,2-dimethyl-1-indanone

To a suspension of 60% sodium hydride (2.22 g, 55.5 mmol) in 1,2-dimethoxyethane (20 ml) was added, under ice-cooling, a suspension of 6-methoxy-1-indanone (3.00 g, 18.5 mmol) in 1,2-dimethoxyethane (10 ml). The mixture was stirred for 5 minutes, to which was added dropwise methyl iodide (4.61 mL, 74.0 mmol), and the mixture was stirred for 20 minutes. To the reaction mixture was added water, and the mixture was subjected to extraction with ethyl acetate. The extract-solution was washed with brine, which was dried over anhydrous magnesium sulfate, followed by distilling off the solvent under reduced pressure. The residue was purified by means of a silica gel column chromatography (hexane→hexane/ethyl acetate, 9:1) to give 3.15 g (yield 90%) of the above-titled compound as an oily product.

NMR($CDCl_3$) δ: 1.23(6H,s), 2.92(2H,s), 3.84(3H,s), 7.16–7.34(3H,m).

Reference Example 23

(Z)-(6-methoxy-2,2-dimethylindan-1-ylidene) acetonitrile and (E)-(6-methoxy-2,2-dimethylindan-1-ylidene)acetonitrile To a solution of 1,1,1,3,3,3-hexamethyldisilazane (4.13 ml, 19.6 mmol) in THF (80 ml) was added dropwise, under argon atmosphere at −78° C., a 1.56M solution of n-butyllithium hexane solution (12.5 ml, 19.6 mmol). The mixture was stirred for 10 minutes, to which was added acetonitrile (0.94 ml, 17.9 mmol), and the mixture was stirred for further 15 minutes. To the mixture was added a solution of 6-methoxy-2,2-dimethyl-1-indanone (3.00 g, 16.3 mmol) in THF (10 ml), which was stirred for 15 minutes. To the reaction mixture was added water so that the temperature was gradually reverted to room temperature. The reaction mixture was subjected to extraction with ethyl acetate. The extract solution was washed with brine, which was dried over anhydrous magnesium sulfate, followed by distilling off the solvent under reduced pressure. The residue was dissolved in toluene (100 ml). To the solution was added 10-camphor sulfonic acid (0.5 g), and the mixture was heated for 1.5 hours under reflux. The reaction mixture was cooled, to which was added water. The mixture was subjected to extraction with ethyl acetate. The extract solution was washed with brine, which was dried over anhydrous magnesium sulfate, followed by distilling off the solvent under reduced pressure. The residue was subjected to a silica gel column chromatography (hexane/ethyl acetate, 97:3→9:1) to give 1.03 g (yield 30%) of (Z)-(6-methoxy-2,2-dimethylindan-1-ylidene)acetonitrile as an oily product.

NMR($CDCl_3$) δ: 1.26(6H,s), 2.83(2H,s), 3.86(3H,s), 5.17 (1H,s), 7.01(1H,dd,J=2.4 Hz,8.2 Hz), 7.20(1H,d,J=8.2 Hz), 7.88(1H,d,J=2.4 Hz).

The elution on the silica gel column chromatography was further continued to give 1.78 g (yield 52%) of (E)-(6-methoxy-2,2-dimethylindan-1-ylidene)acetonitrile as an oily product.

NMR($CDCl_3$) δ: 1.51(6H,s), 2.91(2H,s), 3.83(3H,s), 5.65 (1H,s), 6.92(1H,d,J=2.4 Hz), 7.01(1H,dd,J=2.4 Hz,8.4 Hz), 7.19(1H,d,J=8.4 Hz).

Reference Example 24

1-(2-Aminoethyl)-6-methoxy-2,2-dimethylindan hydrochloride

By substantially the same procedure as in Reference Example 3-A, a free base of the above titled compound was produced from (E)-(6-methoxy-2,2-dimethylindan-1-ylidene)acetonitrile. The base was converted to hydrochloride by using an ethanol solution of hydrogen chloride to give the above-titled compound (yield 74%), m.p.194–195° C. (recrystallized from ethanol/isopropyl ether).

NMR($d_6$-DMSO,) δ: 0.93(3H,s), 1.07(3H,s), 1.59–1.94 (2H,m), 2.55–2.69(3H,m), 2.91(2H,t,J=8.0 Hz), 3.72(3H,s), 6.69(1H,dd,J=2.4 Hz,8.2 Hz), 6.78(1H,d,J=2.4 Hz), 7.08 (1H,d,J=8.2 Hz), 7.94(2H,br s).

Reference Example 25

(E)-1-(2-Aminoethylidene)-6-methoxy-2,2-dimethylindan

By substantially the same procedure as in Reference Example 3-B, the above-titled compound was produced from (E)-(6-methoxy-2,2-dimethylindan-1-ylidene) acetonitrile (yield 96%) as an oily product.

NMR($CDCl_3$) δ: 1.34(6H,s), 2.79(2H,s), 3.64(2H,d,J=7.4 Hz), 3.80(3H,s), 5.95(1H,t,J=7.4 Hz), 6.78(1H,dd,J=2.4 Hz,8.2 Hz), 6.92(1H,d,J=2.4 Hz), 7.04(1H,d,J=8.2 Hz).

Reference Example 26

(Z)-1-(2-Aminoethylidene)-6-methoxy-2,2-dimethylindan

By substantially the same manner as in Reference example 3-B, the above-titled compound was produced from (Z)-(6-methoxy-2,2-dimethylindan-1-ylidene)acetonitrile (yield 98%) as an oily product.

NMR($CDCl_3$) δ: 1.18(6H,s), 2.73(2H,s), 3.76–3.84(2H, m), 3.81(3H,s), 5.46(1H,t,J=6.2 Hz), 6.79(1H,dd,J=2.4 Hz,8.2 Hz), 7.00(1H,d,J=2.4 Hz), 7.14(1H,d,J=8.2 Hz).

Reference Example 27

Ethyl (6-methoxyindan-1-yl)acetate

To a suspension of 60% sodium hydride (1.84 g, 46.0 mmol) in THF (200 ml) was added dropwise, under ice-cooling, triethyl phosphonoacetate (10.3, g, 46.0 mmol). The mixture was stirred until the reaction mixture became a homogeneous solution. To the solution was added a suspension of 6-methoxy-1-indanone (7.10 g, 43.8 mmol) in THF (30 ml). The mixture was stirred for 2 hours at room temperature and for further 12 hours at 70° C. To the reaction mixture was added water, which was subjected to extraction with ethyl acetate. The extract solution was washed with brine, which was dried over anhydrous magnesium sulfate, followed by concentration under reduced pressure. The concentrate was dissolved in ethanol (200 ml), to which was added 5% Pd-C (50% hydrous, 2.5 g). The mixture was stirred for 1.5 hours at 50° C. under hydrogen atmosphere. The reaction mixture was subjected to filtration, and the filtrate was concentrated under reduced pressure. The concentrate was purified by means of a silica gel column chromatography (hexane/ethyl acetate, 97:3→4:1) to give 6.55 g (yield 64%) of the above-titled compound as an oily product.

NMR($CDCl_3$) δ: 1.28(3H,t,J=7.2 Hz), 1.67–1.83(1H,m), 2.30–2.47(2H,m), 2.69–2.95(3H,m), 3.47–3.62(1H,m), 3.78 (3H,s), 4.18(2H,q,J=7.2 Hz), 6.69–6.75(2H,m), 7.11(1H,d, J=8.6 Hz).

Reference Example 28

1-(2-Hydroxyethyl)-6-methoxyindan

To a suspension of lithium aluminum hydride (1.06 g, 27.9 mmol) in THF (150 ml) was added dropwise, under ice-cooling, a solution of ethyl (6-methoxyindan-1-yl) acetate (6.53 g, 27.9 mmol) in THF (20 ml), and the mixture was stirred for 15 minutes. To the reaction mixture was added water (1 ml), to which were further added ethyl acetate, anhydrous magnesium sulfate and celite. The mixture was subjected to filtration. The filtrate was concentrated under reduced pressure to give 4.96 g (yield 93%) of the above-titled compound as an oily product.

NMR($CDCl_3$) δ: 1.35(1H,br s), 1.60–1.82(2H,m), 2.06–2.41(2H,m), 2.69–2.96(2H,m), 3.15–3.28(1H,m), 3.75–3.88(2H,m), 3.79(3H,s), 6.68–6.79(2H,m), 7.12(1H,d, J=8.0 Hz).

Reference Example 29

1-(2-Bromoethyl)-6-methoxyindan

To a solution of 1-(2-hydroxyethyl)-6-methoxyindan (4.95 g, 25.7 mmol) in dichloromethane (100 ml) was added dropwise at −5° C. phosphorus tribromide (0.86 ml, 2084 27.0 mmol). The mixture was stirred for 30 minutes. To the reaction mixture was added water, which was subjected to extraction with chloroform. The extract solution was washed with brine and dried over anhydrous magnesium sulfate, followed by distilling off the solvent under reduced pressure. The residue was purified by means of a silica gel column chromatography (hexane/ethyl acetate, 7:3→1:1) to give 1.80 g (yield 27%) of the above-titled compound as an oily product.

NMR($CDCl_3$) δ: 1.60–1.78(1H,m), 1.88–2.06(1H,m), 2.24–2.41(2H,m), 2.70–2.96(2H,m), 3.21–3.38(1H,m), 3.41–3.60(2H,m), 3.79(3H,s), 6.68–6.78(2H,m), 7.12(1H,d, J=7.6 Hz).

Reference Example 30

1-(2-Cyanoethyl)-6-methoxyindan

To a solution of 1-(2-bromoethyl)-6-methoxyindan (1.75 g, 6.86 mmol) in dimethyl sulfoxide (80 ml) was added sodium cyanide (0.35 g, 7.20 mmol). This mixture was stirred for 40 minutes at 60° C. To the reaction mixture was added water, which was subjected to extraction with ethyl acetate. The extract solution was washed with brine and dried over anhydrous magnesium sulfate, followed by distilling off the solvent under reduced pressure. The residue was purified by means of a silica gel column chromatography (hexane/ethyl acetate, 85:15) to give 1.28 g (yield 93%) of the above-titled compound as an oily-product.

NMR($CDCl_3$) δ: 1.62–1.89(2H,m), 2.03–2.48(4H,m), 2.71–2.96(2H,m), 3.18–3.33(1H,m), 3.80(3H,s), 6.72–6.78 (2H,m), 7.13(1H,d,J=9.0 Hz).

Reference Example 31

1-(3-Aminopropyl)-6-methoxyindan

By substantially the same procedure as in Reference Example 3-A, the above-titled compound was obtained (yield 96%) from 1-(2-cyanoethyl)-6-methoxyindan as an oily product.

NMR($CDCl_3$) δ: 1.20–1.95(8H,m), 2.20–2.38(1H,m), 2.68–2.94(3H,m), 3.01–3.15(1H,m), 3.79(3H,s), 6.67–6.78 (2H,m), 7.04–7.14(1H,m).

Reference Example 32

(E)-1-(2-Aminoethyliden)indan

In substantially the same manner as in Reference Example 1, (indan-1-ylidene)acetonitrile was produced from 1-indanone as a mixture of its isomers (yield 76%). By reducing the cyano group in substantially the same procedure as in Reference Example 3-B, the above-titled compound was obtained (yield 47%) as an oily product.

NMR($CDCl_3$) δ: 2.70–2.82(2H,m), 2.96–3.05(2H,m), 3.48(2H,d,J=7.0 Hz), 5.96–6.07(1H,m), 7.16–7.30(3H,m), 7.42–7.51(1H,m).

Reference Example 33

5,6,7-Trimethoxy-1-indanone

A mixture of 3-(3,4,5-trimethoxyphenyl)propionic acid (9.40 g, 39.1 mmol) and polyphosphoric acid (50 g) was stirred for 2 hours at 80° C. To the reaction mixture was added water, which was subjected to extraction with ethyl acetate. The extract solution was washed with brine, which was dried over anhydrous magnesium sulfate, followed by distilling off the solvent under reduced pressure. The residue was recrystallized from ethyl acetate/isopropyl ether to give 7.71 g (yield 89%) of the above-titled compound, m.p. 114–115° C.

NMR($CDCl_3$) δ: 2.61–2.70(2H,m), 2.99–3.08(2H,m), 3.86(3H,s), 3.94(3 h,s), 4.05(3H,s), 6.68(1H,s).

Reference Example 34

(E)-(5,6,7-Trimethoxyindan-1-ylidene)acetonitrile

In substantially the same manner as in Reference Example 1, the above-titled compound was produced from 5,6,7-trimethoxy-1-indanone (yield 57%). This compound was used for the subsequent reaction without purification.

Reference Example 35

(E)-1-(2-Aminoethylidene)-5,6,7-trimethoxyindan

In substantially the same manner as in Reference Example-3-B, the above-titled compound was produced from (E)-(5,6,7-trimethoxyindan-1-ylidene)acetonitrile (yield 97%) as an oily product.

NMR($CDCl_3$) δ: 1.46(2H,br s), 2.68–2.80(2H,m), 2.87–2.98(2H,m), 3.44(2H,d,J=6.8 Hz), 3.85(6H,s), 3.92 (3H,s), 6.25–6.38(1H,m), 6.56(1H,s).

Reference Example 36

(E)-Ethyl 3-(4-methoxy-3-methylphenyl)acrylate

In substantially the same manner as in Reference Example 27, the above-titled compound was produced from 4-methoxy-3-methylbenzaldehyde. This compound was used for the subsequent reaction without purification.

Reference Example 37

Ethyl 3-(4-methoxy-3-methylphenyl)propionate

In substantially the same manner as in Reference Example 14, the above-titled compound was produced from (E)-ethyl 3-(4-methoxy-3-methylphenyl)acrylate. This compound was used for the subsequent reaction without purification.

Reference Example 38

Ethyl 3-(3-Bromo-4-methoxy-5-methylphenyl) propionate

To a solution of ethyl 3-(4-methoxy-3-methylphenyl) propionate (derived from 10.0 g (66.6 mmol) of 4-methoxy-3-methylbenzaldehyde) in chloroform (200 ml) was added dropwise bromine (10.6 g, 66.6 mmol). The mixture was stirred for 12 hours at room temperature. The reaction mixture was washed with water, an aqueous solution of sodium thiosulfate, which was dried over anhydrous magnesium sulfate, followed by distilling off the solvent under reduced pressure. The residue was purified by means of a silica gel column chromatography (hexane→hexane/ethyl acetate, 9:1) to give 17.0 g (yield 85%; 3 steps) of the above-titled compound as an oily product.

NMR($CDCl_3$) δ: 1.24(3H,t,J=7.2 Hz), 2.29(3H,s), 2.57 (2H,t,J=7.0 Hz), 2.84(2H,t,J=7.0 Hz), 3.78(3H,s), 4.12(2H, q,J=7.2 Hz), 6.95(1H,d,J=1.6 Hz), 7.21(1H,d,J=1.6 Hz).

Reference Example 39

3-(3-Bromo-4-methoxy-5-methylphenyl)propionic acid

To a solution of 17.0 g (56.4 mmol) of ethyl 3-(3bromo-4-methoxy-5-methylphenyl)propionate in methanol (30 ml) was added a 8N aqueous solution of sodium hydroxide (200 ml). The mixture was stirred for 18 hours at room temperature. The reaction mixture was acidified with 5N HCl, which was subjected to extraction with chloroform. The extract solution was washed with brine, which was dried over anhydrous magnesium sulfate. The solvent was distilled off under reduced pressure to give 14.8 g (yield 96%) of the above-titled compound as an oily product.

NMR($CDCl_3$) δ: 2.30(3H,s), 2.60–2.68(2H,m), 2.81–2.89 (2H,m), 3.78(3H,s), 6.95(1H,d,J=1.8 Hz), 7.22(1H,d,J=1.8 Hz).

Reference Example 40

5-Bromo-6-methoxy-7-methyl-1-indanone and 7-bromo-6-methoxy-5-methyl-1-indanone

A mixture of 3-(3-bromo-4-methoxy-5-methylphenyl) propionic acid (14.8 g, 54.2 mmol) and polyphosphoric acid (75 g) was stirred for one hour at 80° C. The reaction mixture was cooled, to which was added water. The mixture was subjected to extraction with ethyl acetate. The extract solution was washed with brine, which was dried over anhydrous magnesium sulfate, followed by distilling off the solvent under reduced pressure. The residue was purified by means of a silica gel column chromatography (hexane/ethyl acetate, 9:1→4:1) to give 6.06 g (yield 44%) of 5-bromo-6-methoxy-7-methyl-1-indanone, m.p.76–77° C. (recrystallized from ethyl acetate/isopropyl ether).

NMR($CDCl_3$) δ: 2.62(3H,s), 2.64–2.71(2H,m), 2.99–3.06 (2H,m), 3.80(3H,s), 7.51(1H,s).

The elution of the silica gel column chromatography was continued to give 4.00 g (yield 29%) of 7-bromo-6-methoxy-5-methyl-1-indanone, m.p.108–109° C. (recrystallized from ethyl acetate/isopropyl ether).

NMR($CDCl_3$) δ: 2.41(3H,s), 2.69–2.76(2H,m), 2.96–3.03 (2H,m), 3.83(3H,s), 7.22(1H,s).

Reference Example 41

(E)-(5-Bromo-6-methoxy-7-methylindan-1-ylidene) acetonitrile

By substantially the same procedure as in Reference Example 1, the above-titled compound was produced from 5-bromo-6-methoxy-7-methyl-1-indanone (yield 34%), m.p.126–128° C. (recrystallized from ethyl acetate/ isopropyl ether).

NMR($CDCl_3$) δ: 2.45(3H,s), 2.99–3.07(2H,m), 3.10–3.20 (2H,m), 3.78(3H,s), 5.69–5.72(1H,m), 7.43(1H,s).

Reference Example 42

(E)-1-(2-Aminoethylidene)-5-bromo-6-methoxy-7-methylindan

By substantially the same procedure as in Reference Example 3-B, the above-titled compound was produced from (E)-(5-bromo-6-methoxy-7-methylindan-1-ylidene) acetonitrile (yield 97%) as an oily product.

NMR($CDCl_3$) δ: 2.47(3H,s), 2.70–2.80(2H,m), 2.85–2.93 (2H,m), 3.50(2H,d,J=7.0 Hz), 3.76(3H,s), 6.00–6.08(1H,m), 7.29(1H,s).

Reference Example 43

(E)-(7-Bromo-6-methoxy-5-methylindan-1-ylidene) acetonitrile

In substantially the same manner as in Reference Example 1, the above-titled compound was produced from 7-bromo-6-methoxy-5-methyl-1-indanone (yield 73%), m.p. 124–125° C. (recrystallized from ethyl acetate/hexane).

NMR($CDCl_3$) δ: 2.37(3H,s), 2.98–3.05(2H,m), 3.10–3.20 (2H,m), 3.80(3H,s), 6.70(1H,t,J=2.4 Hz), 7.13(1H,s).

Reference Example 44

(E)-1-(2-Aminoethylidene)-7-bromo-6-methoxy-5-methylindan

In substantially the same manner as in Reference Example 3-B, the above-titled compound was produced from (E)-(7-bromo-6-methoxy-5-methylindan-1-ylidene)acetonitrile (yield 96%) as an oily product.

NMR($CDCl_3$) δ: 2.31(3H,s), 2.73–2.82(2H,m), 2.85–2.96 (2H,m), 3.50(2H,d,J=6.8 Hz), 3.78(3H,s), 6.90–7.00(2H,m).

Reference Example 45

1-(2-Aminoethyl)-6-ethoxyindan

To a solution of 1-[2-(acetylamino)ethyl]-6-hydroxyindan (1.00 g, 4.56 mmol), ethanol (0.32 ml, 5.47 mmol) and triphenylphosphine (1.32 g, 5.02 mmol) in THF (20 ml) was added dropwise, under ice-cooling, diethyl azodicarboxylate (0.87 g, 5.02 mmol). The mixture was stirred for 15 hours at room temperature. The reaction mixture was concentrated under reduced pressure. To the concentrate was added water, and the mixture was subjected to extraction with ethyl acetate. The extract solution was washed with brine, which was dried over anhydrous magnesium sulfate. The solvent was distilled off under reduced pressure. The residue was subjected to a silica gel column chromatography (ethyl acetate→ethyl acetate/methanol, 95:5) to give 1-[2-(acetylamino)ethyl]-6-ethoxyindan. To this compound was added hydrazine hydrate (20 ml). The mixture was heated under reflux for 15 hours under argon atmosphere. The reaction mixture was cooled, to which was added water. The mixture was subjected to extraction with ethyl acetate. The extract solution was washed with brine and dried over anhydrous magnesium sulfate. The solvent was distilled off under reduced pressure to give 0.34 g (yield 36%) of the above-titled compound as an oily product.

NMR($CDCl_3$) δ: 1.40(3H,t,J=7.0 Hz), 1.52–1.78(2H,m), 1.95–2.22(1H,m), 2.23–2.39(1H,m), 2.50–2.60(3H,m), 2.72–2.96(3H,m), 3.06–3.20(1H,m), 4.01(2H,q,J=7.0 Hz), 6.66–6.76(2H,m), 7.10(1H,d,J=8.0 Hz).

Reference Example 46

1-(2-Aminoethyl)-6-(2-phenylethoxy)indan

In substantially the same manner as in Reference Example 45, 1-[2-(acetylamino)ethyl]-6-(2-phenylethoxy)indan was produced from 1-[2-(acetylamino)ethyl]-6-hydroxyindan and β-phenethyl alcohl. This product was subjected to substantially the same procedure as in Reference Example 45 to give the above-titled compound (yield 36%) as an oily product.

NMR($CDCl_3$) δ: 1.55–1.82(2H,m), 2.20–2.37(2H,m), 2.65–2.85(2H,m), 2.90–3.20(5H,m), 4.13(2H,t,J=7.2 Hz), 4.87(2H,br s), 6.68–6.76(2H,m), 7.07(1H,d,J=8.2 Hz), 7.16–7.32(5H,m).

Reference Example 47

7-Amino-1-tetralone

Under ice-cooling, 1-tetralone (15.0 g, 0.103 mol) was gradually added dropwise to fuming nitric acid (100 ml). The reaction mixture was stirred for 30 minutes, which was poured into water. Resulting crystalline precipitate was collected by filtration and washed with water, which was dissolved in ethyl acetate. The solution was washed with brine, dried over anhydrous magnesium sulfate and concentrated under reduced pressure. The residue was crystallized from ethyl acetate/isopropyl ether to give 7-nitro-1-tetralone. This compound was dissolved in ethanol (100 ml), to which 5% Pd.-C (50% hydrous, 1 g) was added. The mixture was stirred for 2 hours at room temperature under hydrogen atmosphere. The reaction mixture was subjected to filtration, and the filtrate was concentrated. The concentrate was purified by means of a silica gel column chromatography (hexane/ethyl acetate, 3:2), followed by recrystallization from ethyl acetate/isopropyl ether to give 1.70 g (yield from 1-tetralone, 10%) of the above-titled compound, m.p.141–143° C.

NMR($CDCl_3$) δ: 2.09(2H,quintet,J=6.0 Hz), 2.61(2H,t,J=6.0 Hz), 2.85(2H,t,J=3.0 Hz), 3.70(2H,br s), 6.83(1H,dd,J=2.6 Hz,8.2 Hz), 7.06(1H,d,J=8.2 Hz), 7.32(1H,d,J=2.6 Hz).

Reference Example 48

7-Formylamino-1-tetralone

To a solution of 7-amino-1-tetralone (1.70 g, 10.5 mmol) in formic acid (3 ml) was added a mixture of formic acid (8 ml) and acetic anhydride (3 ml), followed by stirring for 10 minutes at room temperature. The reaction mixture was concentrated under reduced pressure. The concentrate was neutralized with a saturated aqueous solution of sodium hydrogencarbonate, which was subjected to extraction with ethyl acetate. The extract solution was washed with brine and dried over anhydrous magnesium sulfate, followed by distilling off the solvent under reduced pressure. The residue was recrystallized from ethyl acetate/isopropyl ether to give 1.80 g (yield 91%) of the above-titled compound, m.p.137–138° C.

NMR($CDCl_3$) δ: 2.08–2.20(2H,m), 2.62–2.71(2H,m), 2.91–2.99(2H,m), 7.21–7.30(1H,m), 7.75–7.88(1.5H,m), 8.00–8.17(1.5H,m), 8.42(0.5H,d,J=1.4 Hz), 8.73(0.5H,d,J=11.4 Hz).

Reference Example 49

1-(2-Aminoethyl)-7-formylamino-1,2,3,4-tetrahydronaphthalene

By substantially the same procedure as in Reference Example 1, from 7-formylamino-1-tetralone, a cyano compound was produced as a mixture of isomers at the double bond. The cyano group of this cyano compound was reduced in substantially the same manner as in Reference Example 3-B to give the corresponding amino compound. The double bond of this amino compound was hydrogenated in substantially the same manner as in Reference Example 14 to give the above-titled compound. Yield was 99%. The compound thus obtained was used for the subsequent reaction without purification.

Reference Example 50

(E)-1-[(2-Trifluoroacetylamino)ethylidene]-1,2,3,4-tetrahydronaphthalene

By substantially the same procedure as in Working Example 1, a mixture of isomers of the above-titled compound was produced from 1-(2-aminoethylidene)-1,2,3,4-tetrahydronaphthalene and trifluoroacetic anhydride (yield 62%). The mixture was subjected to a silica gel column chromatography and recrystallization to separate the above titled compound in a pure state (yield 24%), m.p.99–102° C. (recrystallized from hexane).

NMR($CDCl_3$) δ: 1.86(2H,m), 2.57(2H,t,J=6.3 Hz), 2.80 (2H,t,J=6.1 Hz), 4.18(2H,t,J=6.3 Hz), 5.96(1H,br t,J=7.1 Hz), 6.37(1H,br s), 7.05–7.30(3H,m), 7.50–7.60(1H,m).

Elemental Analysis for $C_{14}H_{14}F_3NO$: Calcd.: C, 62.45; H, 5.24; N, 5.20; F, 21.17. Found: C, 62.34; H, 5.24; N, 5.22; F, 21.29.

Reference Example 51

1-[(2-Acetylamino)ethylidene]-1,2,3,4-tetrahydronaphthalene

By substantially the same procedure as in Working Example 1, a mixture of isomers of the above-titled compound was produced from 1-(2-aminoethylidene)-1,2,3,4-tetrahydronaphthalene and acetyl chloride (yield 68%), m.p62–65° C. (recrystallized from ethyl acetate/hexane)

NMR($CDCl_3$) δ: 1.75–2.05(5H,m), 2.50–2.80(4H,m), 3.30–4.10(2H,m), 5.65(1H,br s), 5.85–6.05(1H,m), 7.00–7.60(4H,m).

Elemental Analysis for $C_{14}H_{17}NO$: Calcd.: C, 78.10; H, 7.96; N, 6.51. Found: C, 78.22; H, 7.91; N, 6.66.

Reference Example 52

1-[2-(4-Nitrobenzoylamino)ethylidene]-1,2,3,4-tetrahydronaphtalene

By substantially the same procedure as in Working Example 1, a mixture of isomers of the above-titled compound was produced from 1-(2-aminoethylidene)-1,2,3,4-tetrahydronaphthalene and p-nitrobenzoyl chloride (yield 78%), m.p.138–139° C. (recrystallized from ethyl acetate/hexane).

NMR($CDCl_3$) δ: 1.80–2.00(2H,m), 2.50–2.90(4H,m), 3.60–4.40(2H,m), 5.90–6.20(1H,m), 6.25–6.45(1H,br s), 7.10–8.40(8H,m).

Elemental Analysis for $C_{19}H_{18}N_2O_3$: Calcd.: C, 70.79; H, 5.63; N, 8.69. Found: C, 70.76; H, 5.59; N, 8.70.

Reference Example 53

1-[2-(4-Trifluoroacetylaminobenzoylamino)ethyl]-1,2,3,4-tetrahydronaphthalene

By substantially the same procedure as in Reference Example 11 and Working Example 1, the above-titled compound was produced from 1-(2aminoethylidene)-1,2,3,4-tetrahydronaphthalene and trifluoroacetic anhydride (yield 68%), m.p.165–167° C. (recrystallized from ethyl acetate).

NMR($CDCl_3$) δ: 1.60–2.10(6H,m), 2.70–2.80(2H,m), 2.82–3.00(1H,m), 3.50–3.70(2H,m), 6.15–6.23(1H,br s), 7.02–7.20(4H,m), 7.60–7.78(4H,m), 8.52(1H,br s).

Elemental Analysis for $C_{21}H_{21}F_3N_2O_2$: Calcd.: C, 64.61; H, 5.42; N, 7.18; F, 14.60. Found: C, 64.62; H, 5.39; N, 7.23; F, 14.58.

Reference Example 54

(E)-1-[2-(Trifluoroacetylamino)ethylidene]indan

By substantially the same procedure as in Working Example 1, the above-titled compound was produced from (E)-1-(2-aminoethylidene)indan and trifluoroacetic anhydride (yield 22%), m.p.101–103° C. (recrystallized from isopropyl ether/hexane).

NMR($CDCl_3$) δ: 2.76–2.85(2H,m), 3.01–3.09(2H,m), 4.15(2H,t,J=6.4 Hz), 5.84–5.96(1H,m), 6.39(1H,br s), 7.18–7.24(3H,m), 7.41–7.50(1H,m).

Elemental Analysis for $C_{13}H_{12}F_3NO$: Calcd.: C, 61.18; H, 4.74; N, 5.49. Found: C, 61.21; H, 4.74; N, 5.54

Reference Example 55

1-[2-(Trifluoroacetylamino)ethyl]indan

By substantially the same procedure as in Working Example 11, the above-titled compound was produced from (E)-1-[2-(trifluoroacetylamino)ethylidene]indan (yield 76%), m.p.67–68° C. (recrystallized from isopropyl ether/hexane).

NMR($CDCl_3$) δ: 1.64–1.82(2H,m), 2.07–2.42(2H,m), 2.79–3.06(2H,m), 3.12–3.23(1H,m), 3.51(2H,q,J=7.0 Hz), 6.32(1H,br s), 7.20(4H,s).

Elemental Analysis for $C_{13}H_{14}F_3NO$: Calcd.: C, 60.70; H, 5.49; N, 5.44. Found: C, 60.60; H, 5.24; N, 5.49

Reference Example 56

4-(3-Bromopropyl)-6-methoxy-1,2-dihydronaphthalene

To a suspension of magnesium (2.9 g) in THF (100 ml) was added bromocyclopropane (14.4 g, 11.9 mmol) dropwise at 0° C. under argon atmosphere. The mixture was stirred for 30 minutes at room temperature and then a solution of 7-methoxy-1-tetralone (15 g, 85.1 mmol) in THF (50 ml) was added. The mixture was refluxed for 2 hours and then cooled. Saturated aqueous ammonium chloride was introduced and the product was extracted with ethyl acetate. The extract was washed with brine and water, dried over anhydrous magnesium sulfate, and the solvent was removed in vacuo. The residue was dissolved in acetic acid (100 ml) and 20% hydrobromic acid (75 ml) was added. The mixture was stirred for 15 hours at room temperature and then concentrated. To the residue was added saturated aqueous sodium hydrogen bicarbonate and the product was extracted with ethyl acetate. The extract was washed with brine and water, dried over anhydrous magnesium sulfate, and the solvent removed in vacuo. The residue was purified by a silica gel column chromatography (ethyl acetate:hexane=1:9) to afford the titled compound (20 g, yield 84%, oil).

NMR($CDCl_3$) δ: 2.00–2.15(2H,m), 2.17–2.30(2H,m), 2.55–2.70(4H,m), 3.45(2H,t,J=6.6 Hz), 3.80(3H,s), 5.94 (1H,t,J=4.4 Hz), 6.69(1H,dd,J=2.6 Hz,8.1 Hz), 6.83(1H,d, J=2.6 Hz), 7.06(1H,d,J=8.1 Hz).

Elemental Analysis For $C_{14}H_{17}BrO$ Calcd.: C, 59.80; H, 6.09. Found: C, 59.77; H, 6.32.

Reference Example 57

2-[3-(7-Methoxy-3,4-dihydronaphthalen-1-yl)propyl]isoindole-1,3-dione

A mixture of 4-(3-bromopropyl)-6-methoxy-1,2-dihydronaphthalene (10 g, 35.6 mmol), potassium phthalimide (7.9 g, 42.7 mmol) and DMF (50 ml ) was heated at 100° C. for 1 hour and then cooled. The mixture was diluted with water and the product was extracted with ethyl acetate. The extract was washed with brine and water, dried over anhydrous magnesium sulfate, and the solvent was removed in vacuo. The residue was purified by a silica gel column chromatography (ethyl acetate:hexane=2:8) to afford the titled compound (11.8 g, yield 95%, oil).

NMR($CDCl_3$) δ: 1.95(2H,m), 2.12–2.27(2H,m), 2.48(2H, t,J=7.7 Hz), 2.63(2H,t,J=7.7 Hz), 3.70–3.93(5H,m), 5.92 (1H,t,J=4.6 Hz), 6.67(1H,dd,J=2.6 Hz,8.1 Hz), 6.78(1H,d, J=2.6 Hz), 7.03(1H,d,J=8.1 Hz), 7.65–7.90(4H,m).

Elemental Analysis for $C_{22}H_{21}NO_3$: Calcd.: C, 76.06; H, 6.09; N, 4.03. Found: C, 76.23; H, 6.23; N, 3.99.

Reference Example 58

3-(7-Methoxy-3,4-dihydronaphthalen-1-yl)propylamine

A solution of 2-[3-(7-methoxy-3,4-dihydronaphthalen-1-yl)propyl]isoindole-1,3-dione (11.8 g, 34.0 mmol) and hydrazine monohydrate (5.1 g, 0.1 mol) in ethanol (150 ml) was refluxed for 1 hour and then cooled in an ice bath. The resulting insoluble material was removed by filtration and the solvent was removed in vacuo to afford the titled compound (5.7 g, yield 77%, oil). This compound was provided for the next reaction without further purification.

NMR($CDCl_3$) δ: 1.68(2H,m), 2.15–2.30(2H,m), 2.46(2H, t,J=7.5 Hz), 2.60–2.80(4H,m), 3.80(3H,s), 5.89(1H,t,J=4.4 Hz), 6.68(1H,dd,J=2.4 Hz,8.2 Hz), 6.83(1H,d,J=2.4 Hz), 7.06(1H,d,J=8.2 Hz).

Reference Example 59

4-[3-(Trifluoroacetylamino)propyl]-6-methoxy-1,2-dihydronaphthalene

By substantially the same procedure as in Working Example 1, the above-titled compound was prepared from 3-(7-methoxy-3,4-dihydronaphthalen-1-yl)propylamine and trifluoroacetic anhydride (yield 87%, oil).

NMR($CDCl_3$) δ: 1.84(2H,m), 2.16–2.30(2H,m), 2.50(2H, t,J=6.8 Hz), 2.67(2H,t,J=7.9 Hz), 3.40(2H,q,J=6.6 Hz), 3.80 (3H,s), 5.91(1H,t,J=4.6 Hz), 6.35(1H,br s), 6.70(1H,dd,J= 2.8 Hz,8.2 Hz), 6.77(1H,d,J=2.8 Hz), 7.07(1H,d,J=8.2 Hz).

Elemental Analysis for $C_{16}H_{18}F_3NO_2$: Calcd.: C, 61.34; H, 5.79; N,4.47; F, 18.19. Found: C, 61.22; H, 5.77; N, 4.63; F, 18.22.

Reference Example 60

4-[3-(Acetylamino)propyl]-6-methoxy-1,2-dihydronaphthalene

By substantially the same procedure as in Working Example 1, the above-titled compound was prepared from 3-(7-methoxy-3,4-dihydronaphthalen-1-yl)propylamine and acetyl chloride (yield 90%, oil).

NMR($CDCl_3$) δ: 1.75(2H,m), 1.95(3H,s), 2.13–2.30(2H, m), 2.46(2H,t,J=7.4 Hz), 2.66(2H,t,J=7.9 Hz), 3.29(2H,q,J= 6.5 Hz), 3.80(3H,s), 5.50(1H,br s), 5.89(1H,t,J=4.4 Hz), 6.69(1H,dd,J=2.2 Hz,8.1 Hz), 6.79(1H,d,J=2.2 Hz), 7.07 (1H,d,J=8.1 Hz).

Elemental Analysis for $C_{16}H_{21}NO_2$: Calcd.: C, 74.10; H, 8.16; N, 5.40. Found: C, 74.23; H, 8.21; N, 5.33.

Reference Example 61

4-(3-Cyanopropyl)-6-methoxy-1,2-dihydronaphthalene

A mixture of 4-(3-bromopropyl)-6-methoxy-1,2-dihydronaphthalene (10 g, 35.6 mmol), sodium cyanide (1.92 g, 39.1 mmol) and dimethyl sulfoxide (20 ml) was stirred for 1 hour at room temperature. The mixture was diluted with water and the product was extracted with ethyl acetate. The extract was washed with brine and water, dried over anhydrous magnesium sulfate, and the solvent was removed in vacuo. The residue was purified by silica gel column chromatography (ethyl acetate:hexane=1:9) to afford the titled compound (7.5 g, yield 93%, oil).

NMR($CDCl_3$) δ: 1.80–1.98(2H,m), 2.18–2.30(2H,m), 2.35(2H,t,J=7.0 Hz), 2.50–2.75(4H,m), 3.80(3H,s), 5.95 (1H,t,J=4.6 Hz), 6.70(1H,dd,J=2.6 Hz,8.1 Hz), 6.78(1H,d, J=2.6 Hz), 7.07(1H,d,J=8.1 Hz).

Elemental Analysis for $C_{15}H_{17}NO$: Calcd.: C,79.26; H, 7.54; N, 6.16. Found: C, 79.23; H, 7.66; N, 6.36.

Reference Example 62

4-(4-Aminobutyl)-6-methoxy-1,2-dihydronaphthalene

By substantially the same procedure as in Reference Example 2, the above-titled compound was prepared from 4-(3-cyanopropyl)-6-methoxy-1,2-dihydronaphthalene (yield 90%, oil).

NMR($d_6$-DMSO) δ:1.30–1.60(4H,m), 2.05–2.67(10H, m), 3.73(3H,s), 5.87(1H,t,J=4.0 Hz), 6.70(1H,dd,J=2.0 Hz,8.1 Hz), 6.76(1H,d,J=2.0 Hz), 7.05(1H,d,J=8.1 Hz).

Reference Example 63

4-[4-(Trifluoroacetylamino)butyl]-6-methoxy-1,2-dihydronaphthalene

By substantially the same procedure as in Working Example 1, the above-titled compound was prepared from 4-(4-aminobutyl)-6-methoxy-1,2-dihydronaphthalene and trifluoroacetic anhydride (yield 97%, oil).

NMR($CDCl_3$) δ: 1.40–1.70(4H,m), 2.15–2.30(2H,m), 2.38–2.55(2H,m), 2.67(2H,t,J=7.9 Hz), 3.30–3.42(2H,m), 3.80(3H,s), 5.87(1H,t,J-4.6 Hz), 6.27(1H,br s), 6.69(1H,dd, J=2.6 Hz,8.1 Hz), 6.78(1H,d,J=2.6 Hz), 7.07(1H,d,J=8.1 Hz).

Elemental Analysis for $C_{17}H_{20}F_3NO_2$: Calcd.: C, 62.38; H, 6.16; N, 4.28; F,17.41. Found: C, 61.94; H, 6.14; N, 4.14; F,17.45.

Reference Example 64

4-[4-(Acetylamino)butyl]-6-methoxy-1,2-dihydronaphthalene

By substantially the same procedure as in Working Example 1, the above-titled compound was prepared from 4-(7-methoxy-3,4-dihydronaphthalen-1-yl)butylamine and acetyl chloride (yield 95%), m.p. 79–81° C. (recrystallized from ethyl acetate/hexane).

NMR($CDCl_3$) δ: 1.49–1.62(4H,m), 1.95(3H,s), 2.14–2.30 (2H,m), 2.36–2.50(2H,m), 2.66(2H,t,J=8.1 Hz), 3.20–3.33 (2H,m), 3.80(3H,s), 5.44(1H,br s), 5.87(1H,t,J=4.4 Hz), 6.68(1H,dd,J=2.4 Hz,8.2 Hz), 6.80(1H,d,J=2.4 Hz), 7.06 (1H,d,J=8.2 Hz).

Elemental Analysis for $C_{17}H_{23}NO_2$: Calcd.: C, 74.69; H, 8.48; N, 5.12. Found: C, 74.66; H, 8.30; N, 5.01.

Reference Example 65

(E)-(6-Methoxy-2-phenylindan-1-ylidene) acetonitrile

By substantially the same procedure as in Reference Example 23, the above-titled compound was prepared from 6-methoxy-2-phenyl-1-indanone(yield 16%), m.p. 112–114° C. (recrystallized from ethyl acetate/isopropyl ether).

NMR($CDCl_3$) δ: 3.03(1H,d,J=17.0 Hz), 3.59(1H,dd,J=8.2 Hz,17.0 Hz), 3.86(3H,s), 4.49(1H,d,J=8.2 Hz), 5.69(1H,d, J=2.6 Hz), 6.95–7.32(8H,m).

Reference Example 66

3-(2-Aminoethyl)-5-methoxy-2-phenyl-1H-indene hydrochloride

By substantially the same procedure as in Reference Example 3-B, the free base of the titled compound was prepared from (E)-(6-Methoxy-2phenylindan-1-ylidene) acetonitrile. The above-titled compound was prepared from the free base and HCl/ethanol (yield 58%), amorphous. The compound thus obtained was used for the subsequent reaction without purification.

Reference Example 67

5-Methoxy-2-phenyl-3-[2-(trifluoroacethylamino) ethyl]-1H-indene

By substantially the same procedure as in Working Example 1, the above-titled compound was prepared from 3-(2-Aminoethyl)-5-methoxy-2-phenyl-1H-indene hydrochloride and trifluoroacetic anhydride (yield 92%), m.p. 138–139° C. (recrystallized from ethyl acetate/hexane).

NMR($CDCl_3$) δ: 3.03(2H,t,J=7.2 Hz), 3.61(2H,q,J=7.2 Hz), 3.71(2H,s), 3.88(3H,s), 6.29(1H,broad s), 6.81(1H,dd, J=2.2 Hz,8.4 Hz), 7.03(1H,d,J=2.2 Hz), 7.39(1H,d,J=8.4 Hz), 7.40(5H,s).

Elemental Analysis for $C_{20}H_{18}F_3NO_2$: Calcd.: C, 66.48; H, 5.02; N, 3.88. Found: C, 66.23; H, 4.90; N, 3.65.

Working Example 1

(E)-1-[2-(Acetylamino)ethylidene]-7-methoxy-1,2,3, 4-tetrahydronaphthalene

To a solution of 1-(2-aminoethylidene)-7-methoxy-1,2,3, 4-tetrahydronaphthalene (2.0 g, 9.74 mmol) and triethylamine (1.5 g, 14,6 mmol) in THF (20 ml) was gradually added dropwise, under ice-cooling, acetyl chloride (0.76 g, 9.74 mmol). The mixture was stirred for 30 minutes at room temperature. The reaction mixture was poured into water, and the organic layer was subjected to extraction with chloroform. The extract solution was washed with brine and water, which was dried over anhydrous magnesium sulfate. The solvent was then distilled off under reduced pressure. The residue was purified by means of a silica gel column chromatography (ethyl acetate), followed by recrystallization from ethyl acetate/hexane to give the above-titled compound (yield 0.96 g, 40%).

m.p.92–94° C. (recrystallized from ethyl acetate/hexane)

NMR($CDCl_3$) δ: 1.73–1.90(2H,m), 2.01(3H,s), 2.51(2H, t,J=5.8 Hz), 2.71(2H,t,J=6.2 Hz), 3.80(3H,s), 4.06(2H,t,J= 6.2 Hz), 5.62(1H,br s), 5.94(1H,m), 6.75(1H,dd,J=2.6 Hz,8.4 Hz), 7.01(1H,d,J=8.4 Hz), 7.06(1H,d,J=2.6 Hz).

Elemental Analysis for $C_{15}H_{19}NO_2$: Calcd.: C, 73.44; H, 7.81; N, 5.71. Found: C, 73.52; H, 7.86; N, 5.73.

Working Example 2

(Z)-1-[2-(Acetylamino)ethylidene]-7-methoxy-1,2,3, 4-tetrahydronaphthalene

In substantially the same manner as in Working Example 1, a mixture of isomers of the above-titled compound was produced from 1-(2-aminoethylidene)-7-methoxy-1,2,3,4-tetrahydronaphthalene and acetyl chloride. This mixture of isomers was purified by means of a silica gel column chromatography (ethyl acetate:hexane=6:4) to give the above-titled compound (yield 30%).

m.p.71–73° C.

NMR($CDCl_3$) δ: 1.81–1.97(2H,m), 2.42(2H,d,J=6.6 Hz), 2.75(2H,t,J=6.6 Hz), 3.79(3H,s), 4.19(2H,t,J=6.0 Hz), 5.41 (1H,t,J=6.8 Hz), 5.60(1H,br s), 6.72–6.82(2H,m), 7.05(1H, d,J=8.4 Hz).

Working Example 3

(E)-1-[2-(Cyclopropylcarbonylamino)ethylidene]-7-methoxy-1,2,3,4-tetrahydronaphthalene In substantially the same manner as in Working Example 1, the above-titled compound was produced from 1-(2-aminoethylidene)-7-methoxy-1,2,3,4-tetrahydronaphthalene and cyclopropanecarbonyl chloride (yield 59%).

m.p.130–132° C. (recrystallized from ethyl acetate/ hexane)

NMR($CDCl_3$) δ: 0.70–0.82(2H,m), 0.90–1.08(2H,m), 1.25–1.43(1H,m), 1.81(2H,m), 2.52(2H,t,J=5.5 Hz), 2.71 (2H,t,J=6.2 Hz), 3.80(3H,s), 4.09(2H,t,J=6.2 Hz), 5.71,1H, br s), 5.96(1H,m), 6.75(1H,dd,J=2.6 Hz,8.4 Hz), 7.01(1H, d,J=8.4 Hz), 7.07(1H,d,J=2.6 Hz).

Elemental Analysis for $C_{17}H_{21}NO_2$: Calcd.: C, 75.25; H, 7.80; N, 5.16. Found: C, 75.02; H, 7.85; N, 5.05.

Working Example 4

(E)-1-[2-(Valerylamino)ethylidene]-7-methoxy-1,2, 3,4-tetrahydronaphthalene

In substantially the same manner as in Working Example 1, the above-titled compound was produced from 1-(2-aminoethylidene)-7-methoxy-1,2,3,4-tetrahydronaphthalene and valeryl chloride (yield 54%).

m.p.64–66° C.

NMR($CDCl_3$) δ: 0.92(3H,t,J=7.2 Hz), 1.25–1.45(2H,m), 1.50–1.90(4H,m), 2.20(2H,t,J=7.6 Hz), 2.52(2H,t,J=5.9 Hz), 2.71(2H,t,J=6.2 Hz), 3.80(3H,s), 4.07(2H,t,J=6.2 Hz), 5.50(1H,br s), 5.94(1H,t,J=7.0 Hz), 6.75(1H,dd,J=2.6 Hz,8.4 Hz), 7.01(1H,d,J=8.4 Hz), 7.06(1H,d,J=2.6 Hz).

Elemental Analysis for $C_{18}H_{25}NO_2$: Calcd.: C, 75.22; H, 8.77; N, 4.87. Found: C, 74.92; H, 8.79; N, 4.79.

Working Example 5

(E)-1-[2-[3-(4-Methoxyphenyl)ureido]ethylidene]-7-methoxy-1,2,3,4-tetrahydronaphthalene To a solution of 1-(2-aminoethylidene)-7-methoxy-1,2,3, 4-tetrahydronaphthalene (3.0 g, 14.8 mmol) in THF (20 ml) was gradually added dropwise, under ice cooling, 4-methoxyphenyl isocyanate (2.2 g, 14.8 mmol). The mixture was stirred for 30 minutes at room temperature. The reaction mixture was then poured into water. The organic layer was subjected to extraction with 10% methanol/ chloroform. The extract solution was washed with brine and water, which was dried over anhydrous magnesium sulfate, followed by distilling off the solvent under reduced pressure. The residue was purified by means of a silica gel column chromatography (ethyl acetate:hexane=6:4), followed by recrystallization from ethyl acetate/methanol to give the above-titled compound (2.8 g, yield 54%).

m.p.168–170° C. (recrystallized from ethyl acetate/ methanol)

NMR($CDCl_3$) δ: 1.77(2H,m), 2.47(2H,t,J=5.9 Hz), 2.68 (2H,t,J=6.0 Hz), 3.78(6H,s), 4.03(2H,t,J=5.9 Hz), 4.85(1H, br s), 5.93(1H,t,J=6.5 Hz), 6.38(1H,br s), 6.73(1H,dd,J=2.6 Hz,8.4 Hz), 6.84(2H,d,J=9.0 Hz), 6.99(1H,d,J=8.4 Hz), 7.04 (1H,d,J=2.6 Hz), 7.17(2H,d,J=9.0 Hz).

Elemental Analysis for $C_{21}H_{24}N_2O_3$: Calcd.: C, 71.57; H, 6.86; N, 7.95. Found: C, 71.55; H, 6.82; N, 7.93.

Working Example 6

(E)-1-[2-[3-(2,4-Dimethoxyphenyl)ureido] ethylidene]-7-methoxy-1,2,3,4-tetrahydronaphthalene In substantially the same manner as in Working Example 5, the above-titled compound was produced from 1-(2-aminoethylidene)-7-methoxy-1,2,3,4-tetrahydronaphthalene and 2,4-dimethoxyphenyl isocyanate (yield 34%).

m.p.140–143° C. (recrystallized from ethyl acetate)

NMR($CDCl_3$) δ: 1.70–1.88(2H,m), 2.51(2H,t,J=6.2 Hz), 2.70(2H,t,J=6.2 Hz), 3.77(3H,s), 3.78(3H,s), 3.79(3H,s), 4.08(2H,br s), 4.80(1H,br s), 5.98(1H,t,J=6.6 Hz), 6.40–6.55 (3H,m), 6.74(1H,dd,J=2.6 Hz,8.1 Hz), 7.00(1H,d,J=8.1 Hz), 7.07(1H,d,J=2.6 Hz), 7.69(1H,d,J=9.5 Hz).

Elemental Analysis for $C_{22}H_{26}N_2O_4$: Calcd.: C, 69.09; H, 6.85; N, 7.32. Found C, 69.17; H, 6.89; N, 7.42.

Working Example 7

1-[2-(Acetylamino)ethyl]-6-methoxyindan

To a solution of 1-(2-aminoethyl)-6-methoxyindan (0.80 g, 4.18 mmol) and triethylamine (0.44 g, 4.39 mmol) in dichloromethane (15 ml) was gradually added dropwise, under ice cooling, acetyl chloride (0.33 g, 4.18 mmol). The mixture was stirred for 10 minutes at room temperature. The reaction mixture was poured into water. The organic layer was subjected to extraction with chloroform. The extract solution was washed with 1N hydrochloric acid, a saturated aqueous solution of sodium hydrogencarbonate and brine, which was dried over anhydrous magnesium sulfate, followed by distilling off the solvent under reduced pressure. The residue was recrystallized from ethyl acetate/isopropyl ether to give the above-titled compound (yield 0.68 g, 70%).

m.p.73–74° C. (recrystallized from ethyl acetate/isopropyl ether)

NMR($CDCl_3$) δ: 1.50–1.80(2H,m), 1.93–2.15(1H,m), 1.97(3H,s), 2.22–2.40(1H,m), 2.68–2.86(2H,m), 3.05–3.18 (1H,m), 3.33(2H,q,J=5.8 Hz), 3.78(3H,s), 5.49(1H,br s), 6.67–6.76(2H,m), 7.11(1H,d,J=8.0 Hz).

Elemental Analysis for $C_{14}H_{19}NO_2$: Calcd.: C, 72.07; H, 8.21; N, 6.00. Found: C, 72.16; H, 7.94; N, 6.17.

Working Example 8

1-[2-(Trifluoroacetylamino)ethyl]-6-methoxyindan

In substantially the same manner as in Working Example 1, the above-titled compound was produced from 1-(2-aminoethyl)-6-methoxyindan and trifluoroacetic anhydride (yield 68%).

m.p.66–67° C. (recrystallized from isopropyl ether/hexane)

NMR($CDCl_3$) δ: 1.60–1.80(2H,m), 2.02–2.20(1H,m), 2.24–2.41(1H,m), 2.77–2.96(2H,m), 3.05–3.21(1H,m), 3.50 (2H,q,J=7.2 Hz), 3.79(3H,s), 6.32(1H,br s), 6.70–6.77(2H, m), 7.12(1H,d,J=8.4 Hz).

Elemental Analysis for $C_{14}H_{16}F_3NO_2$: Calcd.: C, 58.53; H, 5.61; N, 4.88. Found: C, 58.30; H, 5.41; N, 5.08.

Working Example 9

1-[2-(Cyclopropylcarbonylamino)ethyl]-6-methoxyindan

In substantially the same manner as in Working Example 1, the above-titled compound was produced from 1-(2-aminoethyl)-6-methoxyindan and cyclopropanecarbonyl chloride (yield 78%).

m.p.105–106° C. (recrystallized from ethyl acetate/isopropyl ether)

NMR($CDCl_3$) δ: 0.68–0.77(2H,m), 0.93–1.02(2H,m), 1.24–1.38(1H,m), 1.55–1.80(2H,m), 1.99–2.15(1H,m), 2.25–2.41(1H,m), 2.70–2.92(2H,m), 3.06–3.20(1H,m), 3.38–3.46(2H,m), 3.79(3H,s), 5.63(1H,br s), 6.69–6.77(2H, m), 7.11(1H,d,J=8.0 Hz).

Elemental Analysis for $C_{16}H_{21}NO_2$: Calcd.: C, 74.10; H, 8.16; N, 5.40. Found: C, 73.90; H, 7.89; N, 5.44.

Working Example 10

1-[2-(Valerylamino)ethyl]-6-methoxyindan

In substantially the same manner as in Working Example 1, the above-titled compound was produced from 1-(2-aminoethyl)-6-methoxyindan and valeryl chloride (yield 56%).

m.p.66–67° C. (recrystallized from isopropyl ether/hexane)

NMR($CDCl_3$) δ: 0.91(3H,t,J=7.0 Hz), 1.23–1.42(2H,m), 1.51–1.80(4H,m), 1.97–2.20(3H,m), 2.23–2.40(1H,m), 2.69–2.95(2H,m), 3.06–3.19(1H,m), 3.35–3.44(2H,m), 3.79 (3H,s), 5.45(1H,br s), 6.70–6.79(2H,m), 7.11(1H,d,J=8.4 Hz).

Elemental Analysis for $C_{17}H_{25}NO_2$: Calcd.: C, 74.14; H, 9.15; N, 5.09. Found: C, 73.93; H, 9.00; N, 5.16.

Working Example 11

1-[2-(Acetylamino)ethyl]-7-methoxy-1,2,3,4-tetrahydronaphthalene

To a solution of (E)-1-[2-(acetylamino)ethylidene]-7-methoxy-1,2,3,4tetrahydronaphthalene (2.55 g, 10 mmol) in ethanol (20 ml) was added 5% palladium/carbon (50% hydrous, 400 mg). The mixture was subjected to catalytic reduction at normal pressure under hydrogen atmosphere. After the completion of hydrogenation, the palladium/carbon was then filtered off, and the solvent was distilled off under reduced pressure. The residue was purified by means of a silica gel column chromatography (chloroform:methanol=98:2) to give the above-titled compound (2.2 g, yield 86%, oil).

NMR($CDCl_3$) δ: 1.60–2.10(6H,m), 1.96(3H,s), 2.68(2H, t,J=5.1 Hz), 2.80(1H,m), 3.36(2H,m), 3.78(3H,s), 5.50(1H, br s), 6.64–6.72(2H,m), 6.98(1H,d,J=9.2 Hz).

Working Example 12

1-[2-(Cyclopropylcarbonylamino)ethyl]-7-methoxy-1,2,3,4-tetrahydronaphthalene

To a solution of (1,2,3,4-tetrahydro-7-methoxy-1-naphthylidene)acetonitrile (1.0 g, 5.02 mmol) in ethanol (10 ml) were added a saturated ammonia/ethanol solution (5 ml) and Raney nickel (W-2, 1 g). The mixture was stirred for 4 hours at 50° C. under hydrogen atmosphere (3–4 kgf/$cm^2$). The Raney nickel was filtered off and, then, the solvent was distilled off under reduced pressure to give 1-(2-aminoethyl)-7-methoxy-1,2,3,4-tetrahydronaphthalene. To a solution of this 1-(2-aminoethyl)-7-methoxy-1,2,3,4-tetrahydronaphthalene and triethylamine (0.76 g, 7.53 mmol) in THF (20 ml) was gradually added dropwise, under ice-cooling, cyclopropanecarbonyl chloride (0.63 g, 6.02 mmol). The mixture was stirred for 30 minutes at room temperature. The reaction mixture was poured into water. The organic layer was subjected to extraction with chloroform. The extract solution was washed with brine and water, which was then dried over anhydrous magnesium sulfate, followed by distilling off the solvent. The residue was purified by means of a silica gel column chromatography (ethyl acetate:hexane=2:8) to give the above-titled compound (1.04 g, yield 76%, oil).

NMR($CDCl_3$) δ: 0.70–0.80(2H,m), 0.92–1.06(2H,m), 1.22–1.41(1H,m), 1.60–2.10(6H,m), 2.62–2.90(3H,m), 3.32–3.50(2H,m), 3.78(3H,s), 5.66(1H,br s), 6.64–6.74(2H, m), 6.98(1H,d,J=8.7 Hz).

Working Example 13

1-[2-(Isobutyrylamino)ethyl]-7-methoxy-1,2,3,4-tetrahydronaphthalene

In substantially the same manner as in Working Example 12, the above-titled compound was produced from (1,2,3,4-tetrahydro-7-methoxy-1-naphthylidene)acetonitrile and isobutyryl chloride (yield 72%).

m.p.47–49° C.

NMR($CDCl_3$) δ: 1.13(6H,d,J=6.0 Hz), 1.60–2.00(6H,m), 2.28–2.39(1H,m), 2.62–2.90(3H,m), 3.30–3.46(2H,m), 3.78 (3H,s), 5.45(1H,br s), 6.64–6.73(2H,m), 6.98(1H,d,J=9.5 Hz).

Elemental Analysis for $C_{17}H_{25}NO_2$: Calcd.: C, 74.14; H, 9.15; N, 5.09. Found: C, 73.98; H, 9.09; N, 5.22.

Working Example 14

1-[2-[3-(4-Methoxyphenyl)ureido]ethyl]-7-methoxy-1,2,3,4-tetrahydronaphthalene

In substantially the same manner as in Working Example 11, the above-titled compound was produced from (E)-1-[2-[3-(4-methoxyphenyl)ureido]ethylidene]-7-methoxy-1,2,3,4-tetrahydronaphthalene (80%).

m.p.123–125° C. (recrystallized from ethyl acetate/hexane)

NMR($CDCl_3$) δ: 1.60–1.90(6H,m), 2.66(2H,t,J=4.6 Hz), 2.78(1H,m), 3.34(2H,m), 3.75(3H,s), 3.78(3H,s), 4.76(1H, br s), 6.36(1H,br s), 6.62–6.70(2H,m), 6.85(2H,d,J=8.8 Hz), 6.92–7.00(1H,m), 7.16(2H,d,J=8.8 Hz).

Elemental Analysis for $C_{21}H_{26}N_2O_3$: Calcd.: C, 71.16; H, 7.39; N, 7.90. Found: C, 70.96; H, 7.37; N, 7.91.

Working Example 15

1-[(2-(Acetylamino)ethylidene]-7-methoxy-2,2-dimethyl-1,2,3,4-tetrahydronaphthalene In substantially the same manner as in Working Example 1, a mixture of isomers of the above-titled compound was produced from 1-(2-aminoethylidene)-7-methoxy-2,2-dimethyl-1,2,3,4-tetrahydronaphthalene and acetyl chloride (yield 78%, oil).

NMR($CDCl_3$) δ: 1.09(4H,s,Z-isomer), 1.32(2H,s,E-isomer), 1.57(0.67H,t,J=6.0 Hz,E-isomer), 1.63(1.33H,t,J=6.8 Hz,Z-isomer), 2.00(2H,s,Z-isomer), 2.02(2H,s,E-isomer), 2.61(0.67H,t,J=6.0 Hz,E-isomer), 2.75(1.33H,t,J=6.8 Hz,Z-isomer), 3.79(2H,s,Z-isomer), 3.80(1H,s,E-isomer), 4.18(1.33H,t,J=7.0 Hz,Z-isomer), 4.28(0.67H,d,J=7.3 Hz,E-isomer), 5.43(0.67H,t,J=7.0 Hz,Z-isomer), 5.55 (1H,br s), 5.76(0.33H,t,J=7.3 Hz,E-isomer), 6.62–7.07(3H, m,E-isomer+Z-isomer).

Working Example 16

1-[2-(Acetylamino)ethyl]-7-methoxy-2,2-dimethyl-1,2,3,4-tetrahydronaphthalene

In substantially the same manner as in Working Example 11, the above-titled compound was produced from 1-[2-(acetylamino)ethylidene]-7-methoxy-2,2-dimethyl-1,2,3,4-tetrahydronaphthalene (yield 91%, oil).

NMR($d_6$-DMSO) δ: 0.81(3H,s), 0.97(3H,s), 1.18–1.43 (2H,m), 1.58–1.90(2H,m), 1.80(3H,s), 2.21(1H,dd,J=2.9 Hz,8.8 Hz), 2.60–2.73(2H,m), 3.06(2H,q,J=7.0 Hz), 3.71 (3H,s), 6.63–7.02(3H,m), 7.87(1H,t,J=5.2 Hz).

Working Example 17

(E)-9-[2-(Trifluoroacetylamino)ethylidene]-2-methoxy-6,7,8,9-tetrahydro-5H-benzocycloheptene In substantially the same manner as in Working Example 1, the above-titled compound was produced from (E)-9-(2-aminoethylidene)-2-methoxy-6,7,8,9-tetrahyro-5H-benzocycloheptene and trifluoroacetic anhydride (1.97 g, yield 91%). A portion of this compound was recrystallized from isopropyl ether-hexane to give a crystalline product, m.p.101–103° C.

NMR($CDCl_3$) δ: 1.69–1.79(4H,m), 2.39–2.47(2H,m), 2.65–2.71(2H,m), 3.80(3H,s), 5.45(2H,t,J=7.0 Hz), 6.36 (1H,br s), 6.68–6.75(2H,m), 7.00(1H,d,J=8.0 Hz).

Elemental Analysis for $C_{16}H_{18}F_3NO_2$: Calcd.: C, 61.34; H, 5.79; N, 4.47. Found: C, 61.29; H, 5.69; N, 4.55.

Working Example 18

9-[2-(Trifluoroacetylamino)ethyl]-2-methoxy-6,7,8,9-tetrahydro-5H-benzocycloheptene In substantially the same manner as in Working Example 11, the above-titled compound was produced from 9-[2-(trifluoroacetylamino)ethylidene]-2-methoxy-6,7,8,9-tetrahydro-5H-benzocycloheptene (yield 97%, oil).

NMR($CDCl_3$) δ: 1.65–1.96(7H,m), 2.08–2.25(1H,m), 2.72–2.89(3H,m), 3.22–3.38(1H,m), 3.40–3.60(1H,m), 3.78 (3H,s), 6.18(1H,br s), 6.61–6.68(2H,m), 7.02(1H,d,J=8.0 Hz).

Working Example 19

(E)-6-Methoxy-1-[2-(trifluoroacetylamino)ethylidene]indan

In substantially the same manner as in Working Example 1, the above-titled compound was produced by (E)-1-(2-aminoethylidene)-6-methoxyindan and trifluoroacetic anhydride (yield 49%).

m.p.95–96° C. (recrystallized from isopropylether-hexane)

NMR($CDCl_3$) δ: 2.78–2.87(2H,m), 2.93–3.01(2H,m), 3.82(3H,s), 4.15(2H,t,J=6.4 Hz), 5.83–5.92(1H,m), 6.34 (1H,br s), 6.83(1H,dd,J=2.2 Hz,8.4 Hz), 6.94(1H,d,J=2.2 Hz), 7.17(1H,d,J=8.4 Hz).

Elemental Analysis for $C_{14}H_{14}F_3NO_2$: Calcd.: C, 58.95; H, 4.95; N, 4.91. Found: C, 58.73; H, 5.08; N, 5.02.

Working Example 20

(E)-1-[2-(Acetylamino)ethylidene]-6-methoxyindan

In substantially the same manner as in Working Example 1, the above-titled compound was produced from (E)-1-(2-aminoethylidene)-6-methoxyindan and acetyl chloride (yield 47%).

m.p.100–102° C. (recrystallized from ethyl acetate-isopropyl ether)

NMR($CDCl_3$) δ: 2.01(3H,s), 2.76–2.87(2H,m), 2.90–3.00 (2H,m), 3.81(3H,s), 4.03(2H,t,J=6.2 Hz), 5.53(1H,br s), 5.82–5.93(1H,m), 6.80(1H,dd,J=2.2 Hz,8.2 Hz), 6.93(1H,d, J=2.2 Hz), 7.15(1H,d,J=8.2 Hz).

Elemental Analysis for $C_{14}H_{17}NO_2$: Calcd.: C, 72.70; H, 7.41; N, 6.06. Found: C, 72.65; H, 7.31; N, 6.20.

Working Example 21

5,6-Dimethoxy-1-[2-(trifluoroacetylamino)ethyl]indan

In substantially the same manner as in Working Example 1, the above-titled compound was produced from 1-(2- aminoethyl)-5,6-dimethoxyindan hydrochloride and trifluoroacetic anhydride (yield 73%).

m.p.114–115° C. (recrystallized from isopropyl-ether hexane)

NMR($CDCl_3$) δ: 1.60–1.82(2H,m), 2.03–2.19(1H,m), 2.25–2.43(1H,m), 2.72–2.98(2H,m), 3.07–3.22(1H,m), 3.49 (2H,dd,J=7.2 Hz,13.6 Hz), 3.86(3H,s), 3.87(3H,s), 6.30(1H, br s), 6.73(1H,s), 6.77(1H,s).

Elemental Analysis for $C_{15}H_{18}F_3NO_3$: Calcd.: C, 56.78; H, 5.72; N, 4.41. Found: C, 56.73; H, 5.79; N, 4.55.

Working Example 22

1-[2-(Acetylamino)ethyl]-5,6-dimethoxyindan

In substantially the same manner as in Working Example 1, the above titled compound was produced from 1-(2-aminoethyl)-5,6-dimethoxyindan hydrochloride and acetyl chloride (yield 94%, oil).

NMR($CDCl_3$) δ: 1.48–1.80(2H,m), a.96–2.12(1H,m), 1.98(3H,s), 2.24–2.40(1H,m), 2.70–2.95(2H,m), 3.03–3.18 (1H,m), 3.37(2H,dd,J=7.4 Hz,13.6 Hz), 3.85(3H,s), 3.86 (3H,s), 5.60(1H,br s), 6.74(1H,s), 6.76(1H,s).

Working Example 23

1-[2-(Trifluoroacetylamino)ethyl]-7-methoxy-2,2-dimethyl-1,2,3,4-tetrahydronaphthalene To a solution of 1-(2-aminoethyl)-7-methoxy-1,2,3,4-tetrahydro-2,2-dimethylnaphthalene hydrochloride (1.5 g, 5.56 mmol) in pyridine (10 ml) was added gradually dropwise, under ice-cooling, trifluoroacetic anhydride (2.34 g, 11.1 mmol). The mixture was stirred for 4 hours at room temperature, which was poured into water, followed by subjecting the organic layer to extraction with chloroform. The extract solution was washed with brine and water, which was then dried over anhydrous magnesium sulfate, then the solvent was distilled off under reduced pressure. The residue was purified by means of a silica gel column chromatography (hexane:ethyl acetate=9:1) to give the above-titled compound (1.55 g, yield 85%, oil).

NMR($CDCl_3$) δ: 0.87(3H,s), 1.04(3H,s), 1.36–2.10(4H, m), 2.26(1H,dd,J=3.6 Hz,9.1 Hz), 2.70–2.80(2H,m), 3.20–3.61(2H,m), 3.78(3H,s), 6.13(1H,br s), 6.57(1H,d,J=2.6 Hz), 6.72(1H,dd,J=2.6 Hz,8.4 Hz), 7.02(1H,d,J=8.4 Hz).

Elemental Analysis for $C_{17}H_{22}F_3NO_2$: Calcd.: C, 61.99; H, 6.73; N, 4.25; F, 17.30. Found: C, 61.64; H, 6.74; N, 4.29; F, 17.58.

Working Example 24

7-Methoxy-1-[2-(methoxycarbonylamino)ethyl]-2,2-dimethyl-1,2,3,4-tetrahydronaphthalene By substantially the same procedure as in Working Example 23, the above-titled compound was produced from 1-(2-aminoethyl)-7-methoxy-2,2-dimethyl-1,2,3,4-tetrahydronaphthalene hydrochloride and methyl chlorocarbonate (yield 81%, oil)

NMR($CDCl_3$) δ: 0.86(3H,s), 1.02(3H,s), 1.35–1.55(2H, m), 1.65–2.05(2H,m), 2.23(1H,dd,J=3.0 Hz,8.8 Hz), 2.68–2.80(2H,m), 3.10–3.32(2H,m), 3.66(3H,s), 3.78(3H,s), 4.60(1H,br s), 6.59(1H,d,J=2.7 Hz), 6.70(1H,dd,J=2.7 Hz,8.3 Hz), 6.99(1H,d,J=8.3 Hz).

Elemental Analysis for $C_{17}H_{25}NO_3$: Calcd.: C, 70.07; H, 8.65; N, 4.81. Found: C, 69.87; H, 8.46; N, 4.93.

Working Example 25

7-Methoxy-2,2-dimethyl-1-[2-(3,3-dimethylureido)ethylidene]-1,2,3,4-tetrahydronaphthalene In substantially the same manner as in Working Example 1, a mixture of isomers of the above-titled compound was produced (yield 81%, oil) from 1-(2aminoethylidene)-7-methoxy-2,2-dimethyl-1,2,3,4-tetrahydronaphthalene and dimethylcarbamyl chloride. The product was subjected to a silica gel column chromatography and recrystallization to separate and purify the respective isomers.

E-isomer m.p.146–148° C. (recrystallized from petroleum ether/diethyl ether)

NMR($CDCl_3$) δ: 1.34(6H,s), 1.57(2H,t,J=6.0 Hz), 2.61 (2H,t,J=6.0 Hz), 2.92(6H,s), 3.80(3H,s), 4.26(2H,dd,J=5.3 Hz,7.1 Hz), 4.40(1H,br s), 5.82(1H,t,J=7.1 Hz), 6.72(1H,dd, J=2.6 Hz,8.4 Hz), 6.96–7.04(2H,m).

Elemental Analysis for $C_{13}H_{26}N_2O_2$: Calcd.: C, 71.49; H, 8.67; N, 9.26. Found: C, 71.32; H, 8.62; N, 9.36.

Z-isomer

Oil

NMR($CDCl_3$) δ: 1.09(6H,s), 1.66(2H,t,J=6.8 Hz), 2.75 (2H,t,J=6.8 Hz), 2.90(6H,s), 3.78(3H,s), 4.17(2H,t,J=6.0 Hz), 4.21(1H,br s), 5.50(1H,t,J=6.4 Hz), 6.69(1H,d,J=2.6 Hz), 6.76(1H,dd,J=2.6 Hz,8.2 Hz), 7.03(1H,d,J=8.2 Hz).

Elemental Analysis for $C_{18}H_{26}N_2O_2$: Calcd.: C, 71.49; H, 8.67; N, 9.26. Found: C, 71.51; H, 8.72; N, 9.18.

Working Example 26

(Z)-1-[2-(3-tert-Butylureido)ethylidene]-7-methoxy-2,2-dimethyl-1,2,3,4-tetrahydronaphthalene To a solution of 1-(2-aminoethylidene)-7-methoxy-2,2-dimethyl-1,2,3,4-tetrahydronaphthalene (1.5 g, 6.48 mmol) in THF (30 ml) was gradually added dropwise, under ice-cooling, Tert-butyl isocyanate (0.84 g, 8.43 mmol). The mixture was stirred for 2 hours at room temperature. The reaction mixture was then poured into water. The organic layer was subjected to ethyl acetate. The extract solution was washed with brine and water, which was dried over anhydrous magnesium sulfate, followed by distilling off the solvent under reduced pressure. The residue was purified by means of a silica gel column chromatography (hexane:ethyl acetate=8:2),-followed by recrystallization to give the above-titled compound (yield 780 mg, 36%), m.p.175–176° C. (recrystallized from ethyl acetate/diethyl ether).

NMR($d_6$-DMSO) δ: 1.05(6H,s), 1.21(9H,s), 1.60(2H,t,J=6.8 Hz), 2.70(2H,t,J=6.8 Hz), 3.73(3H,s), 3.81(2H,t,J=5.9 Hz), 5.42(1H,t,J=6.8 Hz), 5.60(1H,br s), 5.78(1H,t,J=6.8 Hz), 6.68(1H,d,J=2.6 Hz), 6.79(1H,dd,J=2.6 Hz,8.6 Hz), 7.06(1H,d,J=8.6 Hz).

Elemental Analysis for $C_{20}H_{30}N_2O_2$: Calcd.: C, 72.69; H, 9.15; N, 8.48. Found: C, 72.81; H, 9.07; N, 8.65.

Working Example 27

7-Methoxy-1-[2-(methoxyacetylamino)ethylidene]-2,2-dimethyl-1,2,3,4-tetrahydronaphthalene By substantially the same procedure as in Working Example 1, a mixture of isomers of the above-titled compound was produced from 1-(2-aminoethylidene)-7-methoxy-2,2-dimethyl-1,2,3,4-tetrahydronaphthalene and methoxyacetyl chloride (yield 75%, oil).

NMR($CDCl_3$) δ: 1.00–1.15(6H,m), 1.50–1.70(2H,m), 2.70–2.80(2H,m), 3.38–3.50(3H,m), 3.80–4.00(5H,m), 4.20–4.40(2H,m), 5.40–5.80(1H,m), 6.60–7.20(3H,m).

Elemental Analysis for $C_{18}H_{25}NO_3$: Calcd.: C, 71.26; H, 8.31; N, 4.62. Found: C, 71.33; H, 8.38; N, 4.51.

Working Example 28

7-Methoxy-1-[2-(4-methoxybenzoylamino)ethyl]-2,2-dimethyl-1,2,3,4-tetrahydronaphthalene By substantially the same procedures as in Working Example 1 and 11, The above-titled compound was produced from 1-(2-aminoethylidene)-7-methoxy-2,2-dimethyl-1,2,3,4-tetrahydronaphthalene and p-methoxybenzoyl chloride (yield 71%, oil).

NMR($CDCl_3$) δ: 0.86(3H,s), 1.04(3H,s), 1.32–2.16(4H, m), 2.30(1H,m), 2.68–2.80(2H,m), 3.25–3.72(2H,m), 3.76 (3H,s), 3.82(3H,s), 6.10(1H,br s), 6.65–6.74(2H,m), 6.87 (2H,d,J=8.8 Hz), 7.00(1H,d,J=8.4 Hz, 7.62(2H,d,J=8.8 Hz).

Elemental Analysis for $C_{23}H_{29}NO_3.0.5H_2O$: Calcd.: C, 73.37; H, 8.03; N, 3.72. Found: C, 73.30; H, 7.78; N, 3.55.

Working Example 29

(E)-1-[2-(Trifluoroacetylamino)ethylidene]-5,7-dimethyl-1,2,3,4-tetrahydronaphthalene By substantially the same procedure as in Working Example 1, the above-titled compound was produced from 1-(2-aminoethylidene)-5,7-dimethyl-1,2,3,4-tetrahydronaphthalene and trifluoroacetic anhydride (yield 89%), m.p.143–146° C. (recrystallized from ethyl acetate).

NMR($CDCl_3$) δ: 1.89(2H,m), 2.21(3H,s), 2.47(3H,s), 2.50(2H,t,J=6.0 Hz), 2.66(2H,t,J=6.2 Hz), 4.17(2H,t,J=6.4 Hz), 5.92(1H,t,J=7.3 Hz), 6.35(1H,br s), 6.93(1H,s), 7.23 (1H,s).

Elemental Analysis for $C_{16}H_{18}F_3NO$: Calcd.: C, 64.64; H, 6.10; N, 4.71; F, 19.17. Found: C, 64.47; H, 6.17; N, 4.81; F, 19.32.

Working Example 30

(E)-5,7-Dimethyl-1-[2-(3,3-dimethylureido) ethylidene]-1,2,3,4-tetrahydronaphthalene By substantially the same procedure as in Working Example 1, a mixture of isomers of the above-titled compound was produced from 1-(2-aminoethylidene)-5,7-dimethyl-1,2,3,4-tetrahydronaphthalene and dimethylcarbamyl chloride (yield 89%). The mixture was subjected to a silica gel column chromatography and recrystallization to separate the above-titled compound in a pure state (yield 25%), m.p.141–143° C. (recrystallized from ethyl acetate).

NMR($CDCl_3$) δ: 1.86(2H,m), 2.20(3H,s), 2.28(3H,s), 2.50(2H,t,J=5.9 Hz), 2.64(2H,t,J=6.2 Hz), 2.92(6H,s), 4.04 (2H,t,J=6.2 Hz), 4.37(1H,br s), 5.98(1H,t,J=7.0 Hz), 6.89 (1H,s), 7.26(1H,s).

Elemental Analysis for $C_{17}H_{24}N_2O$: Calcd.: C, 74.96; H, 8.88; N, 10.28. Found: C, 75.16; H, 8.92; N, 10.32.

Working Example 31

5,7-Dimethyl-1-[2-(3,3-dimethylureido)ethyl]-1,2,3,4-tetrahydronaphthalene

By substantially the same procedure as in Working Example 11, the above-titled compound was produced from 5,7-dimethyl-1-[2-(3,3-dimethylureido)ethylidene]-1,2,3,4-tetrahydronaphthalene (yield 80%), m.p.121–123° C. (recrystallized from ethyl acetate/hexane).

NMR($CDCl_3$) δ: 1.65–2.00(6H,m), 2.17(3H,s), 2.26(3H, s), 2.50–2.63(2H,m), 2.75–2.87(1H,m), 2.86(6H,s), 3.28–3.44(2H,m), 4.30(1H,br s), 6.82(1H,s), 6.84(1H,s).

Elemental Analysis for $C_{17}H_{26}N_2O$: Calcd.: C, 74.41; H, 9.55; N, 10.21. Found: C, 74.45; H, 9.56; N, 10.13.

Working Example 32

1-[2-(Trifluoroacetylamino)ethyl]-5,7-dimethyl-1,2,3,4-tetrahydronaphthalene

By substantially the same procedure as in Working Example 11, the above-titled compound was produced from 1-[2-(trifluoroacetylamino)ethylidene]-5,7-dimethyl-1,2,3,4-tetrahydronaphthalene (yield 83%), m.p.103–105° C. (recrystallized from hexane).

NMR($CDCl_3$) δ: 1.60–2.00(6H,m), 2.18(3H,s), 2.26(3H, s), 2.50–2.63(2H,m), 2.75–2.90(1H,m), 3.40–3.57(2H,m), 6.23(1H,br s), 6.80(1H,s), 6.84(1H,s).

Elemental Analysis for $C_{16}H_{20}F_3NO$: Calcd.: C, 64.20; H, 6.73; N, 4.68; F, 19.04. Found: C, 64.22; H, 6.73; N, 4.67; F, 19.18.

Working Example 33

(E)-1-[2-(Trifluoroacetylamino)ethylidene]-7-methoxy-1,2,3,4-tetrahydronaphthalene By substantially the same procedure as in Working Example 1, a mixture of isomers of the above-titled compound was produced from 1-(2-aminoethylidene)-7-methoxy-1,2,3,4-tetrahydronaphthalene and trifluoroacetic anhydride (yield 85%). The mixture was subjected to a silica gel column chromatography and recrystallization to separate the above-titled compound in a pure state (yield 37%), m.p.98–100° C. (recrystallized from diethyl ether).

NMR($CDCl_3$) δ: 1.84(2H,m), 2.53(2H,t,J=5.5 Hz), 2.73 (2H,t,J=6.2 Hz), 3.81(3H,s), 4.18(2H,t,J=6.2 Hz), 5.93(1H, t,J=7.1 Hz), 6.40(1H,br s), 6.78(1H,dd,J=2.6 Hz,8.4 Hz), 7.00–7.10(2H,m).

Elemental Analysis for $C_{15}H_{16}F_3NO_2$: Calcd.: C, 60.20; H, 5.39; N, 4.68. Found: C, 60.23; H, 5.39; N, 4.76.

Working Example 34

1-[2-(Trifluoroacetylamino)ethyl]-7-methoxy-1,2,3,4-tetrahydronaphthalene

By substantially the same procedure as in Working Example 11, the above-titled compound was produced from 1-[2-(trifluoroacetylamino)ethylidene]-7-methoxy-1,2,3,4-tetrahydronaphthalene (yield 82%, oil).

NMR($CDCl_3$) δ: 1.60–2.10(6H,m), 2.69(2H,t,J=5.4 Hz), 2.84(1H,m), 3.47(2H,q,J=7.0 Hz), 3.78(3H,s), 6.30(1H,m), 6.65–6.76(2H,m), 6.99(1H,d,J=7.7 Hz).

Elemental Analysis for $C_{15}H_{18}F_3NO_2$: Calcd.: C, 59.79; H, 6.02; N, 4.65. Found: C, 60.09; H, 6.06; N, 4.40.

Working Example 35

1-[2-(Acetylamino)ethyl]-7-hydroxy-1,2,3,4-tetrahydronaphthalene

To a solution of 1-[2-(acetylamino)ethyl]-7-methoxy-1,2,3,4-tetrahydronaphthalene (3.14 g, 12.7 mmol) in dichloromethane (70 ml) was added dropwise, under ice-cooling, boron tribromide (6.4 g, 25.4 mmol). The reaction mixture was stirred for 50 minutes at room temperature, which was poured into water. The organic layer was subjected to extraction with chloroform. The extract solution was washed with brine and water, which was dried over anhydrous magnesium sulfate, followed by distilling off the solvent under reduced pressure. The residue was purified by means of a silica gel column chromatography (chloroform:methanol=9:1) to give the above-titled compound (1.54 g, yield 52%), m.p.153–155° C. (recrystallized from ethyl acetate).

NMR($CDCl_3$) δ: 1.55–2.10(6H,m), 1.98(3H,s), 2.66(2H, t,J=5.8 Hz), 2.68–2.82(1H,m), 3.28–3.42(2H,m), 5.72(1H,br s), 6.61–6.70(2H,m), 6.85(1H,br s), 6.92(1H,d,J=7.7 Hz).

Elemental Analysis for $C_{14}H_{19}NO_2$: Calcd.: C, 72.07; H, 8.21; N, 6.00. Found: C, 72.01; H, 8.34; N, 6.01.

Working Example 36

(E)-1-[2-(Trifluoroacetylamino)ethylidene]-6,7-dimethoxy-1,2,3,4-tetrahydronaphthalene By substantially the same procedure as in Working Example 1, a mixture of isomers of the above-titled compound was produced from 1-(2-aminoethylidene)-6,7-dimethoxy-1,2,3,4-tetrahydronaphthalene and trifluoroacetic anhydride (yield 75%). The mixture was subjected to a silica gel column chromatography and recrystallization to separate the above-titled compound in a pure state (yield 29%), m.p.117–1190° C. (recrystallized from ethyl acetate/hexane).

NMR($CDCl_3$) δ: 1.85(2H,m), 2.53(2H,t,J=6.4 Hz), 2.74 (2H,t,J=6.2 Hz), 3.88(3H,s), 3.90(3H,s), 4.18(2H,t,J=6.2 Hz), 5.83(1H,t,J=7.1 Hz), 6.36(1H,br s), 6.59(1H,s), 7.03 (1H,s).

Elemental Analysis for $C_{16}H_{18}F_3NO_3$: Calcd.: C, 58.36; H, 5.51; N, 4.25. Found: C, 58.16; H, 5.60; N, 4.22.

Working Example 37

(E)-1-[2-(Acetylamino)ethylidene]-6,7-dimethoxy-1,2,3,4-tetrahydronaphthalene

By substantially the same procedure as in Working Example 1, a mixture of isomers of the above-titled compound was produced from 1-(2-aminoethylidene)-6,7-dimethoxy-1,2,3,4-tetrahydronaphthalene and acetyl chloride (yield 78%). The mixture was subjected to a silica gel chromatography and recrystallization to separate the above-titled compound in a pure state (yield 39%), m.p.131–133° C. (recrystallized from ethyl acetate/hexane).

NMR($CDCl_3$) δ: 1.83(2H,m), 2.02(3H,s), 2.51(2H,t,J=5.8 Hz), 2.73(2H,t,J=6.2 Hz), 3.87(3H,s), 3.89(3H,s), 4.07(2H, t,J=6.1 Hz), 5.58(1H,br s), 5.84(1H,t,J=7.1 Hz), 6.58(1H,s), 7.05(1H,s).

Elemental Analysis for $C_{16}H_{21}NO_3$: Calcd.: C, 69.79; H, 7.69; N, 5.09. Found: C, 69.63; H, 7.46; N, 4.99.

Working Example 38

1-[2-(Acetylamino)ethyl]-6,7-dimethoxy-1,2,3,4-tetrahydronaphthalene

By substantially the same procedure as in Working Example 11, the above-titled compound was produced from 1-[2-(acetylamino)ethylidene]-6,7-dimethoxy-1,2,3,4-tetrahydronaphthalene (yield 78%, oil).

NMR($CDCl_3$) δ: 1.60–1.93(6H,m), 1.98(3H,s), 2.68(2H, t,J=4.9 Hz), 2.76(1H,m), 3.22–3.49(2H,m), 3.84(3H,s), 3.86 (3H,s), 5.57(1H,br s), 6.56(1H,s), 6.66(1H,s).

Elemental Analysis Calcd for $C_{16}H_{23}NO_3$: Calcd.: C, 69.29; H, 8.36; N, 5.05. Found: C, 69.86; H, 8.33; N, 4.89.

Working Example 39

1-[2-(Trifluoroacetylamino)ethyl]-6,7-dimethoxy-1,2,3,4-tetrahydronaphthalene

By substantially the same procedure as in Working Example 11, the above-titled compound was produced from 1-[2-(trifluoroacetylamino)ethylidene]-6,7-dimethoxy-1,2,3,4-tetrahydronaphthalene (yield 53%), m.p.76–78° C. (recrystallized from ethyl acetate/hexane).

NMR($CDCl_3$) δ: 1.60–2.10(6H,m), 2.69(2H,t,J=5.5 Hz), 2.75–2.87(1H,m), 3.40–3.57(2H,m), 3.84(3H,s), 3.86(3H,s), 6.33(1H,br s), 6.57(1H,s), 6.63(1H,s).

Elemental Analysis for $C_{16}H_{20}F_3NO_3$: Calcd.: C, 58.00; H, 6.08; N, 4.23. Found: C, 57.94; H, 5.94; N, 4.37.

Working Example 40

1'-[2-(Trifluoroacetylamino)ethyl]-1,3,3',4'-tetrahydro-7'-methoxyspiro[2H-indene-2,2'(1'H)naphthalene]

By substantially the same procedure as in Reference Example 6, 7, Working Example 11, Reference Example 3-B and Working Example 1, the above-titled compound was produced from 1,3,3',4'-tetrahydrospiro[2H-indene-2,2'(1'H)-naphthalene]-1'-one (yield 13%), m.p.149–152° C. (recrystallized from ethyl acetate/hexane).

NMR($CDCl_3$) δ: 1.60–2.12(4H,m), 2.44–3.13(7H,m), 3.20–3.72(2H,m), 3.80(3H,s), 6.10(1H,br s), 6.58(1H,d,J=2.6 Hz), 6.77(1H,dd,J=2.6 Hz,8.2 Hz), 7.10–7.22(5H,m).

Elemental Analysis for $C_{23}H_{24}F_3NO_2$: Calcd.: C, 68.47; H, 6.00; N, 3.47. Found: C, 68.69; H, 5.98; N, 3.55.

Working Example 41

1'-[2-(Acetylamino)ethyl]-1,3,3',4'-tetrahydro-7'-methoxyspiro[2H-indene-2,2'(1'H)-naphthalene]

By substantially the same procedure as in Reference Example 6, 7, Working Example 11, Reference Example 3-B and Working Example 1, the above-titled compound was produced from 1,3,3',4'-tetrahydrospiro[2H-indene-2,2'(1'H)-naphthalen]-1'-one (yield 16%), m.p.139–141° C. (recrystallized from ethyl acetate/hexane).

NMR($CDCl_3$) δ: 1.41–2.06(4H,m), 1.92(3H,s), 2.45–3.10 (7H,m), 3.10–3.60(2H,m), 3.80(3H,s), 5.38(1H,br s), 6.63 (1H,d,J=2.6 Hz), 6.74(1H,dd,J=2.6 Hz,8.2 Hz), 7.00–7.21 (5H,m).

Elemental Analysis for $C_{23}H_{27}NO_2$: Calcd.: C, 79.05; H, 7.79; N, 4.01. Found: C, 79.23; H, 7.82; N, 4.00.

Working Example 42

(E)-9-[2-(Acetylamino)ethylidene]-2isopropoxy-6,7,8,9-tetrahydro-5H-benzocycloheptene By substantially the same procedure as in Working Example 1, a mixture of isomers of the above-titled compound was produced from 9-(2-aminoethylidene)-2isopropoxy-6,7,8,9-tetrahydro-5H-benzocycloheptene and acetyl chloride (yield 80%). The mixture was subjected to a silica gel chromatography to separate the above-titled compound in a pure state (yield 33%, oil).

NMR($CDCl_3$) δ: 1.32(6H,d,J=6.0 Hz), 1.71(4H,br s), 2.01(3H,s), 2.40(2H,br s), 2.65(2H,t,J=5.4 Hz), 4.02(2H,t, J=5.5 Hz), 4.52(1H,m), 5.43(1H,t,J=6.9 Hz), 5.68(1H,br s), 6.60–6.72(2H,m), 6.97(1H,d,J=8.4 Hz).

Elemental Analysis for $C_{18}H_{25}NO_2$: Calcd.: C, 75.22; H, 8.77; N, 4.87. Found: C, 75.41; H, 8.58; N, 4.81.

Working Example 43

9-[2-(Acetylamino)ethyl]-2-isopropoxy-6,7,8,9-tetrahydro-5H-benzocycloheptene

By substantially the same procedure as in Working Example 11, the above-titled compound was produced from 9-[2-(acetylamino)ethylidene]-2-isopropoxy-6,7,8,9-tetrahydro-5H-benzocycloheptene (yield 92%, oil).

NMR($CDCl_3$) δ: 1.32(6H,d,J=6.2 Hz), 1.50–2.20(8H,m), 1.91(3H,s), 2.70–2.95(3H,m), 3.07–3.50(2H,m), 4.51(1H, m), 5.45(1H,br s), 6.60(1H,dd,J=2.6 Hz,8.1 Hz), 6.66(1H, d,J=2.6 Hz), 6.98(1H,d,J=8.1 Hz).

Elemental Analysis for $C_{18}H_{27}NO_2$: Calcd.: C, 74.70; H, 9.40; N, 4.84. Found: C, 74.58; H, 9.37; N, 4.76.

Working Example 44

(E)-9-[2-(Trifluoroacetylamino)ethylidene]-2isopropoxy-6,7,8,9-tetrahydro-5H-benzocycloheptene By substantially the same procedure as in Working Example 1, a mixture of isomers of the above-titled compound from 9-(2-aminoethylidene)-2-isopropoxy-6,7,8,9-tetrahydro-5H-benzocycloheptene and trifluoroacetic anhydride (yield 89%). The mixture was subjected to a silica gel chromatography to separate the above-titled compound in a pure state (yield 38%, oil).

NMR($CDCl_3$) δ: 1.33(6H,d,J=6.2 Hz), 1.73(4H,br s), 2.42(2H,br s), 2.65(2H,br s), 4.14(2H,t,J=6.4 Hz), 4.52(1H, m), 5.44(1H,t,J=7.0 Hz), 6.40(1H,br s), 6.63–6.74(2H,m), 6.98(1H,d,J=8.4 Hz).

Elemental Analysis for $C_{18}H_{22}F_3NO_2$: Calcd.: C, 63.33; H, 6.50; N, 4.10. Found : C, 63.51; H, 6.62; N, 4.26.

Working Example 45

9-[2-(Trifluoroacetylamino)ethyl]-2-isopropoxy-6,7,8,9-tetrahydro-5H-benzocycloheptene By substantially the same procedure as in Working Example 11, the above-titled compound was produced from 9-[2-(trifluoroacetylamino)ethylidene]-2-isopropoxy-6,7,8,9-tetrahydro-5H-benzocycloheptene (yield 91%, oil).

NMR($CDCl_3$) δ: 1.32(6H,d,J=6.2 Hz), 1.45–2.25(8H,m), 2.70–2.90(3H,m), 3.17–3.60(2H,m), 4.51(1H,m), 6.20(1H, br s), 6.58–6.68(2H,m), 6.99(1H,d,J=8.4 Hz).

Elemental Analysis for $C_{18}H_{24}F_3NO_2$: Calcd.: C, 62.96; H, 7.04; N, 4.08. Found: C, 62.81; H, 7.00; N, 3.97.

Working Example 46

6-Methoxy-2,2-dimethyl-1-[2-(trifluoroacetylamino)ethyl]indan

By substantially the same procedure as in Working Example 1, the above-titled compound was produced from 1-(2-aminoethyl)-6-methoxy-2,2-dimethylindan hydrochloride and trifluoroacetic anhydride (yield 93%, oil).

NMR($CDCl_3$) δ: 1.01(3H,s), 1.12(3H,s), 1.61–1.97(2H, m), 2.51–2.71(3H,m), 3.53(2H,dd,J=7.2 Hz, 13.8 Hz), 3.80 (3H,s), 6.32(1H,br s), 6.70(1H,dd,J=2.4 Hz, 8.0 Hz), 6.76 (1H,d,J=2.4 Hz), 7.07(1H,d,J=8.0 Hz).

Working Example 47

(E)-6-Methoxy-2,2-dimethyl-1-[2-(trifluoroacetylamino)ethylidene]indan

By substantially the same procedure as in Working Example 1, the above-titled compound was produced from (E)-1-(2-aminoethylidene)-6-methoxy-2,2-dimethylindan and trifluoroacetic anhydride (yield 96%, oil).

NMR($CDCl_3$) δ: 1.37(6H,s), 2.83(2H,s), 3.81(3H,s), 4.32 (2H,dd,J=6.0 Hz, 7.4 Hz), 5.82(1H,t,J=7.4 Hz), 6.36(1H,br s), 6.83(1H,dd,J=2.4 Hz, 8.0 Hz), 6.89(1H,d,J=2.4 Hz), 7.10(1H,d,J=8.0 Hz).

Working Example 48

(Z)-6-Methoxy-2,2-dimethyl-1-[2-(trifluoroacetylamino)ethylidene]indan

By substantially the same procedure as in Working Example 1, the above-titled compound was produced from (Z)-1-(2-aminoethylidene)-6-methoxy-2,2-dimethylindan and trifluoroacetic anhydride (yield 43%), m.p.107–108° C. (recrystallized from isopropyl ether/hexane).

NMR($CDCl_3$) δ: 1.20(6H,s), 2.75(2H,s), 3.81(3H,s), 4.41 (2H,t,J=6.4 Hz), 5.35(1H,t,J=6.4 Hz), 6.39(1H,br s), 6.85 (1H,dd,J=2.2 Hz, 8.4 Hz), 6.95(1H,d,J=2.2 Hz), 7.17(1H,d, J=8.4 Hz).

Elemental Analysis for $C_{16}H_{18}F_3NO_2$: Calcd.: C, 61.34; H, 5.79; N, 4.47. Found: C, 61.25; H, 5.92; N, 4.52.

Working Example 49

6-Methoxy-1-[3-(trifluoroacetylamino)propyl]indan

By substantially the same procedure as in Working Example 1, the above-titled compound was produced from 1-(3-aminopropyl)-6-methoxyindan and trifluoroacetic anhydride (yield 97%, oil).

NMR($CDCl_3$) δ: 1.40–1.94(5H,m), 2.01–2.38(1H,m), 2.69–2.90(2H,m), 3.02–3.18(1H,m), 3.42(2H,q,J=6.6 Hz), 3.80(3H,s), 6.30(1H,br s), 6.69–6.75(2H,m), 7.08–7.15(1H, m).

Working Example 50

1-[3-(Acetylamino)propyl]-6-methoxyindan

By substantially the same procedure as in Working Example 1, the above-titled compound was produced from 1-(3-aminopropyl)-6-methoxyindan and acetyl chloride (yield 69%), m.p.74–75° C. (recrystallized from isopropyl ether).

NMR($CDCl_3$) δ: 1.35–1.92(5H,m), 1.98(3H,s), 2.20–2.38 (1H,m), 2.71–2.90(2H,m), 3.02–3.16(1H,m), 3.29(2H,dd,J=7.0 Hz, 13.0 Hz), 3.80(3H,s), 5.49(1H,br s), 6.67–6.74(2H, m), 7.08–7.14(1H,m).

Elemental Analysis for $C_{15}H_{21}NO_2$: Calcd.: C, 72.84; H, 8.56; N, 5.66. Found: C, 72.81; H, 8.49; N, 5.97

Working Example 51

6-Methoxy-1-[2-(propionylamino)ethyl]indan

By substantially the same procedure as in Working Example 1, the above-titled compound was produced from 1-(2-aminoethyl)-6-methoxyindan and propionyl chloride (yield 60%), m.p.76–77° C. (recrystallized from isopropyl ether/hexane).

NMR($CDCl_3$) δ: 1.15(3H,t,J=7.8 Hz), 1.50–1.80(2H,m), 1.97–2.40(2H,m), 2.19(2H,q,J=7.8 Hz), 2.68–2.95(2H,m), 3.04–3.18(1H,m), 3.33–3.45(2H,m), 3.79(3H,s), 5.46(1H,br s), 6.68–6.76(2H,m), 7.11(1H,d,J=8.0 Hz).

Elemental Analysis for $C_{15}H_{21}NO_2$: Calcd.: C, 72.84; H, 8.56; N, 5.66. Found: C, 72.82; H, 8.42; N, 5.62

Working Example 52

(E)-5,6,7-Trimethoxy-1-[2-(trifluoroacetylamino)ethylidene]indan

By substantially the same procedure as in Working Example 1, the above-titled compound was produced from (E)-1-(2-aminoethylidene)-5,6,7-trimethoxyindan and trifluoroacetic anhydride (yield 83%), m.p.97–98° C. (recrystallized from isopropyl ether).

NMR($CDCl_3$) δ: 2.75–2.83(2H,m), 2.90–3.02(2H,m), 3.84(3H,s), 3.86(3H,s), 3.93(3H,s), 4.12(2H,t,J=6.4 Hz), 6.20–6.40(2H,m), 6.57(1H,s).

Elemental Analysis for $C_{16}H_{18}F_3NO_4$: Calcd.: C, 55.65; H, 5.25; N, 4.06. Found: C, 55.64; H, 5.23; N, 4.10

Working Example 53

5,6,7-Trimethoxy-1-[2-(trifluoroacetylamino)ethyl]indan

By substantially the same procedure as in Working Example 11, the above-titled compound was produced from (E)-5,6,7-trimethoxy-1-[2-(trifluoroacetylamino)ethylidene]indan as an oily product. The yield was 97%.

NMR($CDCl_3$) δ: 1.62–1.95(2H,m), 2.18–2.38(1H,m), 2.69–2.84(1H,m), 2.90–3.12(2H,m), 3.21–3.34(1H,m), 3.55–3.77(2H,m), 3.84(3H,s), 3.85(3H,s), 3.93(3H,s), 6.60 (2H,br s).

Working Example 54

(E)-5-Bromo-6-methoxy-7-methyl-1-[2-(trifluoroacetylamino)ethylidene]indan

By substantially the same procedure as in Working Example 1, the above-titled compound was produced from (E)-1-(2-aminoethylidene)-5-bromo-6-methoxy-7-methylindan and trifluoroacetic anhydride (yield 89%), m.p.138–139° C. (recrystallized from isopropyl ether).

NMR($CDCl_3$) δ: 2.44(3H,s), 2.76–2.86(2H,m), 2.88–2.99 (2H,m), 3.76(3H,s), 4.15(2H,t,J=6.4 Hz), 5.87–5.96(1H,m), 6.41(1H,br s), 7.32(1H,s).

Elemental Analysis for $C_{15}H_{15}BrF_3NO_2$: Calcd.: C, 47.64; H, 4.00; N, 3.70. Found: C, 47.59; H, 3.96; N, 3.60.

Working Example 55

6-Methoxy-7-methyl-1-[2-(trifluoroacetylamino)ethyl]indan

By substantially the same procedure as in Working Example 11, the above-titled compound was produced from (E)-5-bromo-6-methoxy-7-methyl-1-[2-(trifluoroacetylamino)ethylidene]indan (yield 68%), m.p.126–127° C. (recrystallized from ethyl acetate/hexane).

NMR($CDCl_3$) δ: 1.62–2.32(4H,m), 2.16(3H,s), 2.74–3.05 (2H,m), 3.22–3.58(3H,m), 3.81(3H,s), 6.17(1H,br s), 6.69 (1H,d,J=8.2 Hz), 7.02(1H,d,J=8.2 Hz).

Elemental Analysis for $C_{15}H_{18}F_3NO_2$: Calcd.: C, 59.79; H, 6.02; N, 4.65. Found: C, 59.96; H, 5.95; N, 4.62.

Working Example 56

1-[2-(Crotonoylamino)ethyl]-6-methoxyindan

By substantially the same procedure as in Working Example 1, the above-titled compound was produced from 1-(2-aminoethyl)-6-methoxyindan and crotonoyl chloride (yield 37%), m.p.107–108° C. (recrystallized from ethyl acetate/isopropyl ether).

NMR($CDCl_3$) δ: 1.52–1.78(2H,m), 1.85(3H,dd,J=1.6 Hz, 6.8 Hz), 2.01–2.18(1H,m), 2.25–2.41(1H,m), 2.69–2.95(2H, m), 3.05–3.20(1H,m), 3.40–3.51(2H,m), 3.79(3H,s), 5.47 (1H,br s), 5.77(1H,dd,J=1.6 Hz, 15.2 Hz), 6.70–6.93(3H,m), 7.11(1H,d,J=8.2 Hz).

Elemental Analysis for $C_{16}H_{21}NO_2$: Calcd.: C, 74.10; H, 8.16; N, 5.40. Found: C, 73.80; H, 8.22; N, 5.28.

Working Example 57

6-Methoxy-1-[2-(methoxycarbonylamino)ethyl]indan

By substantially the same procedure as in Working Example 1, the above-titled compound was produced from 1-(2-aminoethyl)-6-methoxyindan and methyl chloroformate (yield 67%) as an oily product.

NMR($CDCl_3$) δ: 1.50–1.80(2H,m), 1.97–2.14(1H,m), 2.23– 2.40(1H,m), 2.69–2.96(2H,m), 3.02–3.20(1H,m), 3.25–3.38(2H,m), 3.68(3H,s), 3.80(3H,s), 4.72(1H,br s), 6.72(1H,dd,J=2.6 Hz, 8.4 Hz), 6.74(1H,br s), 7.11(1H,d,J= 8.4 Hz).

Working Example 58

(E)-7-Bromo-6-methoxy-5-methyl-1-[2-(trifluoroacetylamino)ethylidene]indan

By substantially the same procedure as in Working Example 1, the above-titled compound was produced from (E)-1-(2-aminoethylidene)-7-bromo-6-methoxy-5-methylindan and trifluoroacetic anhydride (yield 88%), m.p.117–118° C. (recrystallized from ethyl acetate/isopropyl ether).

NMR($CDCl_3$) δ: 2.33(3H,s), 2.78–2.88(2H,m), 2.90–2.98 (2H,m), 3.79(3H,s), 4.17(2H,t,J=6.2 Hz), 6.42(1H,br s), 6.81–6.91(1H,m), 7.03(1H,s).

Elemental Analysis for $C_{15}H_{15}BrF_3NO_2$: Calcd.: C, 47.64; H, 4.00; N, 3.70. Found: C, 47.85; H, 3.90; N, 3.75

Working Example 59

6-Methoxy-5-methyl-1-[2-(trifluoroacetylamino)ethyl]indan

By substantially the same procedure as in Working Example 11, the above-titled compound was produced from (E)-7-bromo-6-methoxy-5-methyl-1-[2-(trifluoroacetylamino)ethylidene]indan (yield 49%), m.p.105–106° C. (recrystallized from ethyl acetate/hexane).

NMR($CDCl_3$) δ: 1.61–1.80(2H,m), 2.04–2.41(2H,m), 2.19(3H,s), 2.70–2.96(2H,m), 3.08–3.21(1H,m), 3.50(2H,q, J=7.0 Hz), 3.82(3H,s), 6.30(1H,br s), 6.68(1H,s), 7.00(1H, s).

Elemental Analysis for $C_{15}H_{18}F_3NO_2$: Calcd.: C, 59.79; H, 6.02; N, 4.65. Found: C, 59.44; H, 6.04; N, 4.71

Working Example 60

1-[2-(Acetylamino)ethyl]-6-hydroxyindan

To a solution of 1-[2-(acetylamino)ethyl]-6-methoxyindan (6.40 g, 27.4 mmol) in dichloromethane (150 ml) was added dropwise, under ice-cooling, boron tribromide (5.19 ml, 54.8 mmol). The mixture was then stirred for one hour. The reaction mixture was poured into water. The mixture was stirred for 8 hours at room temperature, which was subjected to extraction with chloroform. The extract solution was washed with brine, which was dried over anhydrous magnesium sulfate, followed by distilling off the solvent under reduced pressure. The residue was recrystallized from ethyl acetate/isopropyl ether to give 4.70 g (yield 78%) of the above-titled compound, m.p.107–108° C.

NMR($CDCl_3$) δ: 1.50–1.75(2H,m), 1.90–2.08(1H,m), 1.98(3H,s), 2.20–2.35(1H,m), 2.66–2.87(2H,m), 2.98–3.13 (1H,m), 3.35(2H,dd,J=7.0 Hz, 13.2 Hz), 5.80(1H,br s), 6.64–6.74(2H,m), 7.04(1H,d,J=7.8 Hz).

Elemental Analysis for $C_{13}H_{17}NO_2$: Calcd.: C, 71.21; H, 7.81; N, 6.39. Found: C, 70.93; H, 7.90; N, 6.21.

Working Example 61

1-Benzyloxycarbonyl-N-[2-(6-methoxyindan-1-yl)ethyl]-4-piperidinecarboxamide To a solution of 1-(2-aminoethyl)-6-methoxyindan (1.00 g, 5.23 mmol), 1-benzyloxycarbonyl-4-piperidinecarboxylic acid (1.38 g, 5.23 mmol) and 1-hydroxy-1H-benzotriazole (0.78 g, 5.75 mmol) in DMF (20 ml) was added 1-ethyl-3-(3-dimethylaminopropyl)carbodiimide hydrochloride (WSC; 1.10 g, 5.75 mmol). The mixture was stirred for 6 hours at room temperature. To the reaction mixture was added water, and the mixture was subjected to extraction with ethyl acetate. The extract solution was washed with brine, which was dried over anhydrous magnesium sulfate, followed by distilling off the solvent under reduced pressure. The residue was purified by means of a silica gel column chromatography (chloroform/methanol, 95:5) to give 2.10 g (yield 92%) of the above-titled compound, m.p.132–133° C. (recrystallized from ethyl acetate/isopropyl ether).

NMR($CDCl_3$) δ: 1.50–1.88(6H,m), 1.95–2.40(3H,m), 2.70–2.95(4H,m), 3.02–3.20(1H,m), 3.33–3.45(2H,m), 3.78 (3H,s), 4.13–4.26(2H,m), 5.12(2H,s), 5.42(1H,br s), 6.67–6.74(2H,m), 7.11(1H,d,J=7.6 Hz), 7.35(5H,s).

Elemental Analysis for $C_{26}H_{32}N_2O_4$: Calcd.: C, 71.53; H, 7.39; N, 6.42. Found: C, 72.00; H, 7.53; N, 7.09.

Working Example 62

6-Ethoxy-1-[2-(trifluoroacetylamino)ethyl]indan

By substantially the same procedure as in Working Example 1, the above-titled compound was produced from 1-(2-aminoethyl)-6-ethoxyindan and trifluoroacetic anhydride (yield 36%), m.p.85–86° C. (recrystallized from isopropyl ether/hexane).

NMR($CDCl_3$) δ: 1.41(3H,t,J=7.0 Hz), 1.62–1.81(2H,m), 2.04–2.20(1H,m), 2.28–2.41(1H,m), 2.71–2.98(2H,m), 3.08–3.21(1H,m), 3.50(2H,q,J=7.0 Hz), 4.02(2H,q,J=7.0 Hz), 6.32(1H,br s), 6.71–6.76(2H,m), 7.12(1H,d,J=8.4 Hz).

Elemental Analysis for $C_{15}H_{18}F_3NO_2$: Calcd.: C, 59.79; H, 6.02; N, 4.65. Found: C, 59.31; H, 6.00; N, 4.85

Working Example 63

6-(2-Phenylethoxy)-1-[2-trifluoroacetylamino)ethyl] indan

By substantially the same procedure as in Working Example 1, the above-titled compound was produced from 1-(2-aminoethyl)-6-(2-phenylethoxy)indan and trifluoroacetic anhydride (yield 63%), m.p.114–115° C. (recrystallized from isopropyl ether/hexane).

NMR($CDCl_3$) δ: 1.60–1.80(2H,m), 2.02–2.18(1H,m), 2.22–2.40(1H,m), 2.70–2.95(2H,m), 3.04–3.19(3H,m), 3.48 (2H,q,J=7.2 Hz), 4.15(2H,t,J=7.0 Hz), 6.23(1H,br s), 6.69–6.74(2H,m), 7.10(1H,d,J=8.6 Hz), 7.20–7.38(5H,m).

Elemental Analysis for $C_{21}H_{22}F_3NO_2$: Calcd.: C, 66.83; H, 5.88; N, 3.71. Found: C, 66.86; H, 5.77; N, 4.04.

Working Example 64

1-[2-(Acetylamino)ethyl]-1,2,3,4-tetrahydro-7-(N-methylamino)naphthalene

To a solution of 1-(2-aminoethyl)-7-formylamino1,2,3,4-tetrahydronaphthalene (1.80 g, 8.25 mmol) in THF (20 ml) was added added, under ice-cooling, lithium aluminum hydride (0.63 g, 16.5 mmol). The mixture was heated for 4 hours under reflux under argon atmosphere. The reaction mixture was cooled with ice, to which was added water (0.9 ml), followed by further addition of ethyl acetate, anhydrous magnesium sulfate and celite, successively. The mixture was subjected to filtration, and the filtrate was concentrated under reduced pressure. The concentrate was dissolved in DMF (20 ml). To the solution was added 4-nitrophenyl acetate (1.33 g, 7.34 mmol), and the mixture was stirred for 20 minutes at room temperature. To the reaction mixture was added water, which was subjected to extraction with ethyl acetate. The extract solution was washed with brine, which was dried over anhydrous magnesium sulfate, followed by distilling off the solvent under reduced pressure. The residue was purified by means of a silica gel column chromatography (methanol/ethyl acetate, 97:3–96:5) to give 1.10 g (yield 54%) of the above-titled compound as an oily product.

NMR($CDCl_3$) δ: 1.60–2.00(6H,m), 1.95(3H,s), 2.60–2.85 (3H,m), 2.81(3H,s), 3.20–3.50(3H,m), 5.63(1H,br s), 6.40–6.47(2H,m), 6.89(1H,d,J=7.8 Hz).

Working Example 65

(R)-1-[2-(Acetylamino)ethyl)]-6-methoxyindan

1-[2-(Acetylamino)ethyl]-6-methoxyindan was subjected to optical resolution by means of a high performance liquid chromatography (pump, L-6000; detector, L-4000; date processing device, D-2500; autosampler, AS-2000; column, Ceramospher RU-1: mobile phase, methanol; flow rate, 0.6 ml/min; column temperature, 50° C.; detective wave-length, 290 nm; sample concentration, 6%; volume to be fed, 0.1 ml; feeding frequence, 100 times) to give the above-titled compound (99 mg), m.p.95–96° C. $[\alpha]_{Hg365}$ −61.3° (c 0.3, $CHCl_3$).

Working Example 66

(S)-1-[2-(Acetylamino)ethyl]-6-methoxyindan

By substantially the same procedure as in Working Example 65, 1-[2-(acetylamino)ethyl]-6-methoxyindan was subjected to optical resolution by means of a high performance liquid chromatography to give the above-titled compound (119 mg), m.p.93–94° C. $[\alpha]_{Hg365}$ +80.7° (c 0.3, $CHCl_3$).

Working Example 67

(R)-1-[2-(Trifluoroacetylamino)ethyl]-6-methoxyindan

A mixture of (R)-1-[2-(acetylamino)ethyl]-6-methoxyindan (50 mg, 0.21 mmol) and hydrazine hydrate (1 ml) was heated under reflux for 26 hours under argon atmosphere. The reaction mixture was cooled, to which was added brine, followed by extraction with chloroform. The extract solution was washed with brine, followed by drying over anhydrous magnesium sulfate. The solvent was distilled off under reduced pressure to give 39 mg (yield 95%) of (R)-1-(2aminoethyl)-6-methoxyindan as an oily product. This product was dissolved in chloroform (0.8 ml), to which was added triethylamine (57 μL, 0.41 mmol), and the mixture was cooled with ice. To the mixture was added dropwise trifluoroacetic anhydride (43 μL, 0.31 mmol), which was stirred for 20 minutes. To the reaction mixture was added water, which was subjected to extraction with ethyl acetate. The extract solution was washed with brine, which was dried over anhydrous magnesium sulfate, followed by distillation of the solvent under reduced pressure. The residue was purified by means of a silica gel column chromatography (hexane/ethyl acetate, 7:3) to give 41 mg (yield 70%) of the above-titled compound, m.p.65–66° C. (recrystallized from isopropyl ether/hexane). $[\alpha]_{Hg365}$ −51.8° (c 0.3, $CHCl_3$)

Working Example 68

(S)-1-[2-Trifluroacetylamino)ethyl]-6-methoxyindan

By substantially the same procedure as in Working Example 67, 38 mg (yield 93%) of (S)-1-(2-aminoethyl)-6- methoxyindan was produced from (S)-1-[2-(acetylamino) ethyl]-6-methoxyindan (50 mg, 0.21 mmol). A small portion of this product was converted to hydrochloride using HCl/ethanol. The product was precipitated by the addition of diethyl ether. $[\alpha]_D$ −30.0°(c 0.15, $H_2O$) m.p.180–181° C. The free base was subjected to trifluoroacetylation in substantially the same manner as in Working Example 67 to give the above titled compound (yield 63%), m.p.65–66° C. (recrystallized from isopropyl ether/hexane). $[\alpha]_{Hg365}$ +54.9° (c 0.3, $CHCl_3$).

Working Example 69

1-[2-(Isobutyrylamino)ethyl]-6-methoxyindan

By substantially the same procedure as in Working Example 1, the above-titled compound was prepared from 1-(2-aminoethyl)-6-methoxyindan and isobutyryl chloride (yield 94%), m.p. 104–105° C. (recrystallized from ethyl acetate/isopropyl ether).

NMR($CDCl_3$) δ: 1.14(6H,d,J=6.6 Hz), 1.50–1.81(2H,m), 1.96–2.14(1H,m), 2.25–2.40(2H,m), 2.68–2.95(2H,m), 3.02–3.18(1H,m), 3.32–3.44(2H,m), 3.78(3H,s), 5.49(1H,br s), 6.67–6.75(2H,m), 7.11(1H,d,J=8.0 Hz).

Elemental Analysis for $C_{16}H_{23}NO_2$: Calcd.: C, 73.53; H, 8.87; N, 5.36. Found: C, 73.64; H, 9.02; N, 5.35.

Working Example 70

(S)-1-[2-(3-Ethylureido)ethyl]-6-methoxyindan

To a suspension of (S)-1-(2-aminoethyl)-6-methoxyindan hydrochloride (0.10 g, 0.44 mmol) and triethylamine (61 μl, 0.44 mmol) in acetonitrile (3 ml) was added ethyl isocyanate (35 μl, 0.44 mmol). The mixture was stirred for 30 min at room temperature, then diluted with water and the product was extracted with ethyl acetate. The extract was washed with 1N hydrochloric acid and brine, dried over anhydrous magnesium sulfate, and the solvent was removed in vacuo. The residue was recrystallized from ethyl acetate and isopropyl ether to afford the titled compound (79 mg, yield 69%), m.p. 104–105° C. $[\alpha]_{Hg365}$ +48.80 (c 0.5, $CHCl_3$)

NMR($CDCl_3$) δ: 1.14(3H,t,J=7.2 Hz), 1.52–1.80(2H,m), 1.97–2.15(1H,m), 2.26–2.40(1H,m), 2.68–2.95(2H,m), 3.07–3.37(5H,m), 3.79(3H,s), 4.20–4.35(2H,m), 6.68–6.75 (2H,m), 7.11(1H,d,J=8.2 Hz).

Working Example 71

1-[2-(4-Bromobenzoylamino)ethyl]-6-methoxyindan

By substantially the same procedure as in Working Example 1, the above-titled compound was prepared from 1-(2-aminoethyl)-6-methoxyindan and 4-bromobenzoyl chloride (yield 94%), m.p. 142–143° C. (recrystallized from ethyl acetate).

NMR($CDCl_3$) δ: 1.62–1.95(2H,m), 2.03–2.24(1H,m), 2.26–2.43(1H,m), 2.70–2.96(2H,m), 3.12–3.30(1H,m), 3.56–3.63(2H,m), 3.77(3H,s), 6.09(1H,br s), 6.68–6.77(2H, m), 7.12(1H,d,J=8.0 Hz), 7.55(4H,s).

Elemental Analysis for $C_{19}H_{20}BrNO_2$: Calcd.: C, 73.53; H, 8.87; N, 5.36. Found C, 73.64; H, 9.02; N, 5.35.

Working Example 72

6-Methoxy-2-phenyl-1-[2-(trifluoroacetylamino) ethyl]indan

By substantially the same procedure as in Working Example 11, the above-titled compound was prepared from 5-methoxy-2-phenyl-3-[2-(trifluoroacetylamino)ethyl]-1H-indene (yield 68%), m.p. 109–111° C. (recrystallized from ethyl acetate and hexane).

NMR($d_6$-DMSO) δ: 1.20–1.45(2H,m), 2.95–3.38(5H,m), 3.70–3.82(1H,m), 3.75(3H,s), 6.76(1H,dd,J=2.4 Hz,8.2 Hz), 6.90(1H,d,J=2.4 Hz), 7.16–7.36(6H,m), 9.31(1H,br s).

Elemental Analysis for $C_{20}H_{20}F_3NO_2$: Calcd.: C, 66.11; H, 5.55; N, 3.85; F, 15.68. Found: C, 66.04; H, 5.58; N, 3.79; F, 15.73.

Working Example 73

1-[3-(Trifluoroacetylamino)propyl]-7-methoxy-1,2,3,4-tetrahydronaphthalene

By substantially the same procedure as in Working Example 11, the above-titled compound was prepared from 4-[3-(trifluoroacetylamino)propyl]-6-methoxy-1,2-dihydronaphthalene (yield 91%, oil).

NMR($CDCl_3$) δ: 1.53–1.90(8H,m), 2.69(2H,t,J=5.7 Hz), 2.77(1H,m), 3.30–3.46(2H,m), 3.78(3H,s), 6.33(1H,br s), 6.65–6.73(2H,m), 6.99(1H,d,J=9.2 Hz).

Elemental Analysis for $C_{16}H_{20}F_3NO_2$: Calcd.: C, 60.94; H, 6.39; N, 4.44. Found: C, 61.01; H, 6.30; N, 4.39.

Working Example 74

1-[3-(Acetylamino)propyl]-7-methoxy-1,2,3,4-tetrahydronaphthalene

By substantially the same procedure as in Working Example 11, the above-titled compound was prepared from 4-[3-(acetylamino)propyl]-6-methoxy-1,2-dihydronaphthalene (yield 84%), m.p. 71–73° C. (recrystallized from ethyl acetate and hexane).

NMR($CDCl_3$) δ: 1.50–1.95(8H,m), 1.97(3H,s), 2.61–2.81 (3H,m), 3.20–3.35(2H,m), 3.78(3H,s), 5.47(1H,br s), 6.63–6.71(2H,m), 6.98(1H,d,J=9.2 Hz).

Elemental Analysis Calcd for $C_{16}H_{23}NO_2$: Calcd.: C, 73.53; H, 8.87; N, 5.36. Found: C, 73.26; H, 8.66; N, 5.38.

Working Example 75

1-[4-(Trifluoroacetylamino)butyl]-7-methoxy-1,2,3,4-tetrahydronaphthalene

By substantially the same procedure as in Working Example 11, the above-titled compound was prepared from 4-[4-(trifluoroacetylamino)butyl]-6-methoxy-1,2-dihydronaphthalene (yield 58%, oil).

NMR($CDCl_3$) δ: 1.30–1.90(10H,m), 2.61–2.80(3H,m), 3.38(2H,q,J=6.7 Hz), 3.78(3H,s), 6.33(1H,br s), 6.64–6.72 (2H,m), 6.98(1H,d,J=9.1 Hz).

Elemental Analysis for $C_{17}H_{22}F_3NO_2$: Calcd.: C, 61.99; H, 6.79; N, 4.25; F, 17.30. Found: C, 61.79; H, 6.72; N, 4.11; F, 17.25.

Working Example 76

1-[4-(Acetylamino)butyl]-7-methoxy-1,2,3,4-tetrahydronaphthalene

By substantially the same procedure as in Working Example 11, the above-titled compound was prepared from 4-[4-(acetylamino)butyl]-6-methoxy-1,2-dihydronaphthalene (yield 86%, oil).

NMR($CDCl_3$) δ: 1.30–1.90(10H,m), 1.97(3H,s), 2.62–2.80(3H,m), 3.25(2H,q,J=6.4 Hz), 3.78(3H,s), 5.52 (1H,br s), 6.63–6.72(2H,m), 6.98(1H,d,J=8.8 Hz).

Elemental Analysis for $C_{17}H_{25}NO_2$: Calcd.: C, 74.14; H, 9.15; N, 5.09. Found: C, 73.92; H, 9.10; N, 5.04.

The chemical structures of the compounds obtained by the working Examples are as follows.

Reference Example 1

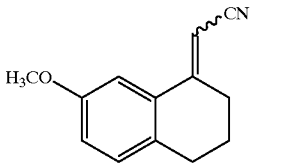

Reference Example 2

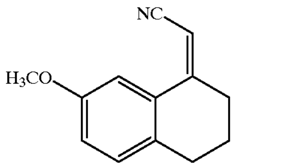

Reference Example 3

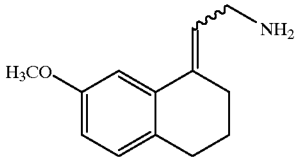

Reference Example 4

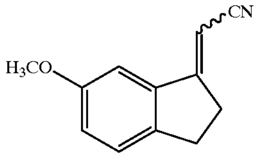

Reference Example 5

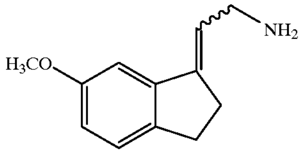

Reference Example 6

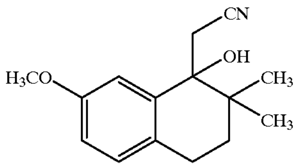

Reference Example 7

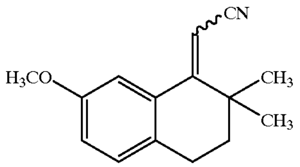

Reference Example 8

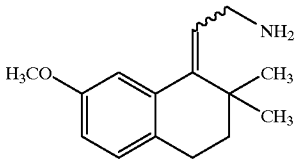

-continued

Reference Example 9

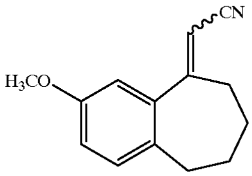

Reference Example 10

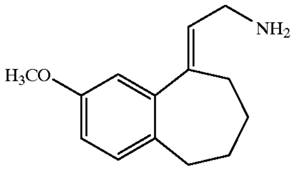

Reference Example 11

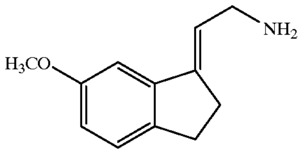

Reference Example 12

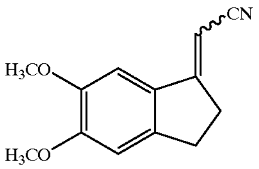

Reference Example 13

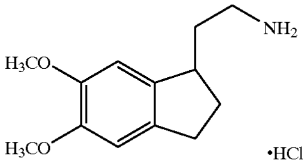

Reference Example 14

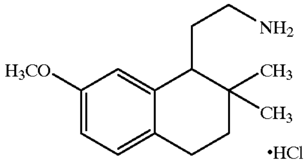

Reference Example 15

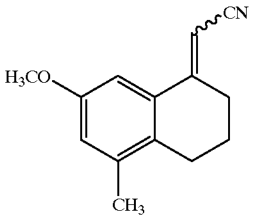

Reference Example 16

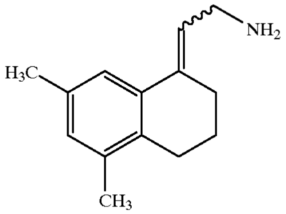

Reference Example 17
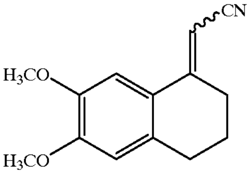
Reference Example 18
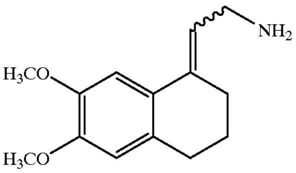
Reference Example 19
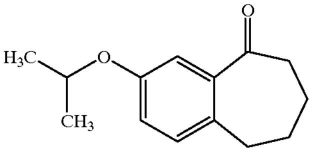
Reference Example 20
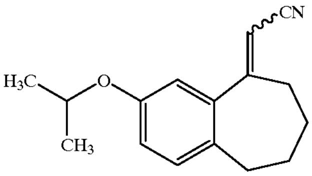
Reference Example 21
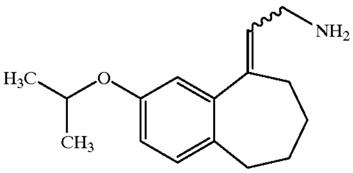
Reference Example 22
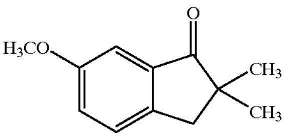
Reference Example 23
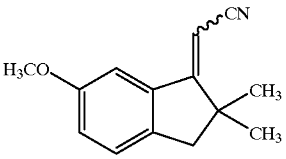
Reference Example 24
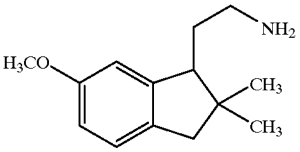
•HCl
Reference Example 25
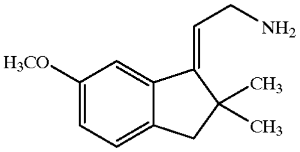
Reference Example 26
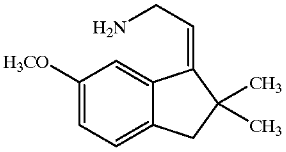
Reference Example 27
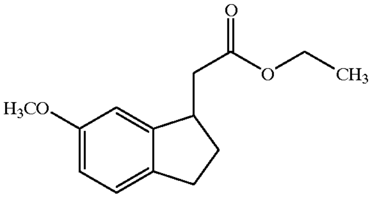
Reference Example 28
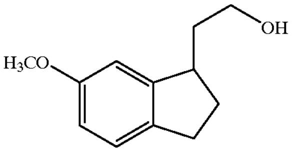
Reference Example 29
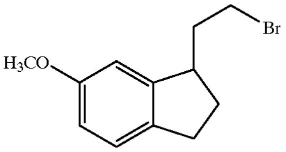
Reference Example 30
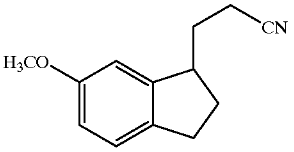
Reference Example 31
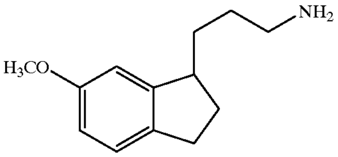
Reference Example 32
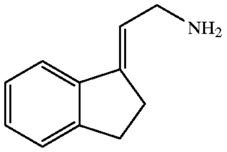

-continued
Reference Example 33
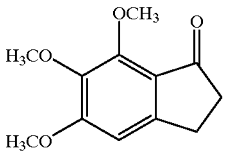
Reference Example 34
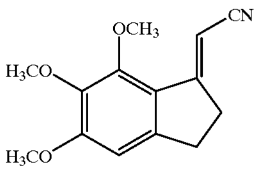
Reference Example 35
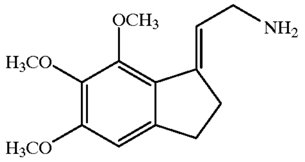
Reference Example 36
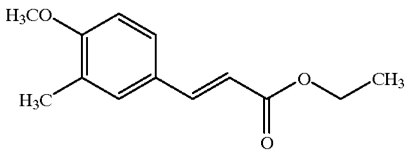
Reference Example 37
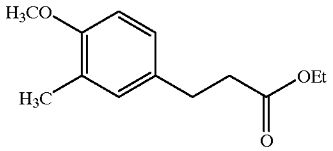
Reference Example 38
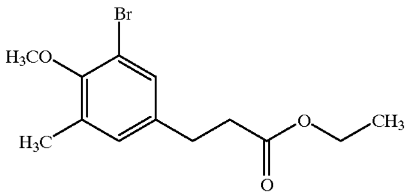
Reference Example 39
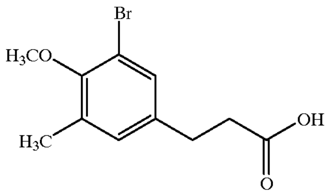
Reference Example 40
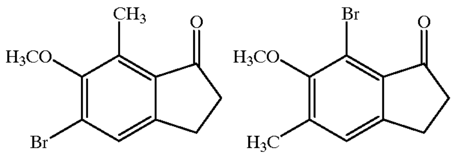
-continued
Reference Example 41
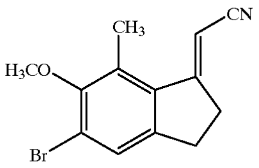
Reference Example 42
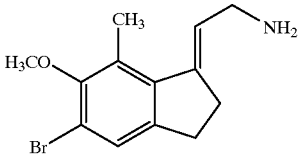
Reference Example 43
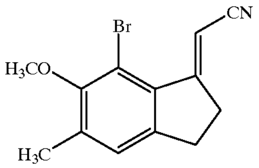
Reference Example 44
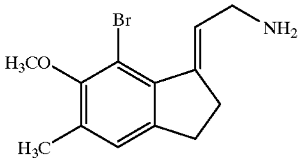
Reference Example 45
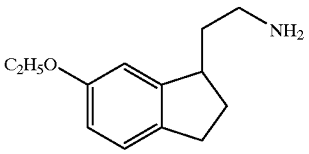
Reference Example 46
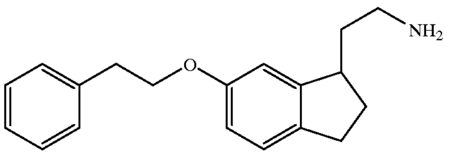
Reference Example 47
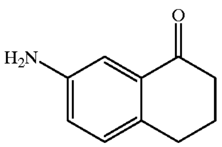
Reference Example 48
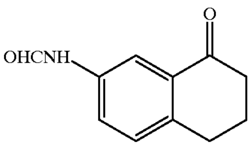

-continued
Reference Example 49
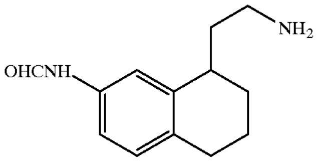
Reference Example 50
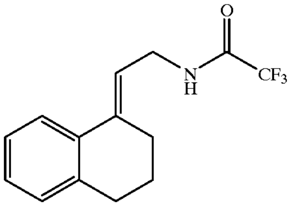
Reference Example 51
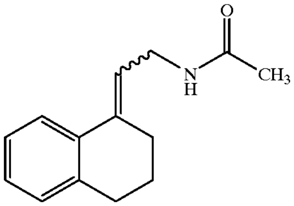
Reference Example 52
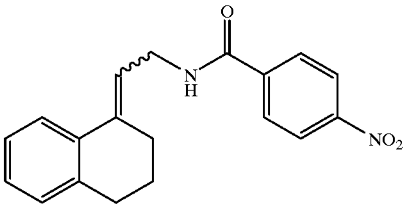
Reference Example 53
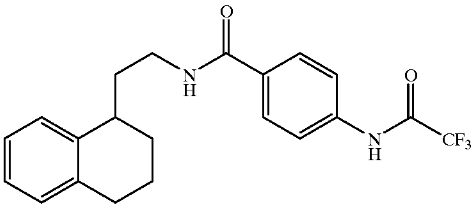
Reference Example 54
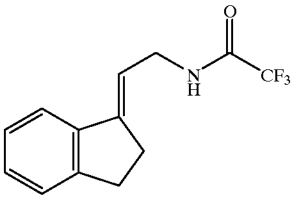
Reference Example 55
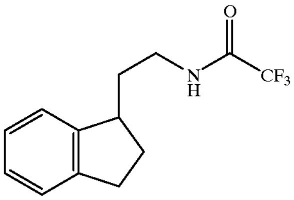
-continued
Reference Example 56
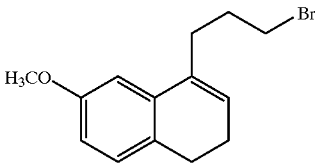
Reference Example 57
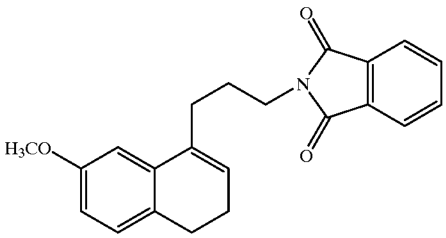
Reference Example 58
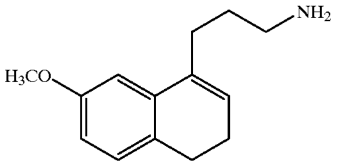
Reference Example 59
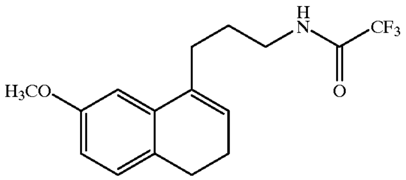
Reference Example 60
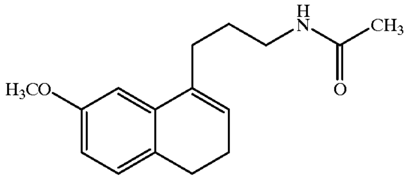
Reference Example 61
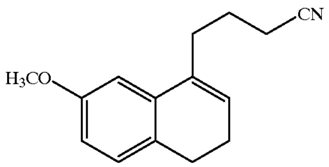
Reference Example 62
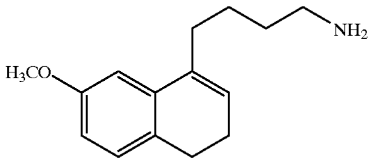

-continued
Reference Example 63
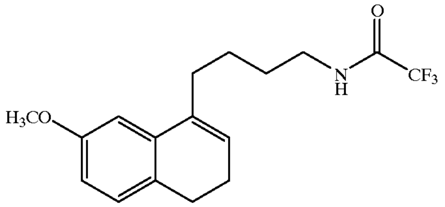
Reference Example 64
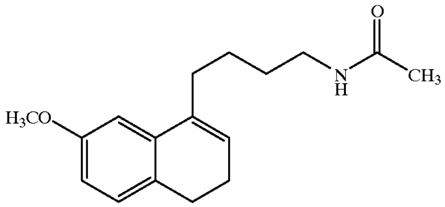
Reference Example 65
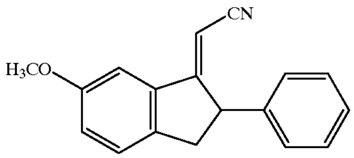
Reference Example 66
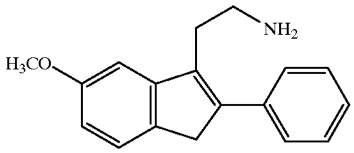
•HCl
Reference Example 67
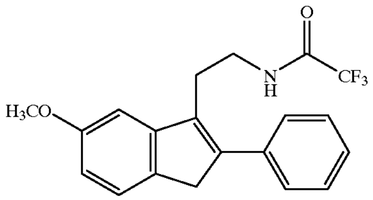
Working Example 1
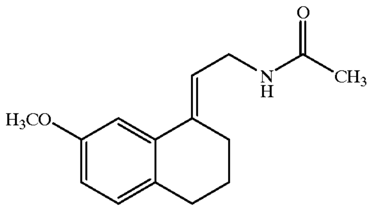
-continued
Working Example 2
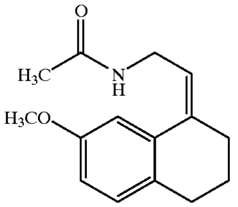
Working Example 3
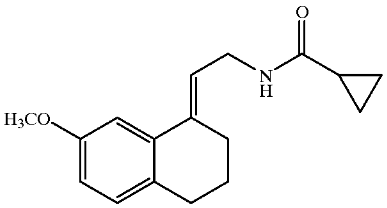
Working Example 4
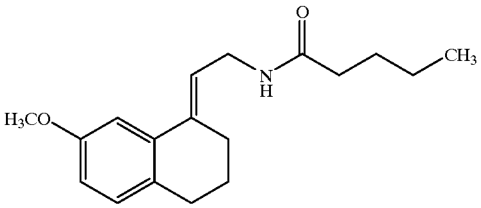
Working Example 5
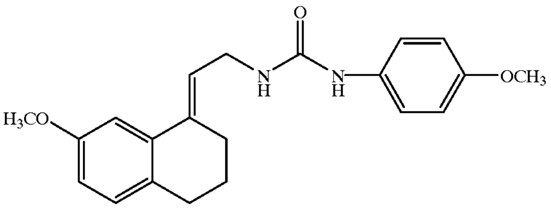
Working Example 6
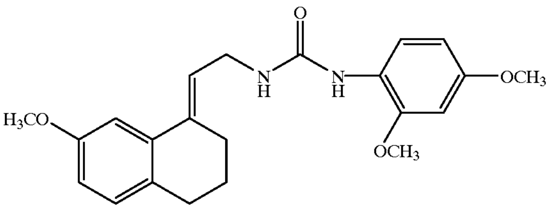
Working Example 7
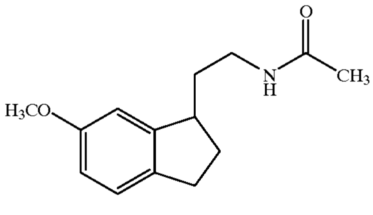

-continued
Working Example 8
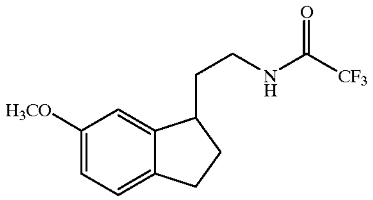
Working Example 9
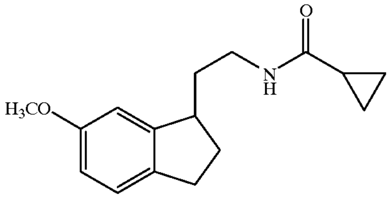
Working Example 10
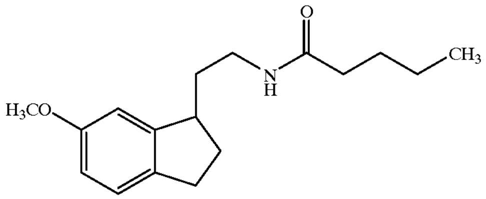
Working Example 11
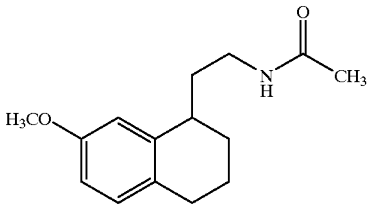
Working Example 12
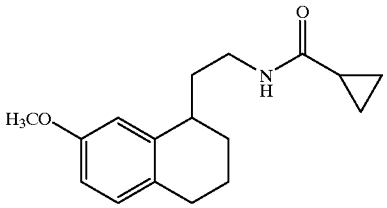
Working Example 13
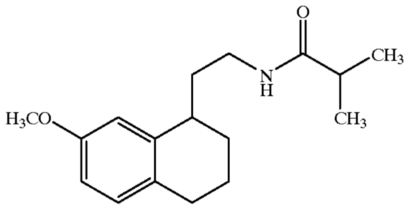
-continued
Working Example 14
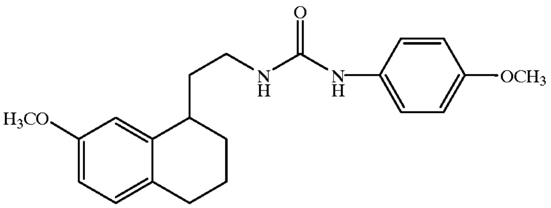
Working Example 15
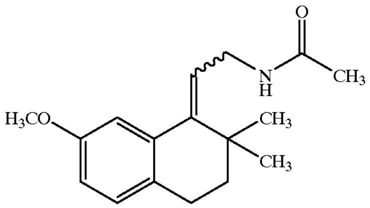
Working Example 16
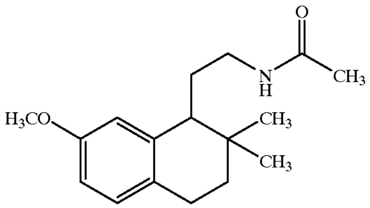
Working Example 17
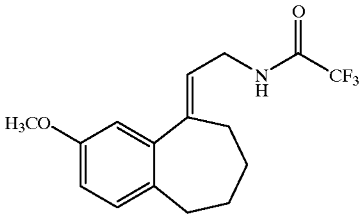
Working Example 18
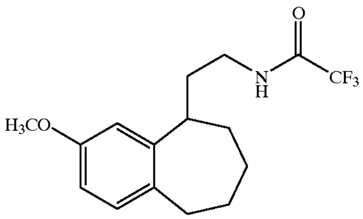
Working Example 19
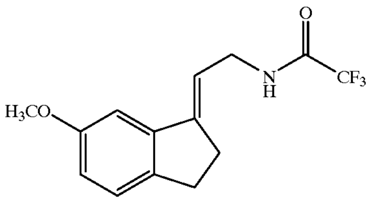

-continued
Working Example 20
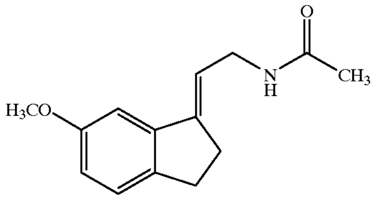
Working Example 21
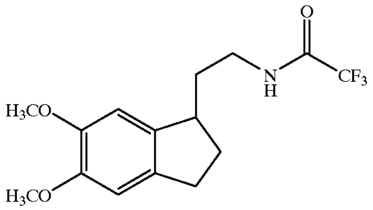
Working Example 22
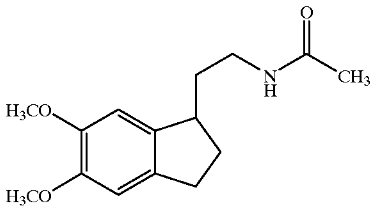
Working Example 23
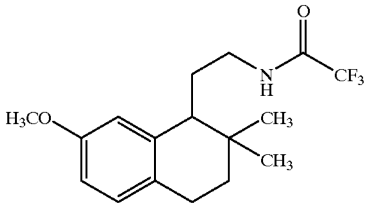
Working Example 24
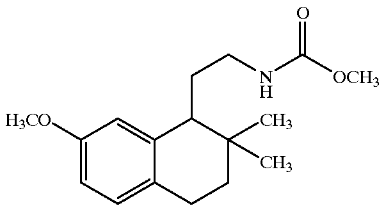
Working Example 25
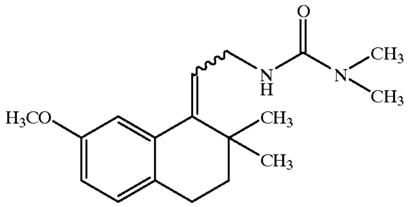
-continued
Working Example 26
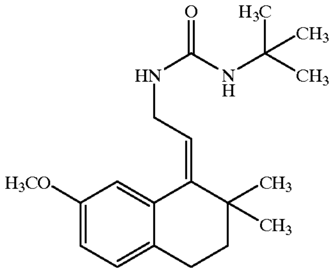
Working Example 27
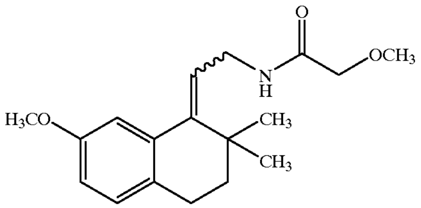
Working Example 28
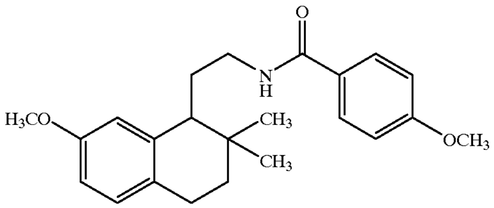
Working Example 29
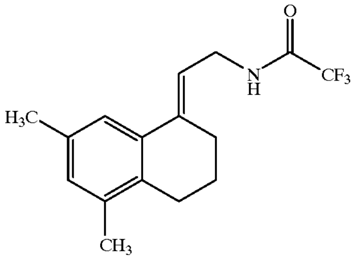
Working Example 30
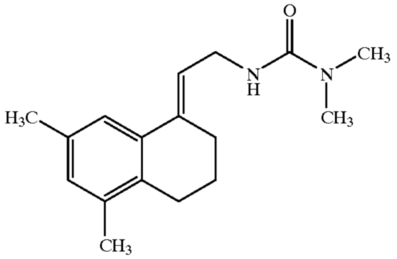

-continued
Working Example 31
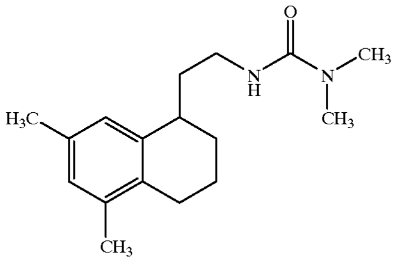
Working Example 32
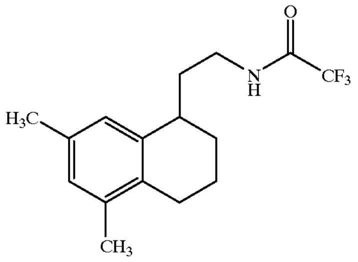
Working Example 33
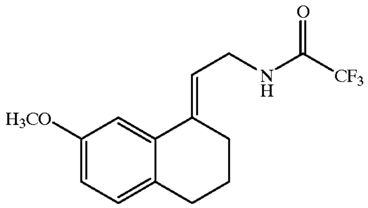
Working Example 34
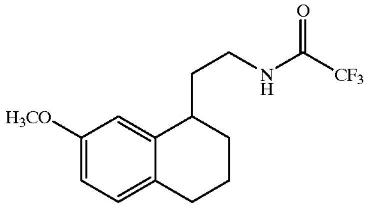
Working Example 35
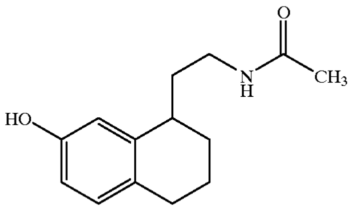
Working Example 36
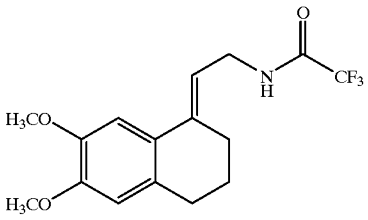
-continued
Working Example 37
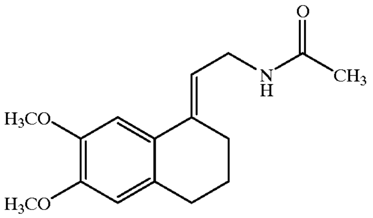
Working Example 38
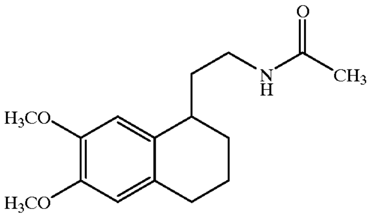
Working Example 39
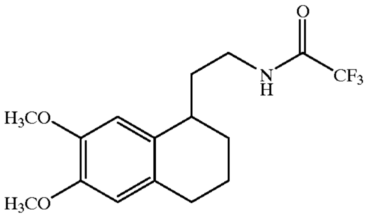
Working Example 40
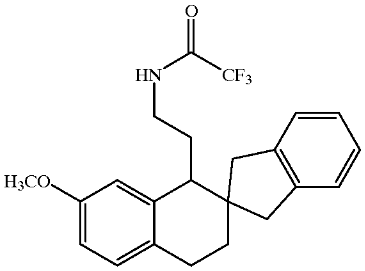
Working Example 41
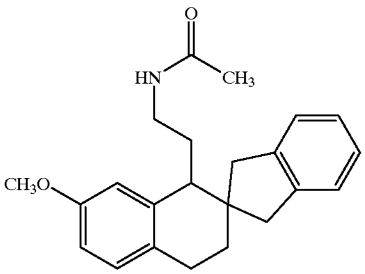

-continued
Working Example 42
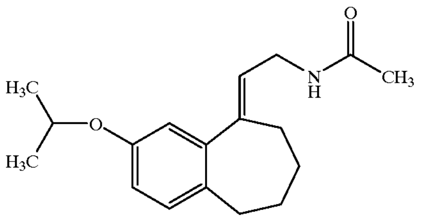
Working Example 43
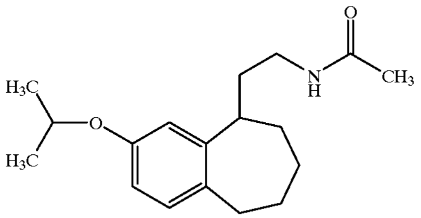
Working Example 44
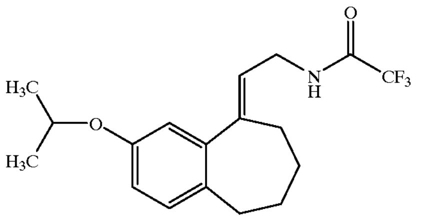
Working Example 45
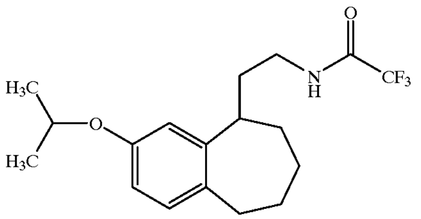
Working Example 46
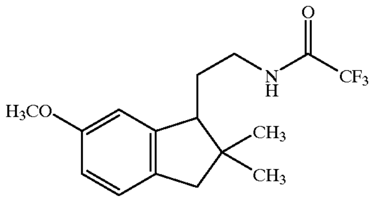
Working Example 47
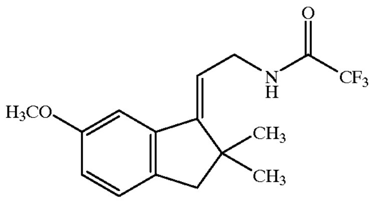
-continued
Working Example 48
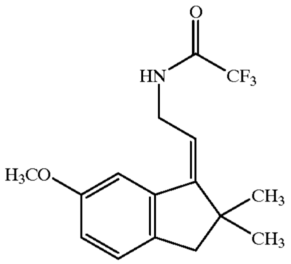
Working Example 49
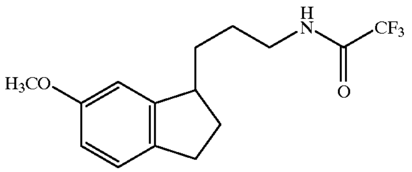
Working Example 50
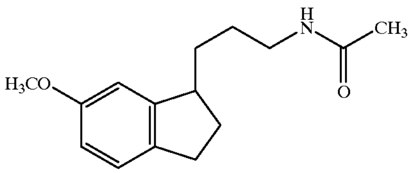
Working Example 51
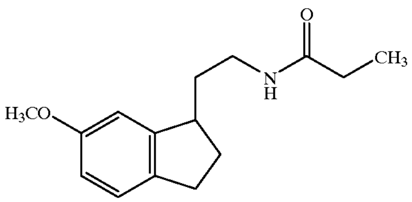
Working Example 52
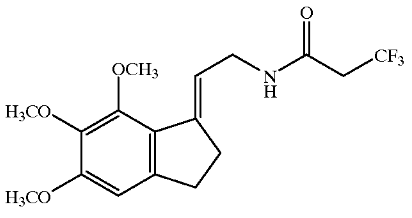
Working Example 53
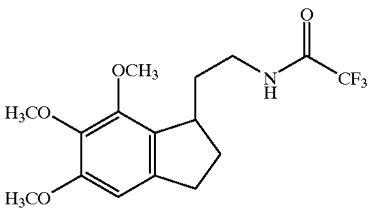

-continued
Working Example 54
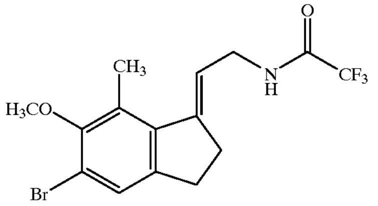
Working Example 55
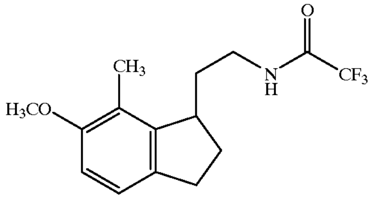
Working Example 56
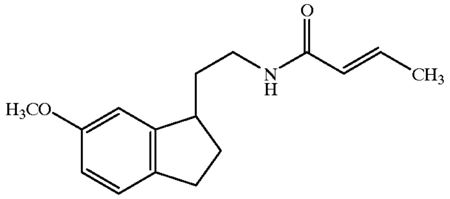
Working Example 57
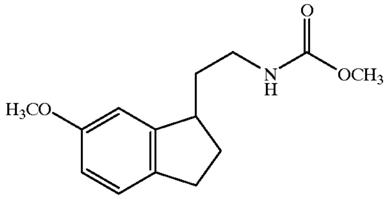
Working Example 58
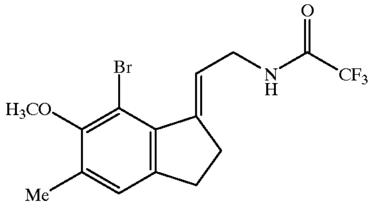
Working Example 59
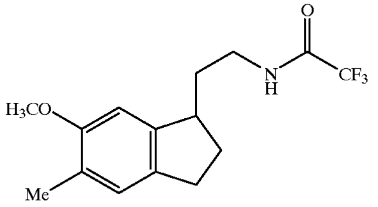
-continued
Working Example 60
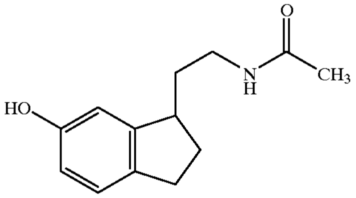
Working Example 61
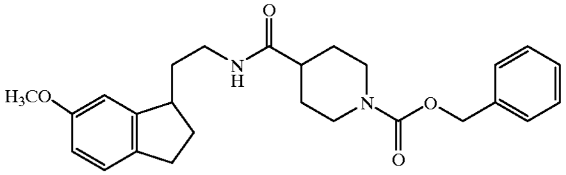
Working Example 62
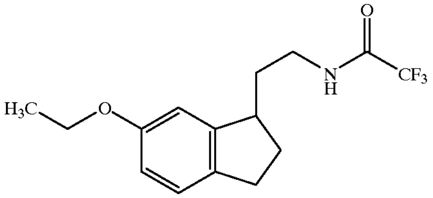
Working Example 63
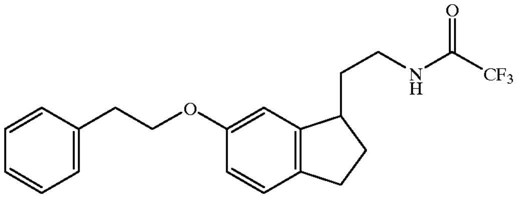
Working Example 64
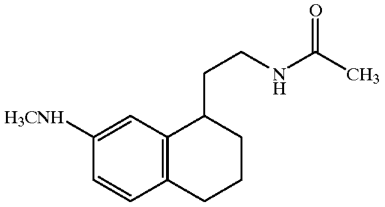
Working Example 65
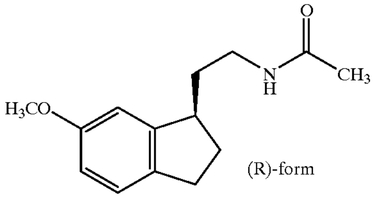
(R)-form -continued Working Example 66

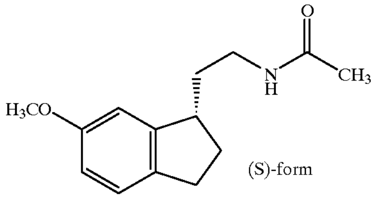

(S)-form

Working Example 67

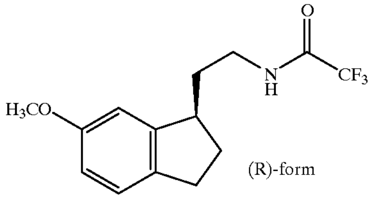

(R)-form

Working Example 68

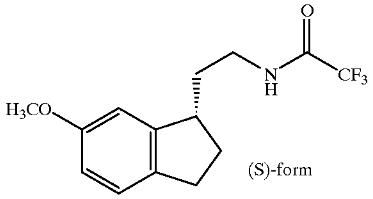

(S)-form

Working Example 69

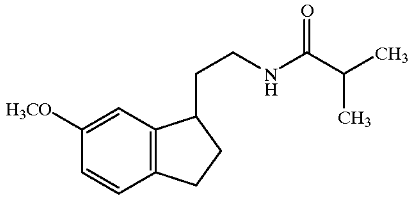

Working Example 70

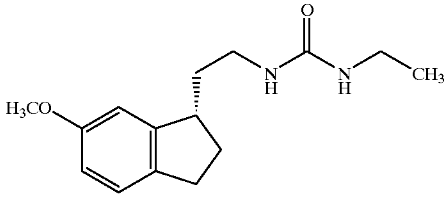

Working Example 71

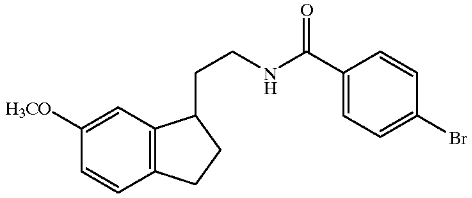

-continued

Working Example 72

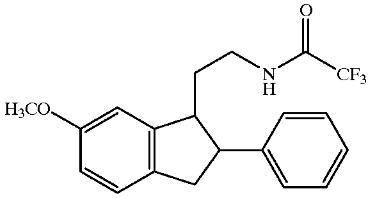

Working Example 73

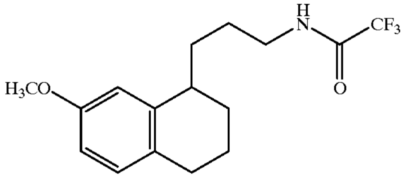

Working Example 74

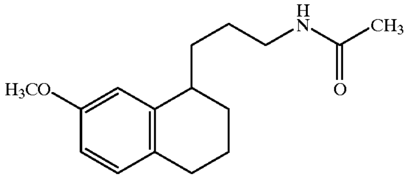

Working Example 75

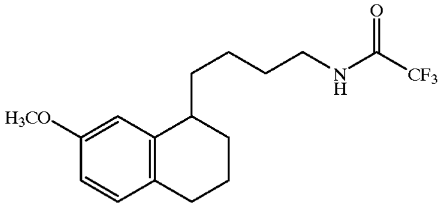

Working Example 76

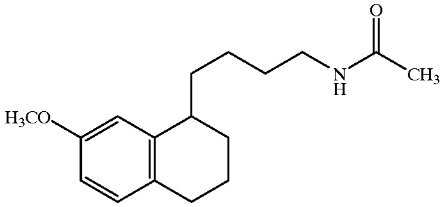

Formulation Example 1

| | |
|---|---|
| (1) Compound of Working Example 68 | 10.0 g |
| (2) Lactose | 60.0 g |
| (3) Corn starch | 35.0 g |
| (4) Gelatin | 3.0 g |
| (5) Magnesium stearate | 2.0 g |

Using 30 ml of a 10 weight % aqueous solution of gelatin (3.0 g in terms of gelatin), a mixture of 10.0 g of the compound produced in Working Example 68, 60.0 g of lactose and 35.0 g of corn starch was granulated through a sieve of 1 mm mesh. The granular product was dried at 40° C., which was sieved again. The granules thus obtained were blended with 2.0 g of magnesium stearate, and the mixture was subjected to compression. The core tablet thus obtained was sugar-coated with an aqueous suspension containing sucrose, titanium dioxide, talc and gum arabic. The coated tablets were polished with bee-wax to prepare 1000 tablets.

Formulation Example 2

| | |
|---|---|
| (1) Compound of Working Example 68 | 10.0 g |
| (2) Lactose | 70.0 g |
| (3) Corn starch | 50.0 g |
| (4) Soluble starch | 7.0 g |
| (5) Magnesium stearate | 3.0 g |

With 70 ml of an aqueous solution of soluble starch (7.0 g in terms of soluble starch), 10.0 g of the compound produced in Working Example 68 and 3.0 g of magnesium stearate were granulated and dried, followed by blending with 70.0 g of lactose and 50.0 g of corn starch. The mixture was subjected to compression to prepare 1000 tablets.

Experimental Example 1

The farebrains of 7-day-old chicken (white leghorn) were homogenized with ice-cold assay buffer (50 mM Tris-HCl, pH 7.7 at 25° C.) and centrifuged at 44,000×g for 10 minutes at 4° C. The pellet was washed once with the same buffer and stored at −30° C. until use. For the assay, the frozen tissue pellet was thawed and homogenized with the assay buffer to make a protein concentration of 0.3–0.4 mg/ml. An 0.4 ml aliquot of this homogenate was incubated with a test compound and 80 pM 2-[$^{125}$I]iodomelatonin in a total volume of 0.5 ml for 90 minutes at 25° C. The reaction was terminated by adding 3 ml of ice-cold assay buffer immediately followed by vacuum filtration on Whatman GF/B which was further washed twice with 3 ml of ice-cold assay buffer. The radioactivity on the filter was determined by means of γ-counter. Specific binding was calculated by subtracting non-specific binding which was determined in the presence of $10^{-5}$M melatonin. The 50% inhibiting concentration ($IC_{50}$) was determined by the log-probit analysis.

TABLE 1

Action of inhibiting 2-[$^{125}$I]iodomelatonin binding

| Compounds of Working Example | $IC_{50}$ (nM) |
|---|---|
| 8 | 0.64 |
| 33 | 0.72 |
| 35 | 0.95 |
| 51 | 0.45 |
| 66 | 0.70 |
| 68 | 0.16 |
| melatonin | 1.1 |

From the results shown in Table 1, it is considered that the compound (I) of the present invention has an excellent melatonin receptor agonistic activity.

Industrial Applicability

The compounds (I) of the present invention and the compound (Ia) show excellent affinity for a melatonin receptor, they can provide clinically useful prophylactic and therapeutic agents of diseases related with the action of melatonin in living bodies.

What is claimed is:

1. A compound represented by the formula:

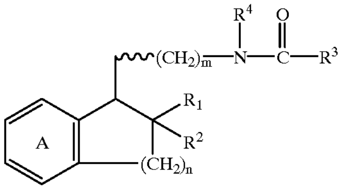

wherein n is 1 or 2, m is 1 or 2, ring A represents a substituted benzene ring wherein the substituents are selected from halogen, and optionally substituted alkoxy group, $R^1$ and $R^2$ independently represent a hydrogen atom or an optionally substituted hydrocarbon group, $R^3$ represents an optionally substituted hydrocarbon group, an optionally substituted amino group or an optionally substituted hydroxy group, $R^4$ is a hydrogen atom or an optionally substituted lower alkyl group, or a salt thereof.

2. A compound as in claim 1, in which the hydrocarbon group is a $C_{1-6}$ aliphatic hydrocarbon group, a $C_{3-6}$ monocyclic saturated hydrocarbon group or a $C_{6-10}$ aromatic group.

3. A compound as in claim 1, in which the substituent of the amino group is an optionally substituted lower alkyl group or an optionally substituted aryl group.

4. A compound as in claim 1, in which the substituted hydroxyl group is an optionally substituted lower alkoxy group.

5. A compound as in claim 1, in which $R^1$ and $R^2$ are independently a hydrogen atom, a lower alkyl group or an aryl group.

6. A compound as in claim 5, in which $R^1$ and $R^2$ are independently a hydrogen atom or a lower alkyl group.

7. A compound as in claim 1, in which $R^3$ is (i) an optionally substituted lower alkyl group, (ii) an optionally substituted lower cycloalkyl group, (iii) an optionally substituted lower alkenyl group, (iv) an optionally substituted aryl group, (v) an optionally substituted lower alkylamino group, (vi) an optionally substituted arylamino group or (vii) an optionally substituted lower alkoxy group.

8. A compound as in claim 7, in which $R^3$ is an optionally halogenated $C_{1-3}$ alkyl group.

9. A compound as in claim 1, in which $R^4$ is a hydrogen atom.

10. A compound as in claim 1, in which the ring A is a benzene ring having 1 to 3 substituents selected from the group consisting of (i) a halogen atom, (ii) a lower alkyl group, (iii) a lower alkoxy group optionally substituted with an aryl group, (iv) hydroxyl group and (v) a mono-lower alkylamino group.

11. A compound as in claim 1, in which the ring A is represented by the formula:

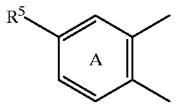

wherein $R^5$ is an optionally substituted lower alkoxy group.

12. A compound as in claim 1, in which $R^1$, $R^2$ and $R^4$ are all hydrogen atoms.

13. A compound as in claim 12, in which $R^3$ is an optionally halogenated lower alkyl group.

14. A compound as in claim 12, in which $R^3$ is a lower cycloalkyl group.

15. A compound as in claim 11, in which $R^1$, $R^2$ and $R^4$ are all hydrogen atoms, $R^3$ is an optionally halogenated lower alkyl group and m is 1.

16. A compound as in claim 11, which is
1-[2-acetylamino)ethyl]-6-methoxyindan,
(S)-1-[2-trifluoroacetylamino)ethyl]-6-methoxyindan,
(S)-1-[2-cyclopropylcarbonylamino)ethyl]-6-methoxyindan,
1-[2-(propionylamino)ethyl]-6-methoxyindan,
(S)-1-[2-(isobutyrylamino)ethyl]-6-methoxyindan.

17. A compound as in claim 1, which is (S)-1-[2-(trifluoroacetylamino)ethyl]-6-methoxyindan.

18. A compound as in claim 1, which is (S)-1-[2-(propionylamino)ethyl]-6-methoxyindan.

19. A compound as in claim 1, which is (S)-1-[2-(acetylamino)ethyl]-6-methoxyindan.

20. A pharmaceutical composition which comprises a compound of claim 1 or a pharmaceutically acceptable salt thereof, together with a pharmaceutically acceptable carrier.

21. The composition of claim 20, which has a binding affinity for melatonin receptor.

22. A method of regulating circadian rhythm, comprising administering a composition of claim 21 to a patient in need thereof.

23. A method of regulating sleep-awake rhythm, comprising administering a composition of claim 21 to a patient in need thereof.

24. A method of regulating time zone change syndrome comprising administering a composition of claim 21 to a patient in need thereof.

25. A method of treating sleep disorders, comprising administering a composition of claim 21 to a patient in need thereof.

26. A compound represented by the formula

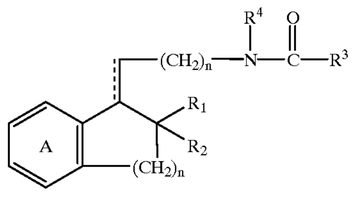

wherein $R^1$ and $R^2$ independently represent a hydrogen atom or an optionally substituted hydrocarbon group or $R^1$ and $R^2$ taken together with the adjacent carbon atom form an optionally substituted spiro ring;

$R^3$ represents an optionally substituted hydrocarbon group, an optionally substituted amino group or a substituted hydroxy group;

$R^4$ represents a hydrogen atom or an optionally substituted lower alkyl group, ring A represents a substituted benzene ring wherein the substituents are selected from hydrogen, halogen and an optionally substituted alkoxy group, n is 1 or 2, m is 1, 2, 3 or 4

= represents a single bond or a double bond with the proviso that if = represents a single bond, then $R^1$ and $R^2$ form an optionally substituted spiro ring.

27. A compound as in claim 26, in which the hydrocarbon group is a $C_{1-6}$ aliphatic hydrocarbon group, a $C_{3-6}$ monocyclic saturated hydrocarbon group or a $C_{6-10}$ aromatic group.

28. A compound as in claim 26, in which the spiro ring is a 3 to 8-membered ring.

29. A compound as in claim 26, in which the substituent of the amino group is an optionally substituted lower alkyl group or an optionally substituted aryl group.

30. A compound as in claim 26, in which the substituted hydroxyl group is an optionally substituted lower alkoxy group.

31. A compound as in claim 26, in which $R^1$ and $R^2$ are independently a hydrogen atom, a lower alkyl group or an aryl group.

32. A compound as in claim 31, in which $R^1$ and $R^2$ are independently a hydrogen atom or a lower alkyl group.

33. A compound as in claim 26, which $R^3$ is (i) an optionally substituted lower alkyl group, (ii) an optionally substituted lower cycloalkyl group, (iii) an optionally substituted lower alkenyl groups (iv) an optionally substituted aryl group, (v) an optionally substituted lower alkylamino group, (vi) an optionally substituted arylamino group or (vii) an optionally substituted lower alkoxy group.

34. A compound as in claim 33, in which $R^3$ is an optionally halogenated $C_{1-3}$ alkyl group.

35. A compound as in claim 26, in which $R^4$ is a hydrogen atom.

36. A compound as in claim 26, in which m is 1 or 2.

37. A compound as in claim 26, in which the ring A is a benzene ring having 1 to 3 substituents selected from the group consisting of (i) a halogen atom, (ii) a lower alkyl group, (iii) a lower alkoxy group optionally substituted with an aryl group, (iv) hydroxyl group and (v) a mono-lower alkylamino group.

38. A compound as in claim 26, which the ring A is represented by the formula:

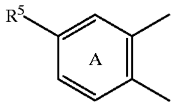

wherein $R^5$ is an optionally substituted lower alkoxy group.

39. A compound as in claim 26, in which $R^1$, $R^2$ and $R^4$ are all hydrogen atoms.

40. A compound as in claim 39, in which $R^3$ is an optionally halogenated lower alkyl group.

41. A compound as in claim 39, in which $R^3$ is a lower cycloalkyl group.

42. A compound as in claim 38, in which $R^1$, $R^2$ and $R^4$ are all hydrogen atoms, $R^3$ is an optionally halogenated lower alkyl group and m is 1.

43. A pharmaceutical composition which comprises a compound of claim 26 or a pharmaceutically acceptable salt thereof, together with a pharmaceutically acceptable carrier.

44. A composition of claim 43, which has a binding affinity for melatonin receptor.

45. A method of regulating circadian rhythm, comprising administering a composition of claim 44 to a patient in need thereof.

46. A method of regulating sleep-awake rhythm, comprising administering a composition of claim 44 to a patient in need thereof.

47. A method of regulating time zone change syndrome comprising administering a composition of claim 44 to a patient in need thereof.

48. A method of treating sleep disorders, comprising administering a composition of claim 44 to a patient in need thereof.

49. A process for producing a compound as in claim 1, which comprises reacting a compound represented by the formula:

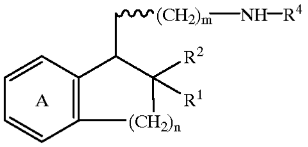

or a salt thereof, with a carboxylic acid of the formula:

$R^3COOH$, or a salt or reactive derivative thereof, or an isocyanate derivative of the formula:

$R^{3'}N{=}C{=}O$ (wherein $R^{3'}$ represents an optionally substituted hydrocarbon group, an optionally substituted amino group or a substituted hydroxyl group, with the proviso that $R^{3'}$ cannot be —NH) wherein A, $R^1$, $R^2$, $R^3$, $R^4$, m and n are as described in claim 1.

50. A process for producing a compound as in claim 26, which comprises reacting a compound represented by the formula:

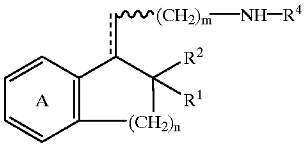

or a salt thereof, with a carboxylic acid of the formula:

$R^3COOH$, or a salt or reactive derivative thereof, or an isocyanate derivative of the formula:

$R^{3'}N{=}C{=}O$ (wherein $R^{3'}$ represents an optionally substituted hydrocarbon group, an optionally substituted amino group or a substituted hydroxyl group, with the proviso that $R^{3'}$ cannot be —NH) wherein A, $R^2$, $R^3$, $R^4$, m, n and ═ are as described in claim 26.

* * * * *

UNITED STATES PATENT AND TRADEMARK OFFICE

CERTIFICATE OF CORRECTION

PATENT NO. : 6,235,789 B1

DATED : May 22, 2001

INVENTOR(S) : Shigenori Ohkawa et al.

It is certified that error appears in the above-identified patent and that said Letters Patent is hereby corrected as shown below:

Column 88,
Lines 5-15, please change

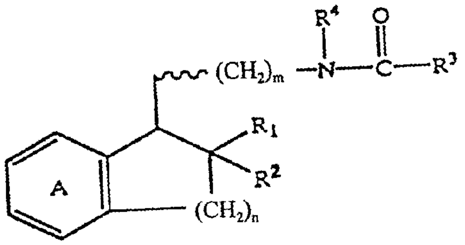

to

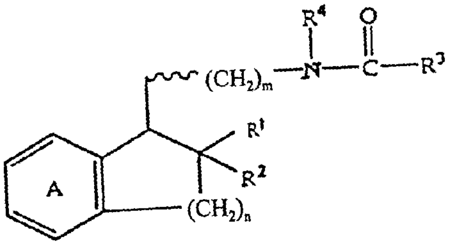

Column 89,
Lines 48-57, please change

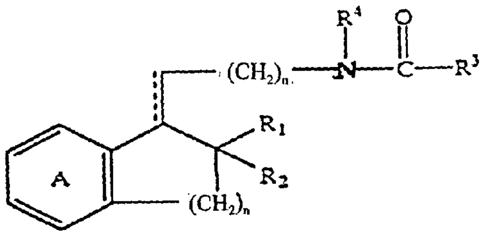

to

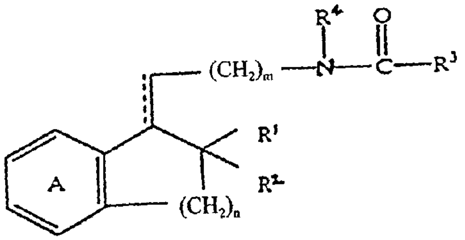

UNITED STATES PATENT AND TRADEMARK OFFICE

CERTIFICATE OF CORRECTION

PATENT NO. : 6,235,789 B1 
DATED : May 22, 2001
INVENTOR(S) : Shigenori Ohkawa et al.

It is certified that error appears in the above-identified patent and that said Letters Patent is hereby corrected as shown below:

Column 90,
Line 6, "══════", should be "- - - -" .

Line 7, "══════", should be "- - - -" .

Signed and Sealed this

Twenty-fifth Day of June, 2002

*Attest:*

JAMES E. ROGAN

*Attesting Officer* *Director of the United States Patent and Trademark Office*